(12) United States Patent
Briskin et al.

(10) Patent No.: US 7,803,904 B2
(45) Date of Patent: Sep. 28, 2010

(54) MUCOSAL VASCULAR ADDRESSING AND USES THEREOF

(75) Inventors: Michael J. Briskin, Lexington, MA (US); Douglas J. Ringler, Revere, MA (US); Dominic Picarella, Sudbury, MA (US); Walter Newman, Boston, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 1745 days.

(21) Appl. No.: 08/875,849

(22) PCT Filed: Feb. 12, 1996

(86) PCT No.: PCT/US96/02153

§ 371 (c)(1),
(2), (4) Date: Sep. 3, 1997

(87) PCT Pub. No.: WO96/24673

PCT Pub. Date: Aug. 15, 1996

(65) Prior Publication Data

US 2002/0147314 A1    Oct. 10, 2002

Related U.S. Application Data

(63) Continuation-in-part of application No. 08/523,004, filed on Sep. 1, 1995.

(51) Int. Cl.
*C07K 19/00* (2006.01)
*C07K 16/46* (2006.01)
*C07K 14/705* (2006.01)

(52) U.S. Cl. .......... 530/350; 530/387.3; 530/391.7; 530/402; 530/866

(58) Field of Classification Search .............. 530/391.1, 530/391.7, 395, 402, 866, 300
See application file for complete search history.

(56) References Cited

U.S. PATENT DOCUMENTS

| | | | |
|---|---|---|---|
| 4,699,880 A | 10/1987 | Goldstein | |
| 5,223,392 A | 6/1993 | Cohen | |
| 5,225,538 A | 7/1993 | Capon et al. | 530/387.3 |
| 5,403,919 A | 4/1995 | Butcher | 530/388.22 |
| 5,428,130 A | 6/1995 | Capon et al. | 530/350 |
| 5,538,724 A | 7/1996 | Butcher et al. | 424/152.1 |
| 5,565,335 A | 10/1996 | Capon et al. | 435/64.7 |
| 5,599,676 A | 2/1997 | Vonderheide et al. | 435/7.2 |
| 5,624,321 A | 4/1997 | Snyder | 435/69.6 |
| 5,648,260 A | 7/1997 | Winter et al. | 435/252.3 |
| 5,714,147 A | 2/1998 | Capon et al. | 424/178.1 |

FOREIGN PATENT DOCUMENTS

| | | |
|---|---|---|
| EP | 0 303 463 B1 | 11/1994 |
| GB | 2 209 757 | 5/1989 |
| WO | WO 88/07089 | 9/1988 |
| WO | WO 89/07142 | 8/1989 |
| WO | 90/07321 | 7/1990 |
| WO | 93/15764 | 8/1993 |
| WO | 93/23526 | 11/1993 |
| WO | 94/13312 | 6/1994 |
| WO | 94/16094 | 7/1994 |
| WO | WO 94/29351 | 12/1994 |
| WO | 95/19790 | 7/1995 |

OTHER PUBLICATIONS

Lederman et al., Molec. Immunol., 28:1171-1181, 1991.*
Ringler, D.J. et al., "Cellular Localization of Simian Immuno-deficiency Virus in Lymphoid Tissues I. Immunohistochemistry and Electron Microscopy", *Am. J. Path.*, 134(2):373-383 (1989).
Strober, Warren and Ehrhardt, Rolf O., "Chronic Intestinal Inflammation: An Unexpected Outcome in Cytokine or T Cell Receptor Mutant Mice", *Cell*, 75:203-205 (1993).
Sadlack, Benjamin et al., "Ulcerative Colitis-like Disease in Mice with a Disrupted Interleukin-2 Gene", *Cell*, 75:253-261 (1993).
Hamann, Alf et al., "Role of $\alpha_4$-Integrins in Lymphocyte Homing to Mucosal Tissues In Vivo", *J. Immunol.*, 152:3282-3293 (1994).
Cooper, Harry S. et al., "Clinicopathologic Study of Dextran Sulfate Sodium Experimental Murine Colitis", *Laboratory Investigation*, 69(2):238-249 (1993).
Podolsky, Daniel K. et al., "Attenuation of Colitis in the Cotton-top Tamarin by Anti-$\alpha_4$ integrin Monoclonal Antibody", *J. Clin. Invest.*, 92:372-380 (1993).
Okayasu, Isao et al., "A Novel Method in the Induction of Reliable Experimental Acute and Chronic Ulcerative Colitis in Mice", *Gastroenterology*, 98:694-702 (1990).
Podolsky, Daniel K., "Inflammatory Bowel Disease (First of Two Parts)", *N. Engl. J. Med.*, 325(13):928-937 (1991).
Podolsky, Daniel K., "Inflammatory Bowel Disease (Second of Two Parts)", *N. Engl. J. Med.*, 325(14):1008-1016 (1991).
Springer, Timothy A., "The Sensation and Regulation of Interactions with the Extracellular Environment: The Cell Biology of Lymphocyte Adhesion Receptors", *Annu. Rev. Cell Biol.*, 6:359-402 (1990).
Dueñas, Marta and Borrebaeck, Carl A.K., "Clonal Selection and Amplification of Phage Displayed Antibodies by Linking Antigen Recognition and Phage Replication", *Bio/Technology*, 12:999-1002 (1994).
Picker, Louis, J. and Butcher, Eugene C., "Physiological and Molecular Mechanisms of Lymphocyte Homing", *Annu. Rev. Immunol.*, 10:561-591 (1992).

(Continued)

*Primary Examiner*—Ron Schwadron
(74) *Attorney, Agent, or Firm*—McDermott Will & Emery LLP

(57) ABSTRACT

The present invention relates to fusion proteins comprising a naturally occurring primate MAdCAM, wherein said naturally occurring primate MAdCAM binds $\alpha 4\beta 7$ integrin and has at least about 75% amino acid similarity to an amino acid sequence selected from the group consisting of SEQ ID NO:2, SEQ ID NO:4 and SEQ ID NO:6.

60 Claims, 27 Drawing Sheets

OTHER PUBLICATIONS

Hynes, Richard O., "Integrins: Versatility, Modulation, and Signaling in Cell Adhesion", *Cell*, 69:11-25 (1992).
Michie, Sara A. et al., "The Human Peripheral Lymph Node Vascular Addressin, An Inducible Endothelial Antigen Involved in Lymphocyte Homing", *Am. J. Path.*, 143(6):1688-1698 (1993).
Berlin, Cornelia et al., "α4β7 Integrin Mediates Lymphocyte Binding to the Mucosal Vascular Addressin MAdCAM-1", *Cell*, 74:185-195 (1993).
Schweighoffer, Tamas et al., "Selective Expression of Integrin α4β7 on a Subset of Human CD4+Memory T Cells with Hallmarks of Gut-Trophism", *J. Immunol.*, 151(2):717-729 (1993).
Springer, Timothy A., "Traffic Signals for Lymphocyte Recirculation and Leukocyte Emigration: The Multistep Paradigm", *Cell*, 76:301-314 (1994).
Briskin, Michael J. et al., "MAdCAM-1 has homology to immunoglobulin and mucin-like adhesion receptors and to IgA1", *Nature*, 363:461-463 (1993).
Salmi, Marko et al., "Aberrant Binding of Lamina Propria Lymphocytes to Vascular Endothelium in Inflammatory Bowel Diseases", *Gastroenterology* 106:596-605 (1994).
Silber, Alexandra et al., "Recruitment of Lymphocytes during Cutaneous Delayed Hypersensitivity in Nonhuman Primates is Dependent on E-Selectin and Vascular Cell Adhesion Molecule 1", *J. Clin. Invest.*, 93:1554-1563 (1994).
Salmi, Marko et al., "Dual Binding Capacity of Mucosal Immunoblasts to Mucosal and Synovial Endothelium in Humans: Dissection of the Molecular Mechanisms", *J. Exp. Med.*, 181: 137-149 (1995).
Andrew, David P. et al., "Distinct but Overlaping Epitopes Are Involved in α4β7-Mediated Adhesion to Vasculr Cell Adhesion Molecule-1, Mucosal Addressin-1, Fibronectin, and Lymphocyte Aggregation", *J. Immunol.*, 153:3847-3861 (1994).
Lazarovits, Andrew I. et al., "I. A Monoclonal Antibody, Anti-Act I, Defines a New Late Lymphocyte Activation Antigen", *J. Immunol.*, 133(4):1857-1862 (1984).
Schweighoffer, Tamas et al., "Selective Expression of Integrin α4β7 on a Subset of Human CD4+ Memory T Cells with Hallmarks of Gut-Trophism[1]", *J. Immunol.*, 151(2):717-729 (1993).
Erle, David J. et al., "Expression and Function of the MAdCAM-1 Receptor, Integrin α4β7, on Human Leukocytes[1]", *J. Immunol.*, 153:517-528 (1994).
Berg, E.L., et al., "L-selectin-mediated lymphocyte rolling on MAdCAM-1", *Nature*, 366:695-698 (1993).
Berlin, C., et al., "α4 Integrins Mediate Lymphocyte Attachment and Rolling under Physiologic Flow", *Cell*, 80:413-422 (1995).
Osband, M.E. and Ross, S., "Problems in the Investigational Study and Clinical Use of Cancer", *Immunol. Today*, 11(6):103-105 (1990).
Harris, W.J. and Emery,S., "Therapeutic Antibodies-The Coming of Age", *TIBTECH*, 11:42-44 (1993).
Waldmann, T.A., "Monoclonal Antibodies in Diagnosis and Therapy", *Science*, 252:1657-1662 (1991).
Yang, Y., et al., "Construction and Adhesive Properties of a Soluble MADCAM-1-Fc Chimera Expressed in a Baculovirus System: Phylogenetic Conservation of Receptor-Ligand Interaction," *Scand. J. Immunol.*, 42:235-247 (1995).
Bednarczyk, J.L., et al., "Identification of a Combinatorial Epitope Expressed by the Integrin α4β1 Heterodimer Involved in the Regulation of Cell Adhesion," *J. Biol. Chem.*, 269(11):8348-8354 (1994).
Briskin, M.J., et al., "Structural Requirements for Mucosal Vascular Addressin Binding to Its Lymphocyte Receptor α4β7", *J. Immunol.*, 156:719-726 (1996).
Shyjan, A.M et al., "Human Mucosal Addressin Cell Adhesion Molecule-1 (MAdCAM-1) Demonstrates Structural and Functional Similarities to the α4β7-Integrin Binding Domains of Murine MAdCAM-1, but Extreme Divergence of Mucin-Like Sequences," *J. of Immunology*, 156: 2851-2857 (1996).
Adams et al., "Aberrant Homing of Mucosal T Cells and Extra-Intestinal Manifestations of Inflammatory Bowel Disease," Nature, 6:244-251 (2006).
Adams et al., "Complementary DNA Sequencing: Expressed Sequence Tags and Human Genome Project," Science, 252:1651-1656 (1991).
Adams et al., "Initial Assessment of Human Gene Diversity and Expression Patterns Based Upon 83 Million Nucleotides of cDNA Sequence," Nature (Supp), 377:3-174 (1995).
Adams et al., "Sequence Identification of 2,375 Human Brain Genes," Nature, 355:632-633 (1992).
Andrew et al., "TABS, A T Cell Activation Antigen that Induces LFA-1-Dependent Aggregation," The Journal of Immunology, 155:1671-1684 (1995).
Aruffo et al., "Molecular Cloning of a CD28 cDNA by a High-Efficiency COS Cell Expression System," Proc. Natl. Acad. Sci. USA, 84:8573-8577 (1987).
Brossay et al., "Mimicry of a Neutralizing Epitope of the Major Outer Membrane Protein of Chlamydia Trachomatis by Anti-Idiotypic Antibodies," Infection and Immunity, 62:341-347 (1994).
Calvete et al., "Further Studies on the Topography of Human Platelet Glycoprotein IIb," Biochem, 273:767-775 (1991).
Chenna et al., "Multiple Sequence Alignment with the Clustal Series of Programs," Nucleic Acids Research, 31:3497-3500 (2003).
Feagan et al., "Treatment of Ulcerative Colitis with a Humanized Antibody to the $\alpha_4\beta_7$ Integrin," The New England Journal of Medicine, 352:2499:2507 (2005).
Grant et al., "MAdCAM-1 Expressed in Chronic Inflammatory Liver Disease Supports Mucosal Lymphocyte Adhsion to Hepatic Endothelium (MAdCAM-1 in Chronic Inflammatory Liver Disease)," Hepatology, 33:1065-1072 (2001).
Herlyn et al., "Anti-Idiotypic Antibodies Bear the Internal Image of a Human Tumor Antigen," Science 232:100-102 (1986).
Leung et al., "Cloning of the Mucosal Addressin MAdCAM-1 from Human Brain: Identification of Novel Alternatively Spliced Transcripts," Immunology and Cell Biology, 74:490-496 (1996).
Marlin et al., "Purified Intercellular Adhesion Molecule-1 (ICAM1) is a Ligand for Lymphocyte Function-Associated Antigen 1 (LFA-1)," Cell, 51:813-819 (1987).
Pennica et al., "Expression Cloning of Cardiotrophin 1, A Cytokine that Induces Cardiac Myocyte Hypertrophy," Proc. Natl. Acad. Sci., 92:1142-1146 (1995).
Petrovic et al., "LPAM ($\alpha_4\beta_7$ integrin) is an Important Homing Integrin on Alloreactive T Cells in the Development of Intestinal Graft-Versus-Host Disease," Blood, 103:1542-1547 (2004).
Prakash et al., "Cloning and Analysis of Murine cDNA that Encodes a Fibrogenic Lymphokine, Fibrosin," Proc. Natl. Acad., 92:2154-2158 (1995).
Prasad et al., "Evaluation of Mutagenesis for Epitope Mapping," The Journal of Biological Chemistry, 15:10705-10708 (1993).
Schweighoffer et al., "Selective Expression of Integrin $\alpha_4\beta_7$ on a Subset of Human CD4+ Memory T Cells with Hallmarks of Gut-Trophism," The Journal of Immunology, 151:717-729 (1993).
Silber et al, "Recruitment of Lymphocytes During Cutaneous Delayed Hypersensitivity in Nonhuman Primates is Dependent on E-Selectin and Vascular Cell Adhesion Molecule 1," J. Clin. Invest., 93:1554-1563 (1994).
Yacyshyn et al, "Crohn's Disease, Ulcerative Colitis, and Normal Intestinal Lymphocytes Express Integrins in Dissimilar Patterns," Gastroenterology, 107:1364-1371 (1994).
Yang et al., "Involvement of $\beta_7$ Integrin and Mucosal Addressin Cell Adhesion Molecule-1 (MAdCAM-1) in the Development of Diabetes in Nonobese Diabetic Mice," Diabetes, 46;1542-1547 (1997).

* cited by examiner

FIG. 1A

```
ATGGATTTCGGACTGGCCCTCCTGCTGGCTTCTCGGCCTTCTGGGCTTCCCAGGTCCCTGCAGGTGAAGCCCCTGCA        80
 M  D  F  G  L  A  L  L  L  A  G  L  L  G  L  L  L  G  Q  S  L  Q  V  K  P  L  Q

GGTGGAGCCCCCGGAGCCGGTGGTGGCCGTGCTTGGCGCCAGCCGCCTGGGCGCCTCACTGCGCCTGGCTGCGCGGACC       160
 V  E  P  P  E  P  V  V  A  V  A  L  G  A  S  R  Q  L  T  [C] R  L  A  [A] D

GCGGGGCCTCGGTGCAGTGCAGGCGCGGCCTGGACACCAGCCTGGGCGCGGTGCAGTCGGACACGGGCCGCAGTGTCCTCACC     240
 R  G  A  S  V  Q  W  R  G  L  D  T  S  L  G  A  V  Q  S  D  T  G  R  S  V  L  T

GTGCGCAACGCCTCGGCTGTCGGCCGGACCCGCGTGTGCTGGGCTCCTGCAGCCGTCCTCCAGCACACCGT         320
 V  R  [N] A  [S]  L  S  A  A  G  T  R  V  [C] V  G  S  [C] G  G  R  T  F  Q  H  T  V

GCAGCTCCTTGTGTACGCCTTCCCCGACCAGCTGACCGTGTCGCCCGCTGCTCTGGTGCCCGGAGGTGGCCT             400
 Q  L  V  Y  A  F  P  D  Q  L  T  V  S  P  A  A  L  V  P  G  D  P  E  V  A

GTACGGGCCCCACAAAGTCACGCCCGTGGACCCCAACGCGCTCTCCTTCTCCCTGGTCGTGGGGGCCAGGAACTGGAGGG         480
 [C] T  A  H  K  V  T  P  V  D  P  N  A  L  S  F  S  L  V  G  G  Q  E  L  E  G

GCGCAAGCCCTGGGGCCGGAGGTGCAGGAGGTGCAGGACGCTGTTCAGGGTGACAGA                       560
 A  Q  A  L  G  P  E  V  Q  E  E  E  E  P  Q  G  D  E  D  V  L  F  R  V  T  E

GCGCTGGCTGGGGGACCCCTGGGGACCCCCCTGTCCCCGGCCAGGCGATGAGGCTGCCTTGG                   640
 R  W  R  L  P  P  L  G  T  P  V  P  P  A  L  Y  [C] Q  A  T  M  R  L  P  G  L
```

FIG. 1B

```
AGCTCAGCCACCGCCAGCCATCCCGTGCTCCTGCACAGCCCGAGCCTCCCCGACACCACCCTCCCCGGAGCCT    720
 E  L  S  H  R  Q  A  I  P  V  L  H  S  P  T  S  P  E  P  P  D  T  T  S  P  E  P

CCCAACACCACCCTCCCCGGAGTCTCCCCAGGAGCCTCCCCGACACCACCCTCCCCGGAGCCTCCCCGACAC    800
 P  N  T  T  S  P  E  S  P  D  T  T  S  P  E  P  P  D  T  T  S  Q  E  P  P  D  T

CACCCTCCCCGGAGCCTCCCCGACACCACCCTCCCCGGAGCCTCCCCGACAAGACCTCCC              880
 T  S  Q  E  P  P  D  T  T  S  P  E  P  P  D  T  T  S  P  E  P  P  D  K  T  S

CGGAGCCCCCAGCAGGGCTCCACACACCCCAGGAGCTCGCCCCTGAGATCTCC                      960
 P  E  P  A  P  Q  Q  G  S  T  H  T  P  R  S  P  G  S  T  R  T  R  P  E  I  S

CAGGGCTGGGCCACGCAGGGAGAAGTGATCCCAACAGGCTCCTCGTCTCAAACCTGCGGGGTGACCAGCTG   1040
 Q  A  G  P  T  Q  G  E  V  I  P  T  G  S  S  K  P  A  G  D  Q  L  P  A  A  L  W

GACCAGCAGTGCGGCCACCCACCTCTGGACTGCTGGGCCTTGCCCTCCTGCTGCTGCTCGCCCTGGCTG    1120
 T  S  S  A  V  L  G  L  L  L  L  A  L  P  T  Y  H  L  W  K  R  C  R  H  L  A

AGGACGACACCCACCCACCAGCCTCTCTGAGGCTTCTCTGAGGCTTCTGCCCCAGTGTCGGGGTTAAGGGGACCGGCCAG   1200
 E  D  T  H  P  P  A  S  L  R  L  L  P  Q  V  S  A  W  A  G  L  R  G  T  G  Q

GTCGGGATCAGCCTCCTGAGTGGCCCAGCCTTTCCCCCTGTGAAAGCAAAATAGCTTGGACCCTTCAAGTTGAGAACT   1280
 V  G  I  S  P  S
```

FIG. 1C

GGTCAGGGCAAACCTGCCCTCCCATTCTACTCAAAGTCATCCCCTCTGCTCCACAGAGATGGATGCATGTTCTGATTGCCTCT 1360

TTGGAGAAGCTCATCAGAAACTCAAAAGAAGGCCACTGTTTGTCTCACCTACCCATGACCTGAAGCCCTCCCTGAGTGG 1440

TCCCCACCTTTCTGGACGGAACCACGTACTTTTTACATACATTGATTCATGTCTCACGTCTCCCTAAAAATGCGTAAGAC 1520

CAAGCTGTGCCCCTGACCACCCCTGGGCCCCTGTCGTCAGGACCTCCTGAGGCTTTGGCAAATAAACCTCCTAAAATGATAA 1600

AAAAAAAAAAAAAAAAAAAAAAAA 1624

FIG. 2A

```
ATGGATTTCGGACTGGCGCTCCTGCTGGCCTTCGGGCTCCTGCTGGGGCAGTCCCTCCAGGTGAAGCCCCTGCA      80
 M  D  F  G  L  A  L  L  L  A  F  G  L  L  L  G  Q  S  L  Q  V  K  P  L  Q

GGTGGAGCCCCCGGAGCCGGTGGTGGCCGTTGGGGCGTCGCTCGGCGCCAGCTCACCTGCCTGCGCTGCGCGGACC     160
 V  E  P  P  E  P  V  V  A  V  A  L  G  A  S  R  Q  L  T  C  R  L  A  C  A  D

GCGGGGCCTCGGTCGGTGCAGTGGCGCCTGGACACCAGCCTGGGCGCAGTCGACAGTGACACGGGCCGCAGCGTCCTCACC     240
 R  G  A  S  V  Q  W  R  G  L  D  T  S  L  G  A  V  Q  S  D  T  G  R  S  V  L  T

GTGCGCAACGCCTCGCTGTCGGCCGCTGGCACCCGTGTC C GTGGGCAGC C GGGGCCGCACCTTCCAGCACACCGT     320
 V  R  N  A  S  L  S  A  A  G  T  R  V  C  V  G  S  C  G  G  R  T  F  Q  H  T  V

GCAGCTCCTCCTTGTGTACGCCCTTCCCCAGCAGCGTCTCCCCAGACCCTGGTGCTCCCTGGTGACCCGGAGGTGGCCT     400
 Q  L  V  T  A  F  P  D  Q  L  T  V  S  P  A  A  L  V  P  G  D  P  E  V  A

GTACGGCCCACAAAGTCACGCCGGTGGACCCCAACGCCTCTCCCTGCTCTTCCTCCTGCTCGTCGGGGGCCAGGAACTGGAGGGG     480
 C  T  A  H  K  V  T  P  V  D  P  N  A  L  S  F  S  L  L  V  G  G  Q  E  L  E  G

GCGCAAGCCCTGGGCCCGGAGGTGCAGGAGGTGCAGGAGGAGGAGGAGCCCCAGGGGGGGACGAGGACGTGCTGTTCAGGGTGACAGA     560
 A  Q  A  L  G  P  E  V  Q  E  E  E  E  E  P  Q  G  D  E  D  V  L  F  R  V  T  E
```

FIG. 2B

```
GCGCTGGCGGCTGCCGCCCCTGTGCCCCGCCCCTACTGCCAGGCCACGATGAGGCTGCCTGGCTTGG    640
 R  W  R  L  P  P  L  G  T  P  V  P  P  A  L  Y  Q  A  T  M  R  L  P  G  L

AGCTCAGCCACCGGCCAGGCCATCCCCGTCCTGCACAGCCCCACCTCCCCGGAGCCTCCCCGGAGTCT    720
 E  L  S  H  R  Q  A  I  P  V  L  H  S  P  T  S  P  E  P  P  D  T  S  P  E  S

CCCGACACACCCTCCCCGGAGTCTCCCCGGACACACCCTCCCCAGGAGCCTCCCCGGAGCCTCCCGACAA    800
 P  D  T  S  P  E  S  P  D  T  S  P  E  S  P  D  T  S  Q  E  P  P  D  T  S  P  E  P  P  D  K

GACCTCCCCGGAGCCCGCCCCCCAGCAGCAGGGGAGCCTCCACCAGGACTCCCCAGGACTCGCCCCTG    880
 T  S  P  E  P  A  P  Q  Q  G  S  T  H  T  P  R  S  P  G  S  T  R  T  R  R  P

AGATCTCCCAGGCCGGGCCAGGACTCAGTGGGGCTGCTGCTGCTTGCCCTTATCACCTCTGAAAACGCCG    960
 E  I  S  Q  A  G  P  T  Q  G  E  V  I  P  T  G  S  S  K  P  A  G  D  Q  L  P  A

GCTCTGTGGACACCACCAGCAGTGCGGTCCTGGGCTTGCTGCTGCTTGCCCTTATCACCTCTGAAAACGCTGCCGGCA    1040
 A  L  W  T  S  S  A  V  L  G  L  L  L  L  A  L  P  T  Y  H  L  W  K  R  C  R  H

CCTGGCTGAGGACGACACACCCACCCCCGGCTTCTCTGAGGCTTGGGCCTGGGCTGTGCCAGGTGCCGGTTAAGGGGGA    1120
 L  A  E  D  D  T  H  P  P  A  S  L  R  L  L  P  Q  V  S  A  W  A  G  L  R  G
```

FIG. 2C

```
CCGGGCCAGGTGGGGATCAGCCCCTCCTGAGTGGCCAGCCTTTCCCCCTGTGAAAGCAAAATAGCTTGGACCCCTTCAAGT    1200
 T  G  Q  V  G  I  S  P  S

TGAGAACTGGTCAGGGCAAACCTGCCCTCCCATTCTACTCAAAGTCATCCCCTCTGTTCACAGAGATGGATGCATGTTCTGA    1280

TTGCCTCTTTGGAGAAGCTCATCAGAAACTCAAAAGAAGGCCACTGTGTTTGTCTCACCTACCCATGACCTGAAGCCCCTCC    1360

CTGAGTGGTCCCCACCTTTCTGGACGGAACCACGTACTTTTTACATACATTGATTCATGTCTCCACGTCTCCCCTAAAAATG    1440

CGTAAGACCAAGCTGTGCCCTGACCACCCCTGGGCCCCCTGTCGTCAGGACCTCCTGTCGTCAGGACCTTTGGCAAATAAACCTCCTAA    1520

AATGAAAAAAAAAAAAAAA    1539
```

FIG. 3A

```
AGCATGGATCGGGGATCCCTGCTCCTGGCCCTGCTGCTCCTCCAGCCGGGCTGCGGCCAGTCCCTCCAGGT    80
   M  D  R  G  L  A  L  L  L  A  G  L  L  L  Q  P  G  C  G  Q  S  L  Q  V

GAAGCCCCTGCAGGTGGAGCCCCCGTTCTTCCCGGTGGTGGCCGTCCTGGGCGCCTCTCGCCAGCTCACCTGCCGCCTGG   160
 K  P  L  Q  V  E  P  P  F  F  P  V  V  A  V  L  G  A  S  R  Q  L  T [C] R  L

ACTGCCGGGACCGGGGCGCCACCGTGCAGTGGCGCGGTGCAGTCGAGTCCAGTCTGGGCGCCGTGCAGTCGGACGCGGGCCGC   240
 D [C] A  D  R  G  A  T  V  Q  W  R  G  L  D  T  S  L  G  A  V  Q  S  D  A  G  R

AGCGTCCTCACCGTGCGCAACGCCTCGCTGAGCGCCGCCGGGACCCGCGTGTGCGTGGGCTCCTGCGGGGGCCGCACCTTT   320
 S  V  L  T  V  R  N  A  S  L  S  A  A  G  T  R  V [C] V  G  S [C] G  G  R  T  F

CCAGCACACCGTGCGGCTCCTCGTGTACGCCTTCCCCGACCAGCTGACCATCTCCCCGGCCGCCCTGGTGCCTGGTGACC   400
 Q  H  T  V  R  L  L  V  Y  A  F  P  D  Q  L  T  I  S  P  A  A  L  V  P  G  D

CGGAGGTGGCCTGTACGGCCCACAAAGTCACGCCTGTGGACCCCAATGCGCTCTCCTTCTCCCTGCTCCTGGGGACCAG   480
 P  E  V  A [C] T  A  H  K  V  T  P  V  D  P  N  A  L  S  F  S  L  L  L  G  D  Q

GAACTGGAGGGCGCCCAGGCTCTGGGGCCCGAGGTGGAGGAGGAGGAGCCCCAGGAGGAGGAGGACGTGCTGTT   560
 E  L  E  G  A  Q  A  L  G  P  E  V  E  E  E  E  E  P  Q  E  E  E  D  V  L  F
```

```
CAGGGTGACAGAGCGCTGGGCGACCCTGGCAACCCCTGTCTGCCGGCTCTACTGCCAGGCCACGATGAGGC    640
 R  V  T  E  R  W  R  L  P  T  L  A  T  P  V  I  P  A  L  Y  [C] Q  A  T  M  R

TGCCTGGCTTGGAGCTCAGCGCCACCGCCAGGCCATCCCGGTCCTGACGGCCCGAACCCTCCCGGAGCCCGACACGACC    720
 L  P  G  L  E  L  S  H  R  Q  A  I  P  V  I  H  G  P  T  S  R  E  P  P  D  T  T

TCCCCGGAAACCCCGACCTCCCCGGAGACCAGGCCTCCACACAGCCCCAGGAGCCCGGGCTC    800
 S  P  D  P  R  A  A  T  S  P  E  T  T  P  Q  C  G  S  T  R  S  P  R  S  P  G  S

TACCAGGACTTGCCGCCCCTGAGATCTCCCAGGCTCAGGGACCACGCCAGGAGAAGTGATCCCAACAGGCTCGTCCAAACCTA    880
 T  R  T  C  R  P  E  I  S  Q  A  G  P  T  Q  G  F  V  I  P  T  G  S  S  K  P

CGGGTGACCAGCTGCCCGCGGCTCTGTGGACCAGCAGTGCGGTGGTGCTGGGACTGCTCCTGCTTTGCCACCTACCAC    960
 T  G  D  Q  L  P  A  A  L  W  T  S  S  A  V  L  G  L  L  L  L  A  I  P  T  Y  H

CTCTGGAAACGTTGCCGGCACCTGGCTGAGGACGGCGCCCACCAGCTTCTCTGAGTAGCCCTTCCCCCTGTG    1040
 L  W  K  R  C  R  H  L  A  E  D  G  A  H  P  P  A  S  L  S  S  Q  P  F  P  L  .

AAGGGAAAATAGGTTGGACCCCTTCAAGCTGAGAACCTGTCGGGCAAACCTGCCTCCCATTCTATTCAAAGTCATCGCT    1120
```

FIG. 3C

```
CTGGTCACAGAGAGGACGCACATTCTGATTGCCTCCTTTGGAAAGGCTCATCAGAAACTCAAAGAAGGTGATCGTTTG      1200
TCCCGGCCTACCCGTGACCTGGAAGCCCCCGCTCGAGTGACCCCCTGACTTTCTGGACGGAACCAACGTACTTCTTA      1280
CATATATTGATTGATGTGTCATATCTCCCTAAAATGCGTAAAACCAGCTGTGCCCCGACCACCTTGGGCCCCTGCCATCA   1360
GGACCTCCTGAGGCTTTGGCAAATAAACCTCCTAAAAGGATAGAAACTGAAACTTGTGGCCGGGCGCGGTGGCTCAAGCC   1440
TGTAATCCCAGCACTTTGGGAGGCCGAGGTGGGATCACGAGGTCAGGAGATCGAGACCATCCTGGCTAACCCGTGAA     1520
ACCCCGTCTCTACTAAAAAAATACAAAAATTAGCCGGGCGCCTGTAGTCCCAGCTACTCGGGAGGCTG             1600
AGGCAGGAGAATGGGCGTGAACCCGGGAGGCGGAGCTTGCAGTGAGCTGAGATCCGGCCACTGCACTCCAGCCTGGGGAC   1680
AGAGCGAGACTCCGTCTCAAAAAAAAAAAAAAAAAAAA      1721
```

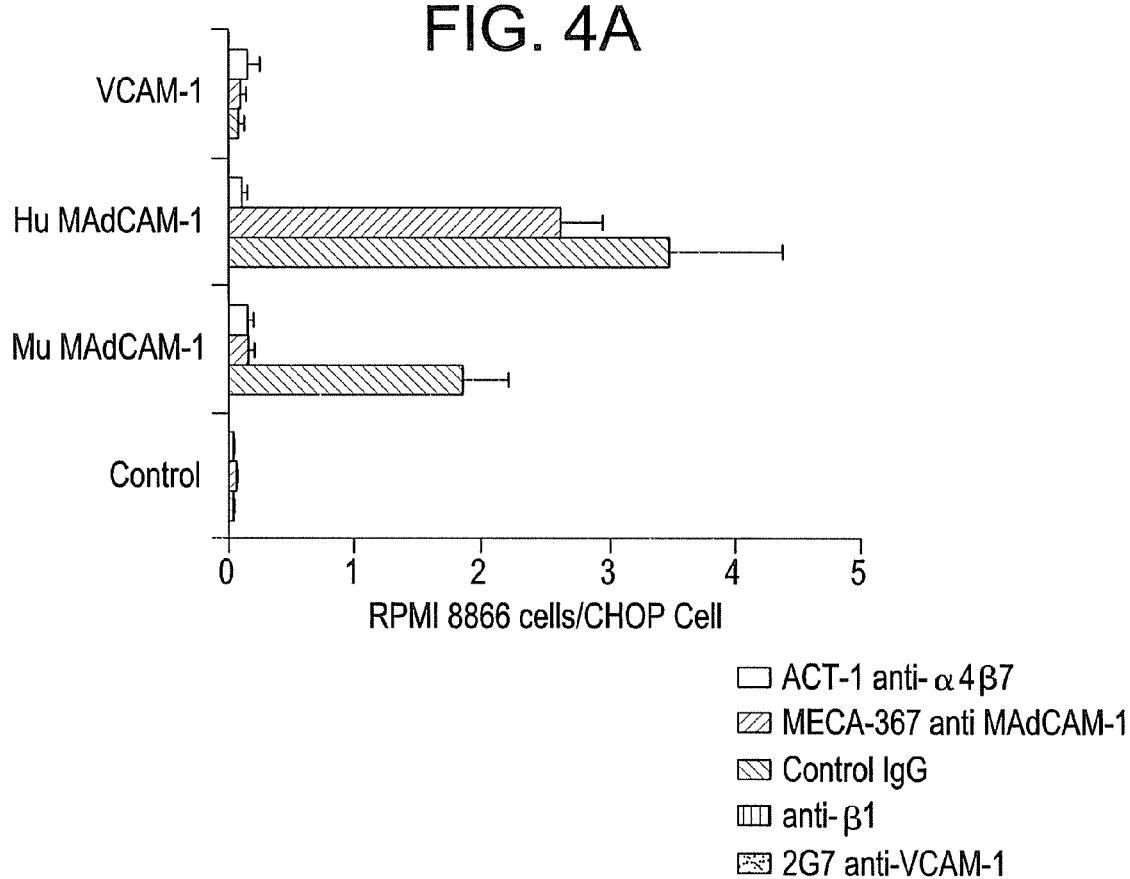
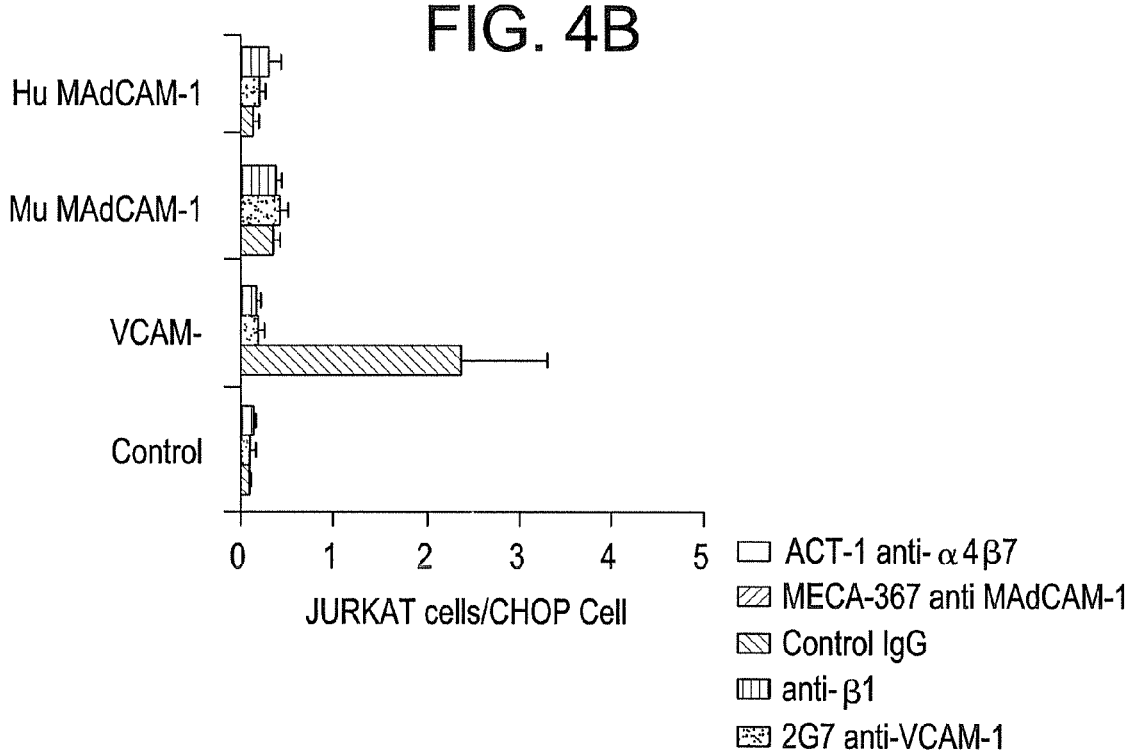

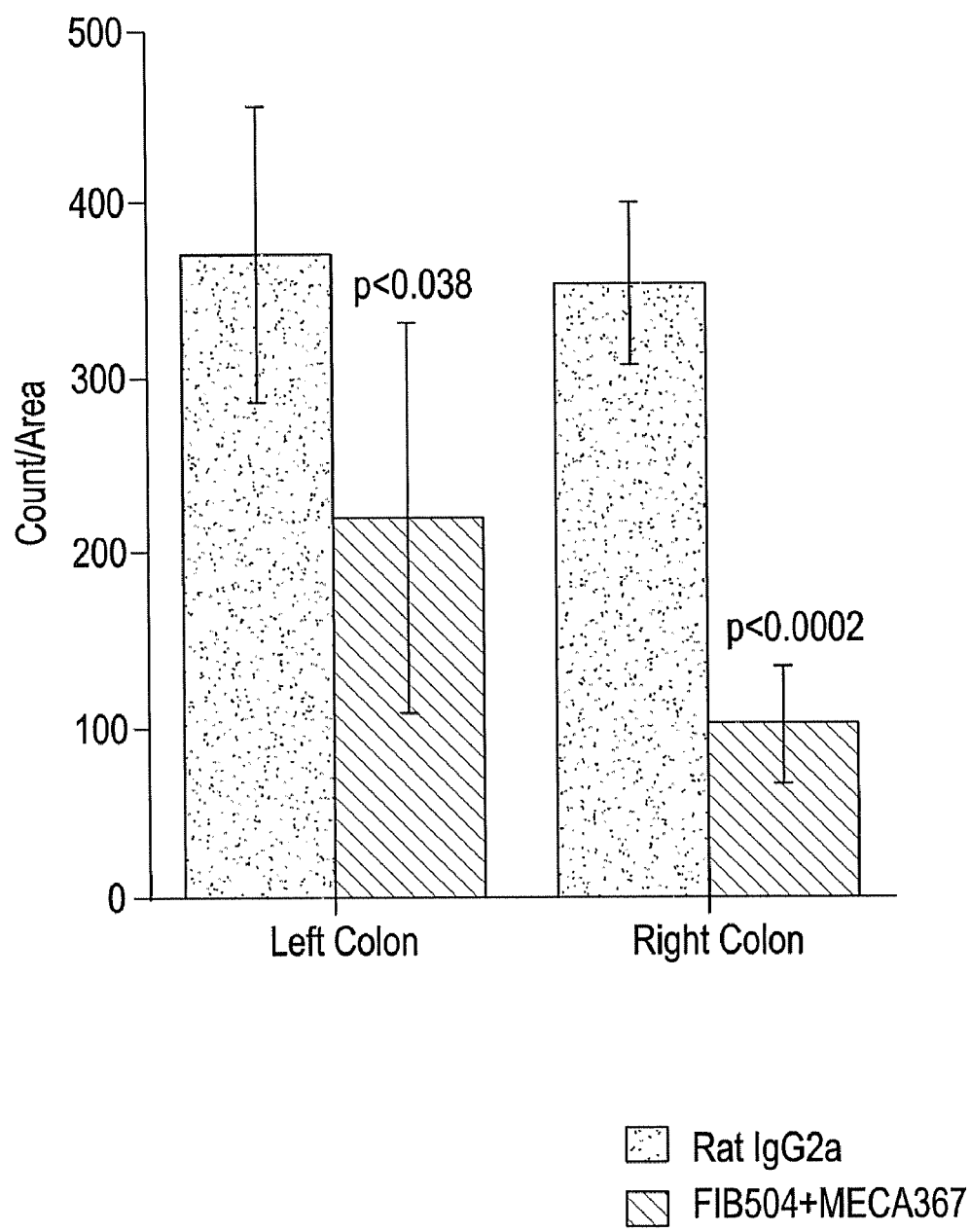

MUCOSAL VASCULAR ADDRESSING AND USES THEREOF

RELATED APPLICATIONS

This application is the U.S. National Phase of PCT/US96/02153, filed Feb. 12, 1996 and is a continuation-in-part of U.S. Ser. No. 08/523,004, filed on Sep. 1, 1995, the teachings of which are each incorporated herein by reference in their entirety.

BACKGROUND OF THE INVENTION

Lymphocyte homing from the circulation to the lymphoid tissues and migration to sites of inflammation is regulated by interaction with receptors expressed in postcapillary venules, including high endothelial venules (HEV) found in secondary lymphoid tissues (e.g., mesenteric lymph nodes, Peyer's Patches (PP)) (Bevilacqua, M. P., *Annu. Rev. Immunol.,* 11: 767-804 (1993); Butcher, E. C., *Cell,* 67: 1033-1036 (1991); Picker, L. J., et al., *Annu. Rev. Immunol.,* 10: 561-591 (1992); and Springer, T. A., *Cell,* 76: 301-314 (1994)). These interactions are tissue specific in nature.

Inflammation (e.g., chronic inflammation) is characterized by infiltration of the affected tissue by leukocytes, such as lymphocytes, lymphoblasts, and mononuclear phagocytes. The remarkable selectivity by which leukocytes preferentially migrate to various tissues during both normal circulation and inflammation results from a series of adhesive and activating events involving multiple receptor-ligand interactions as proposed by Butcher and others (Butcher, E. C., *Cell,* 67: 1033-1036 (1991); vonAdrian, U. H., et al., *Proc. Natl. Acad. Sci. USA,* 88: 7538 (1991); Mayadas, T. N., et al., *Cell,* 74: 541 (1993); Springer, T. A., *Cell,* 76: 301 (1994)). As an initial step, there is a transient, rolling interaction between leukocytes and endothelium, which results from the interaction of selectins (and by $\alpha 4$ integrins in some instances) with their carbohydrate ligands. This interaction which is characterized by rolling in the direction of flow can be assessed by known methods (Lawrence, M. B. and T. A. Springer, *Cell,* 65: 859 (1991); WO 92/21746, Springer et al., (Dec. 10, 1992)). This is followed by activation events mediated by chemoattractants such as chemokines and their receptors, which cause activation of integrin adhesiveness and influence the direction of migration of leukocytes through vascular walls. Such secondary signals in turn trigger the firm adhesion of leukocytes to endothelium via leukocyte integrins and their endothelial ligands (Ig-like receptors and the ECM), and subsequent transendothelial migration from the circulation across the vascular endothelium.

In secondary lymphoid tissues, such as Peyer's patches (PPs) and lymph nodes (e.g., peripheral lymph nodes (PLN)), leukocyte trafficking and homing is regulated by interactions of homing receptors on the surface of leukocytes with endothelial cells lining the post-capillary venules, notably high endothelial venules (HEV) (Gowans, J. L. and E. J. Knight, *Proc. R. Soc. Lond.,* 159: 257 (1964)). Receptors termed vascular addressins, which are present on the endothelial cell surface and regulate the migration and subsequent extravasation of lymphocyte subsets. The vascular addressins show restricted patterns of expression and this tissue specific expression makes an important contribution to the specificity of leukocyte trafficking (Picker, L. J. and E. C. Butcher, *Annu. Rev. Immunol.,* 10: 561-591 (1992); Berg, E. L., et al., *Cellular and molecular mechanisms of inflammation,* 2: 111 (1991); Butcher, E. C., *Cell,* 67: 1033-1036 (1991)).

Mucosal vascular addressin MAdCAM-1 (Mucosal Addressin Cell Adhesion Molecule-1) is an immunoglobulin superfamily adhesion receptor for lymphocytes, which is distinct from VCAM-1 and ICAM-1. MAdCAM-1 was identified in the mouse as a ~60 kd glycoprotein which is selectively expressed at sites of lymphocyte extravasation. In particular, MAdCAM-1 expression was reported in vascular endothelial cells of mucosal tissues, including gut-associated tissues or lymphoid organs, such as Peyer's patches and venules of the lamina propria of the small and large intestine, and the lactating mammary gland, but not in peripheral lymph nodes. MAdCAM-1 is involved in lymphocyte binding to Peyer's Patches. (Streeter, P. R., et al., *Nature,* 331: 41-46 (1988); Nakache, M., et al., *Nature,* 337: 179-181 (1989); Picker, L. J., et al., *Annu. Rev. Immunol.,* 10: 561-591 (1992); Briskin, M. J., et al., *Nature,* 363: 461 (1993); Berg, E. L., et al., *Nature,* 366: 695-698 (1993); Berlin, C., et al., *Cell,* 74: 185-195 (1993)). MAdCAM-1 can be induced in vitro by proinflammatory stimuli (Sikorski, E. E., et al., *J. Immunol.,* 151: 5239-5250 (1993)).

MAdCAM-1 specifically binds the lymphocyte integrin $\alpha 4 \beta 7$ (also referred to as LPAM-1 (mouse), $\alpha 4 \beta p$ (mouse)), which is a lymphocyte homing receptor involved in homing to Peyer's patches (Berlin, C., et al., *Cell,* 80: 413-422 (1994); Berlin, C., et al., *Cell,* 74: 185-195 (1993); and Erle, D. J., et al., *J. Immunol.,* 153: 517-528 (1994)). In contrast to VCAM-1 and fibronectin, which interact with both $\alpha 4 \beta 1$ and $\alpha 4 \beta 7$ (Berlin, C., et al., *Cell,* 74: 185-195 (1993); Strauch, U. S., et al., *Int. Immunol.,* 6: 263 (1994)), MAdCAM-1 is a selective receptor for $\alpha 4 \beta 7$.

Inflammatory bowel disease (IBD), such as ulcerative colitis and Crohn's disease, for example, can be a debilitating and progressive disease involving inflammation of the gastrointestinal tract. Affecting an estimated two million people in the United States alone, symptoms include abdominal pain, cramping, diarrhea and rectal bleeding. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *New Engl. J. Med.,* 325: 928-937 (1991) and Podolsky, *New Engl. J. Med.,* 325: 1008-1016 (1991).

Some studies have suggested that the cell adhesion molecule, ICAM-1, mediates leukocyte recruitment to inflammatory sites through adhesion to leukocyte surface ligands, i.e., Mac-1 or LFA-1 (Springer, *Nature,* 346: 425-434 (1990)). In addition, vascular cell adhesion molecule-1 (VCAM-1), which recognizes the $\alpha 4 \beta 1$ integrin (VLA-4), has been reported to play a role in in vivo leukocyte recruitment (Silber et al., *J. Clin. Invest.* 93: 1554-1563 (1994)). It has been proposed that IBD can be treated by blocking the interaction of ICAM-1 with LFA-1 or Mac-1, or of VCAM-1 with $\alpha 4 \beta 1$ (e.g., WO 93/15764). However, these therapeutic targets are likely to be involved in inflammatory processes in multiple organs, and a functional blockade could cause systemic immune dysfunction.

In contrast to VCAM-1 and ICAM-1, MAdCAM is preferentially expressed in the gastrointestinal tract, binds the $\alpha 4 \beta 7$ integrin found on lymphocytes, and participates in the homing of these cells to mucosal sites, such as Peyer's patches in the intestinal wall (Hamann et al., *Journal of Immunology,* 152: 3282-3293 (1994)). The use of inhibitors to the binding of MAdCAM to the receptor, $\alpha 4 \beta 7$, in the treatment of diseases such as IBD has not been suggested. Moreover, although human $\alpha 4$ and $\beta 7$ genes and proteins have been identified (Yuan et al., *Int. Immunol.,* 2: 1097-1108 (1990); Erle et al., *J. Biol. Chem.,* 266: 11009-11016 (1991);

Bevilacqua, M. P., *Annu. Rev. Immunol.*, 11: 767-804 (1993); Springer, T. A., *Cell,* 76: 301-314 (1994)), human or primate MAdCAM-1 has not been cloned or characterized.

SUMMARY OF THE INVENTION

The present invention relates to proteins or polypeptides, referred to herein as isolated and/or recombinant (e.g., essentially pure) primate MAdCAMs. In one embodiment, primate MAdCAM can selectively bind to cells which express the α4β7 integrin, particularly lymphocytes. The recombinant proteins of the present invention, including variants, can be produced in host cells as described herein. In addition, antibodies reactive with the proteins of the present invention can be produced using a primate MAdCAM or a variant thereof as immunogen, for example. Such antibodies or fragments thereof are useful in therapeutic, diagnostic and research applications. For example, the antibodies can be used in the purification and study of MAdCAMs, the identification of cells which express MAdCAM, and the detection or quantitation of MAdCAM in a sample.

The invention further relates to isolated and/or recombinant (e.g., essentially pure) nucleic acids which encode a primate MAdCAM, such as human MAdCAMs. In another aspect, the invention relates to recombinant nucleic acid constructs, such as plasmids or retroviral vectors, which contain a nucleic acid which encodes a protein of the present invention or portion thereof. The nucleic acids and constructs can be used to produce recombinant primate MAdCAMs. In another embodiment, the nucleic acid encodes an antisense nucleic acid which can hybridize with a second nucleic acid encoding a primate MAdCAM, and which can inhibit the expression of the protein (e.g., when introduced into cells).

Also encompassed by the present invention are methods of identifying ligands and/or inhibitors (e.g., antagonists) of MAdCAM function. For example, primate MAdCAM, including variants, can be used in assays (e.g., adhesion assays) designed to identify antagonists which block the binding of MAdCAM to the ligand, α4β7 integrin.

The invention further relates to methods of therapy, including a method of treating an individual suffering from a disease associated with leukocyte (such as lymphocyte or monocyte) recruitment to the gastrointestinal tract or other tissues as a result of binding of leukocytes to gut-associated endothelium expressing the molecule MAdCAM, comprising administering to the individual (e.g., a mammal, such as a primate) an effective amount of an agent or compound, such as an antibody, which inhibits the binding of leukocytes to endothelial MAdCAM. The antibody is preferably a monoclonal, chimeric and/or humanized antibody or an antigen binding fragment thereof, and inhibits adhesion of leukocytes expressing an integrin containing the β7 chain (such as α4β7) to endothelium expressing MAdCAM. In one embodiment, the monoclonal antibody or antigen binding fragment thereof has the antigenic specificity of a monoclonal antibody selected from the group consisting of FIB 21, FIB 30, FIB 504 and ACT-1. Inflammatory bowel diseases, such as, but not limited to, ulcerative colitis, Crohn's disease, Pouchitis, celiac disease, microscopic or collagenous colitis, and eosinophilic gastroenteritis can be treated according to the claimed method.

BRIEF DESCRIPTION OF THE DRAWINGS

FIGS. 1A-1C are an illustration of the nucleotide sequence (SEQ ID NO:1) determined from subclones of cDNA clone 4 encoding human MAdCAM-1, and the sequence of the predicted protein encoded by the open reading frame (MAdCAM-1; SEQ ID NO:2). The predicted signal peptide and transmembrane region are underlined in bold. Cysteine residues of the two Ig-like domains are boxed, as are potential N-linked glycosylation sites. The mucin domain, containing the PPDTTS(Q/P)E repeat (see e.g., amino acid residues 264-271 and 232-239, respectively, of SEQ ID NOS:1 and 2) and consisting of 71 amino acids is outlined by a thin bold line (amino acids 226-296 of SEQ ID NOS:1 and 2).

FIGS. 2A-2C are an illustration of the nucleotide sequence (SEQ ID NO:3) determined from subclones of cDNA clone 20 encoding human MAdCAM-1, and the sequence of the predicted protein encoded by the open reading frame (MAdCAM-1; SEQ ID NO:4). The predicted signal peptide and transmembrane region are underlined in bold. Cysteine residues of the two Ig-like domains are boxed, as are potential N-linked glycosylation sites. The mucin domain, containing the PPDTTS(Q/P)E identified in clone 4 (see e.g., amino acid residues 264-271 and 232-239, respectively, of SEQ ID NOS:1 and 2) and repeat consisting of 47 amino acids is outlined by a thin bold line (amino acids 226-272 of SEQ ID NOS:3 and 4).

FIGS. 3A-3C are an illustration of the nucleotide sequence (SEQ ID NO:5) determined from subclones of cDNA clone 31D encoding macaque MAdCAM-1, and the sequence of the predicted protein encoded by the open reading frame (MAdCAM-1; SEQ ID NO:6). The predicted signal peptide and transmembrane region are underlined in bold. Cysteine residues of the two Ig-like domains are boxed. The mucin domain, which contains a single copy of the PPDTTS(Q/P)E repeat identified in clone 4 (see e.g., amino acid residues 264-271 and 232-239, respectively, of SEQ ID NOS:1 and 2), is outlined by a thin bold line (amino acid residues 229-292 of SEQ ID NOS:5 and 6).

FIGS. 4A-4B are histograms illustrating the selective binding of cells transfected with human MAdCAM-1 to lymphocytes expressing α4β7. FIG. 4A illustrates the results of an experiment in which RPMI 8866 cells ($0.5 \times 10^6$/well), which express α4β7 (and not α4β1), bound to CHO/P cells expressing murine or human MAdCAM-1, but did not bind to CHO/P cells transfected with human VCAM-1 or to CHO/P cells transfected with pcDNA-3. FIG. 4B illustrates the results of an experiment in which CHO/P cells transfected with human VCAM-1 bound to Jurkat cells (which express high levels of α4β1), but failed to bind to CHO/P cells transfected with murine or human MAdCAM-1 or to CHO/P cells transfected with pcDNA-3 as a control. Binding is shown as the number of bound RPMI 8866 cells per CHO/P cell (FIG. 4A) or bound Jurkat cells per CHO/P cell (FIG. 4B) in an average of at least four fields (10× objective)±standard error. Binding reactions included control IgG, anti-α4β7 (monoclonal antibody ACT-1), or anti-murine MAdCAM-1 (monoclonal antibody MECA-367) as indicated.

FIG. 17A, media control; FIGS. 17B-17C, supernatants from cells transfected with Clone 21 (comprising the entire extracellular domain of human MAdCAM); FIGS. 17D-17E, supernatants from cells Clone 38 (comprising the two N-terminal Ig domains of human MAdCAM). Binding after preincubation of cells with media alone (at right). Binding was inhibited by preincubation of cells with anti-β7 MAb FIB 504 (at left).

FIG. 21 is a histogram illustrating the reduction in the number of CD4$^+$ T cells in the ascending (right) or descending (left) colon in scid mice treated for 14 days with a combination of FIB 504 plus MECA-367 as compared to mice treated with an isotype-matched control rat IgG2a antibody as determined by staining frozen sections of left and right colon with a rat antibody specific for mouse CD4.

DETAILED DESCRIPTION OF THE INVENTION

Proteins and Peptides

Figure 5:
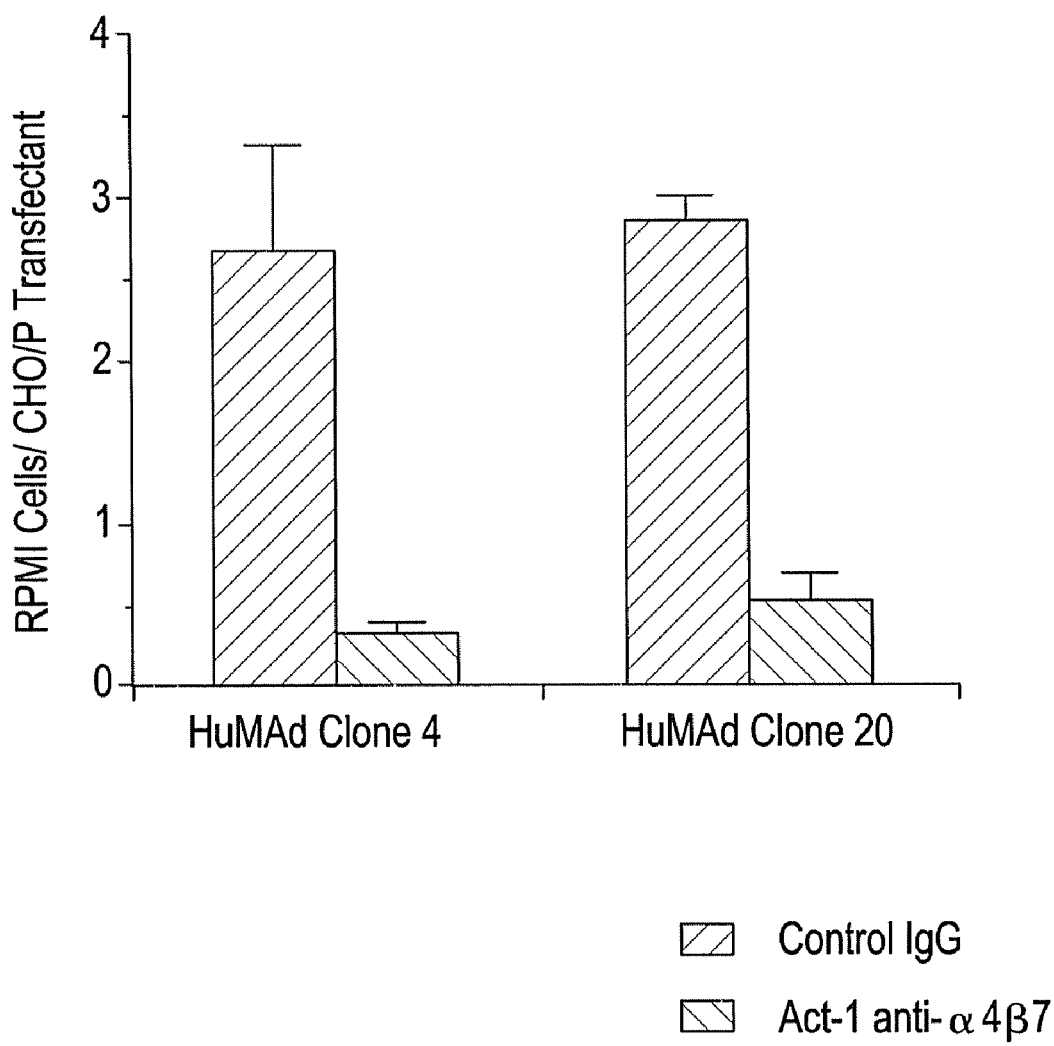
FIG. 5 is a histogram illustrating that human MAdCAM-1 encoded by clones 4 and 20 binds RPMI 8866 cells and that binding is inhibited by the ACT-1 antibody. Bars respresent an average of four fields from a single experiment with standard deviations as shown.

The present invention relates to isolated and/or recombinant (including, e.g., essentially pure) proteins or polypeptides designated primate MAdCAMs (Mucosal Addressin Cell Adhesion Molecules) and variants of primate MAdCAMs. In a preferred embodiment, the isolated and/or recombinant proteins of the present invention have at least one property, activity or function characteristic of a primate MAdCAM (as defined herein), such as binding function (e.g., the ability to bind an α4β7 integrin), and/or cellular adhesion molecule function (e.g., the ability to mediate cellular adhesion such as α4β7-dependent adhesion in vitro and/or in vivo), and/or an immunological property as defined herein. For example, some proteins of the present invention can selectively bind to an α4β7 integrin and thereby mediate α4β7-dependent cellular adhesion to cells bearing the α4β7 integrin, such as leukocytes (especially lymphocytes such as T or B cells) in vitro and/or in vivo. In one aspect, proteins of the present invention can mediate heterotypic cell adhesion (e.g., of endothelial cells to leukocytes such as lymphocytes).

In another embodiment, proteins of the present invention can bind a primate α4β7 integrin from the same or a different primate species, and/or have cellular adhesion molecule function (e.g., the ability to mediate cellular adhesion such as α4β7-dependent adhesion in vitro and/or in vivo). For example, as shown herein, human and macaque MAdCAM-1 proteins, produced in mammalian cells by expression of cDNA clones, can selectively bind to α4β7 integrin present on human lymphocytes, and can function as cellular adhesion molecules capable of mediating selective adhesion to cells bearing the α4β7 integrin.

Proteins or polypeptides referred to herein as "isolated" are proteins or polypeptides purified to a state beyond that in which they exist in mammalian cells. "Isolated" proteins or polypeptides include proteins or polypeptides obtained by methods described herein, similar methods or other suitable methods, including essentially pure proteins or polypeptides, proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, and more preferably, in essentially pure form. Proteins or polypeptides referred to herein as "recombinant" are proteins or polypeptides produced by the expression of recombinant nucleic acids.

As used herein "primate MAdCAM" refers to naturally occurring or endogenous primate MAdCAM proteins, to proteins having an amino acid sequence which is the same as that of a naturally occurring or endogenous corresponding primate MAdCAM (e.g., recombinant proteins), and to functional variants of each of the foregoing (e.g., functional fragments and/or mutants produced via mutagenesis and/or recombinant techniques). Accordingly, as defined herein, the term includes mature primate MAdCAM, glycosylated or unglycosylated MAdCAM proteins, polymorphic or allelic variants, and other isoforms of primate MAdCAM (e.g., produced by alternative splicing or other cellular processes), and functional fragments.

Naturally occurring or endogenous primate MAdCAM proteins includes wild type proteins such as mature MAdCAM, polymorphic or allelic variants and other isoforms which occur naturally in primates (e.g., humans or other non-human primates, such as macaque, cotton top tamarin). Such proteins can be recovered from a source which naturally produces primate MAdCAM. These proteins and primate MAdCAM proteins having the same amino acid sequence as a naturally occurring or endogenous corresponding primate MAdCAM, are referred to by the name of the corresponding primate. For example, where the corresponding primate is a human, the protein is designated as a human MAdCAM protein (e.g., a recombinant human MAdCAM produced in a suitable host cell).

"Functional variants" of primate MAdCAMs include functional fragments, functional mutant proteins, and/or functional fusion proteins. Generally, fragments or portions of primate MAdCAM encompassed by the present invention include those having a deletion (i.e., one or more deletions) of an amino acid (i.e., one or more amino acids) relative to the mature primate MAdCAM (such as N-terminal, C-terminal or internal deletions). Fragments or portions in which only contiguous amino acids have been deleted or in which non-contiguous amino acids have been deleted relative to mature primate MAdCAM are also envisioned.

Generally, mutants or derivatives of primate MAdCAMs, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of primate MAdCAM differing by the addition, deletion and/or substitution of one or more contiguous or non-contiguous amino acid residues.

A "functional fragment or portion", "functional mutant" and/or "functional fusion protein" of a primate MAdCAM refers to an isolated and/or recombinant protein or oligopeptide which has at least one property, activity and/or function characteristic of a primate MAdCAM, such as binding function (e.g., the ability to bind an $\alpha 4\beta 7$ integrin), and/or cellular adhesion molecule function (e.g., the ability to mediate cellular adhesion such as $\alpha 4\beta 7$-dependent adhesion in vitro and/or in vivo), and/or retains at least one immunological property of a primate MAdCAM.

As used herein, a protein, polypeptide or oligopeptide having "at least one immunological property" of a primate MAdCAM is one which (a) is bound by at least one antibody of a selected epitopic specificity which binds to a naturally occurring or endogenous primate MAdCAM or to a protein having the same amino acid seqence as the naturally occurring or endogenous primate MAdCAM (e.g., human MAdCAM-1), and/or (b) is an immunogen capable of inducing the formation in a suitable animal of an antibody of a selected epitopic specificity which binds to a naturally occurring or endogenous primate MAdCAM or to a protein having the same amino acid seqence as the naturally occurring or endogenous primate MAdCAM. For example, a suitable fragment can cross-react with an antibody which is raised against and/or reactive with isolated primate MAdCAM.

Suitable fragments or mutants can be identified by screening. For example, the N-terminal, C-terminal, or internal regions of the protein can be deleted in a step-wise fashion and the resulting protein or polypeptide can be screened using a suitable binding or adhesion assay, such as an assay described herein. Where the resulting protein displays activity in the assay, the resulting protein ("fragment") is functional. Information regarding the structure and function of murine MAdCAM and other adhesion molecules, and of primate MAdCAMs as shown herein, provides a basis for dividing primate MAdCAM into functional domains (see below).

The term variant also encompasses fusion proteins, comprising a primate MAdCAM (e.g., mature human MAdCAM-1) as a first moiety, linked to a second moiety not occurring in the primate MAdCAM as found in nature. Thus, the second moiety can be an amino acid, oligopeptide or polypeptide. The first moiety can be in an N-terminal location, C-terminal location or internal to the fusion protein. In one embodiment, the fusion protein comprises a human MAdCAM or portion thereof as the first moiety, and a second moiety comprising a linker sequence and affinity ligand (e.g., an enzyme, an antigen, epitope tag).

In another embodiment, the fusion protein is a hybrid immunoglobulin, such as a hybrid comprising a primate MAdCAM moiety fused at its C-terminus, to the N-terminus of an immunoglobulin moiety (e.g., one or more immunoglobulin constant regions, preferably of primate origin), such as those prepared according to Capon et al., U.S. Pat. Nos. 5,428,130 and 5,225,538, the teachings of which are incorporated herein by reference in their entirety). The hybrid immunoglobulin comprises a fusion protein or polypeptide containing at least a portion of an immunoglobulin chain, and preferably at least one complete immunoglobulin domain (e.g., CH1, hinge). Other examples of "immunoadhesins" have been reported (Watson, S. R., et al., *Nature,* 349: 164-167 (1991); Martin, S., et al., *J. Virol.,* 67: 3561-3568 (1993); Staunton, D. E., et al., *J. Exp. Med.,* 176: 1471-1476 (1992); Capon, D. J., et al., *Nature,* 337: 525-531 (1989); Jakubowski et al., *J. Immunol.,* 155: 938-946 (1995)). For example, a fusion protein comprising all or a portion of a primate (e.g., human) MAdCAM and an immunoglobulin heavy or light chain constant region or portion thereof can be prepared (e.g., by preparing a nucleic acid which encodes the fusion protein). Typically, the fusion is constructed such that the C-terminal end of the MAdCAM is joined to the N-terminal end of the immunoglobulin constant region. However, fusion proteins in which the N-terminal end of the MAdCAM is joined to the C-terminal end of the immunoglobulin constant region can be made. Preferably, a portion of primate MAdCAM which is sufficient for binding to a ligand (e.g., α4β7 integrin), such as the complete extracellular domain or a portion comprising the two N-terminal immunoglobulin domains in which the transmembrane region is deleted, is used (see e.g., Example 3).

A variety of hybrid immunoglobulin molecules can be produced (e.g., monomeric, homodimeric, heterodimeric, homotetrameric, heterotetrameric), depending upon the type of constant region selected and the portion used (e.g., light chain constant region, heavy chain constant region (such as γ1, γ2, γ3, γ4, α1, α2, δ, ε, and μ constant regions obtained from IgG, IgA, IgD, IgE, or IgM), and portions thereof) in the fusion polypeptide, and whether they are assembled into multimeric forms with each other and/or with other hybrid immunoglobluins or immunoglobulin chains (see Capon et al., U.S. Pat. Nos. 5,428,130 and 5,225,538). In a preferred embodiment, the fusion protein comprises a complete heavy chain constant region or at least a functionally active hinge region, CH2 and CH3 domain. A particular constant region (e.g., IgG1), variant or portions thereof can be selected to tailor effector function. For example, an mutated constant region (variant) can be incorporated into a fusion protein to minimize binding to Fc receptors (Example 3; Winter et al., GB 2,209,757 B; and Morrison et al., WO 89/07142), and/or to fix complement (WO 94/29351, Dec. 22, 1994), etc.

Examples of "primate MAdCAM" proteins include proteins encoded by a human or macaque MAdCAM-1 nucleic acid of the present invention, such as a protein having an amino acid sequence as set forth or substantially as set forth in FIG. 1 (SEQ ID NO:2), FIG. 2 (SEQ ID NO:4) or FIG. 3 (SEQ ID NO:6), and functional portions thereof. In a preferred embodiment, a primate MAdCAM or variant has an amino acid sequence which is at least about 55% similar, more preferably at least about 75% similar, and still more preferably at least about 90% similar, to a protein shown in FIG. 1 (SEQ ID NO:2), FIG. 2 (SEQ ID NO:4) or FIG. 3 (SEQ ID NO:6).

MAdCAM Structure

Figure 6:
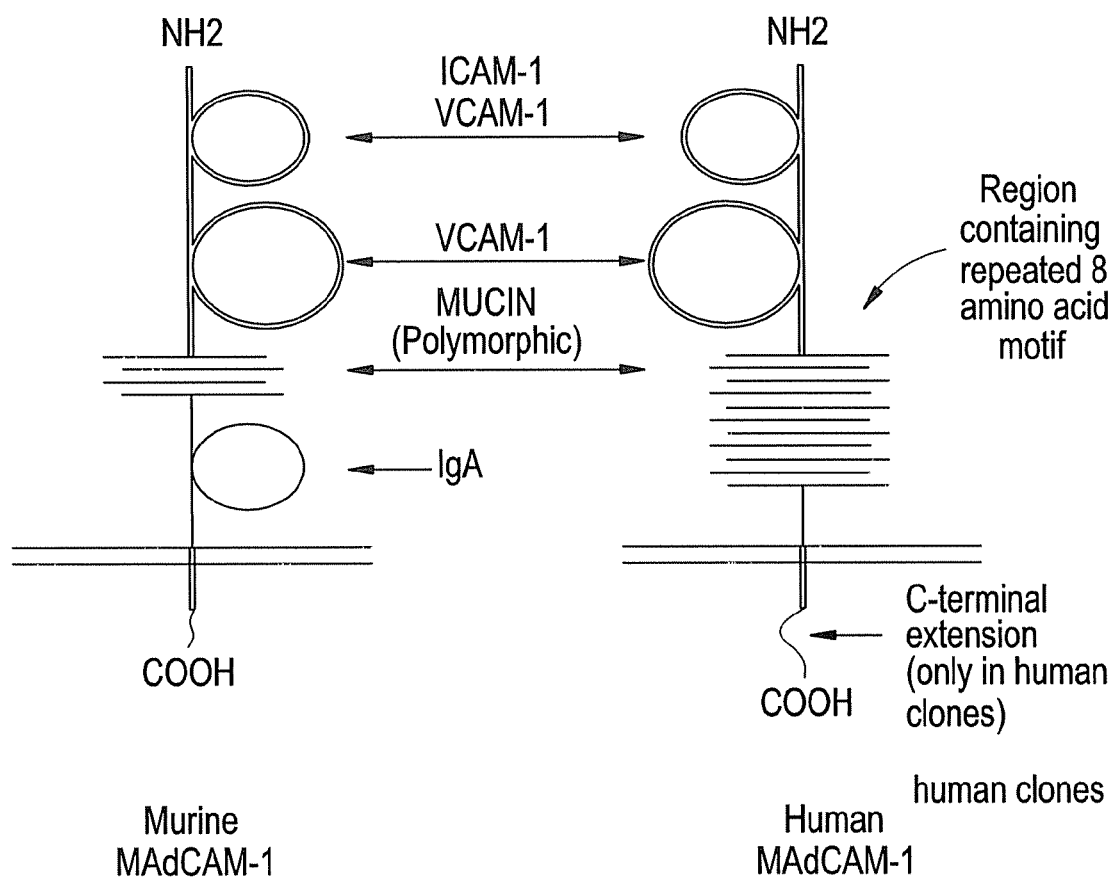
FIG. 6 is an illustration of the deduced domain structures of murine and human MAdCAM-1. The two N-terminal immunoglobulin domains bounded by disulfide bonds (indicated by loops) implicated in cell adhesion, transmembrane regions and a cytoplasmic tail are present in murine, macaque and human proteins. Human MAdCAM-1 has a longer cytoplasmic tail. An eight-amino acid repeat found in the mucin domain is present in 4 or 8 copies in human isoforms, but appears only once in the murine and macaque.

Murine MAdCAM-1, a member of the immunoglobulin supergene family, is a multi-domain molecule, comprising both immunoglobulin-related and mucin-like sequences (Briskin, M. J., et al., *Nature,* 363:461 (1993)). As indicated in FIG. 6, the murine form contains two amino-terminal immunoglobulin-like domains are homologous to domains of the Ig-like adhesion receptors, ICAM-1 and VCAM-1, and are implicated in integrin binding. The third (membrane proximal) immunoglobulin-like domain, while unrelated to adhesion receptors of this class, shares homology with another mucosal-related immunoglobulin superfamily member, IgA. In addition to the three immunoglobulin-like domains, murine MAdCAM-1 has a serine/threonine-rich mucin-like domain between the second and third Ig-like domains. These structural elements suggest that MAdCAM-1 facilitates more than one function in cell adhesion cascades, and recent studies of murine MAdCAM-1 support a role for MAdCAM-1 in both selectin and integrin binding (Moore, K. L., et al., *J. Cell. Biol.,* 118:445 (1992); Bargatze, R. F., et al., *Immunity,* 3:99-108 (1995)). Also in this regard, it has been reported that murine MAdCAM-1, when expressed in mesenteric lymph nodes can present L-selectin binding carbohydrates associated with the peripheral node addressin epitope, MECA-79 (Berg, E. L., et al., *Nature,* 366:695 (1993)).

As described herein human and macaque MAdCAM-1 proteins have two immunoglobulin-like (Ig-like) domains which are homologous to the two amino-terminal immunoglobulin-like integrin binding domains of murine MAdCAM-1 (FIGS. 1-3, and 6). However, the similarity of sequences within the region homologous to the mucin/IgA domain of murine MAdCAM-1 is much less apparent. The membrane proximal regions of the human and macaque receptors exhibit considerable variation (as compared with each other or murine MAdCAM-1) with respect to the length of the mucin-like sequence and the lack of a membrane proximal Ig (IgA like) domain.

Two isoforms of human MAdCAM-1 have been identified which exhibited single amino acid polymorphisms and variation in the number of copies of a serine/threonine/proline rich repeat in the mucin region. These two isoforms appear to be encoded in genomic DNA, suggesting allelic variation and/or alternative processing of this sequence. These two isoforms may serve as alternative mechanisms of regulating α4β7 binding affinity and/or presenting carbohydrates for selectin binding. The presence of these Ig-like and mucin domains in primate MAdCAMs described herein is also consistent with role in selectin as well as integrin binding.

Recent domain swapping experiments in murine MAdCAM-1 have shown that, although domain one of MAdCAM-1 can weakly bind α4β7, adhesion is poor in the absence of strong integrin activation. The two amino-terminal Ig-like domains (which are similar to domains of ICAM-1 and VCAM-1) are sufficient for α4β7 binding activity in an activation independent manner comparable to that of wild type murine MAdCAM-1.

A short motif (GLDTSL) (SEQ ID NO:14) present in domain one of murine MAdCAM-1, is conserved and required for integrin binding in other Ig-like adhesion receptors, including of domain one of ICAM-1, ICAM-2, and ICAM-3, and domains 1 and 4 of VCAM-1 (Staunton, D. E., *Cell,* 52: 925-33 (1988); Staunton, D. E., et al., *Nature,* 339: 61 (1989); Osborn, L., et al., *Cell,* 59:1203 (1989); Fawcett, J., et al., *Nature,* 360:481 (1992)). This sequence, G-(I/L)-(D/E)-(T/S)-(P/S)-L (SEQ ID NO:15), is located between β sheets c and d of these integrin binding domains. The GLDTSL (SEQ ID NO:14) motif was found in the primate MAdCAMs characterized here.

Mutagenesis of E34 (Glu$^{34}$) in this motif of domain 1 of ICAM-1 (underlined above) and of D40 (Asp$^{40}$) in VCAM-1 (in bold face above) had profound effects on binding of LFA-1 and α4β1, respectively (Osborn, L., et al., *J. Cell. Biol,* 124:601-608 (1994); Renz, M. E., et al., *J. Cell. Biol.,* 125: 1395-1406 (1994); Staunton, D. E., et al., *Cell,* 61:243-254 (1990); Vonderheide, R. H., et al., *J. Cell. Biol.,* 125:215-222 (1994)). More recently, a fragment of VCAM-1 comprising the two N-terminal domains was subjected to crystallographic structure determination (Jones, E. Y., et al., *Nature,* 373:539-544 (1995); Wang, J-H, et al., *Proc. Natl. Acad. Sci. USA.,* 92:5714-5718 (1995)). The conserved motif in VCAM-1 (QIDSPL) (SEQ ID NO:16) appears to be highly exposed on the N-terminal portion of the CD loop of the first Ig domain in a position that appears to be readily accessible to integrins.

A nucleotide substitution in this motif of murine MAdCAM-1, resulting in a change at amino acid 61 from leucine to arginine (L61→R61), abolishes MAdCAM-1 interactions with resting lymphocytes expressing α4β7. Therefore, murine MAdCAM-1 also requires this conserved amino acid motif, GLDTSL (SEQ ID NO:14), within the computer predicted CD loop of its N-terminal domain for binding its integrin ligand, α4β7.

Comparisons of human MAdCAM cDNA clones 4 and 20 (FIGS. 1 and 2) revealed that the amino-terminal 225 amino acids are identical in clones 4 and 20. This region comprises a predicted 18 amino acid hydrophobic leader or signal sequence, and two immunoglobulin-like domains. This region can be aligned with primate and murine MAdCAM-1, and displays the following conserved features: (1) a predicted signal peptide (identical in the human proteins, and similar to the macaque and murine signal peptides); (2) two pairs of cysteine residues in the first Ig-like domain, the cysteines of each pair being separated by 3 amino acids; (3) a sequence of nine amino acids (which contains the "LDTSL" motif (SEQ ID NO:17)) in the predicted C-D loop of Ig-like domain 1, and is implicated as a general integrin recognition site (identical in each primate clone); and (4) an uncharacteristically large second immunoglobulin-like domain. The size of the second Ig-like domain, with approximately 70 amino acids between cysteine residues would classify it as a "V" (variable) type domain, in contrast with the C2 type (constant) domains which are more typically found in the Ig-like adhesion receptors (Hunkapiller, T., et al., *Adv. in Immunol.*, 44:1-62 (1989); Williams, A. F., et al., *Annu. Rev. Immunol.*, 6:381-405 (1988)). Within this domain is an extended C'-E loop containing an abundance of negatively charged residues, which is common to each primate, murine and human MAdCAM-1 clone characterized, but which is not seen in related adhesion receptors.

The next region found in clones 4 and 20 is analogous to the mucin domain of murine MAdCAM-1, due to a prevalence of serine, threonine and proline (69% for clone 4 and 76% for clone 20) residues (boxed in FIG. 1 and FIG. 2). This region, although similar in amino acid composition to murine MAd-CAM-1, is highly divergent from murine MAdCAM-1. Therefore, selection for conservation of the integrin binding Ig-like domains appears greater than that of the mucin sequences. The human MAdCAM-1 domain is 71 amino acids long in clone 4, and 47 amino acids long in clone 20. This region also contains two polymorphisms: (1) a polymorphism at amino acid 240, which is proline (P) in clone 4 and serine (S) in clone 20; and (2) a polymorphism at amino acid 242, which is asparagine (N) in clone 4 and aspartate (D) in clone 20. In addition, the human mucin domains contain a repeat of 8 amino acids consisting of the sequence PPDTTS (Q/P)E (see e.g. amino acid residues 264-271 and 232-239, respectively, of SEQ ID NOS:1 and 2), which appears eight times in clone 4 and five times in clone 20.

Since the human mucin domain is highly repetitive, truncation of three repeats in clone 20 relative to clone 4 could be the result of processes such as alternative splicing or mutation (e.g., an aberrant recombination event) that maintain the reading frame, yielding a receptor that is functional with respect to integrin binding, and suggesting that some or all of the mucin sequences are dispensable for integrin binding. Consistently, it has been shown that Ig-like domains 1 and 2 of murine MAdCAM-1 are sufficient for activation-independent adhesion to α4β7, indicating that murine mucin sequences are dispensable for integrin binding. Also of interest in this regard, the macaque clone which was isolated lacks most of the repeat region.

The remaining C-terminal 110 amino acids are identical between clones 4 and 20: 47 amino acids precede a predicted hydrophobic transmembrane segment of 20 amino acids, which is followed by a cytoplasmic tail of 43 amino acids. The 47 amino acids immediately C-terminal to the mucin region are in a region corresponding to the IgA-like Ig domain of murine MAdCAM-1. Although the human and macaque proteins are similar in this region, they are divergent from murine MAdCAM-1. Compared with murine MAdCAM-1, the human proteins are 59 amino acids shorter in this region, and lack any characteristics of an Ig-like domain. The transmembrane domains of all the receptors are similar, but the cytoplasmic tail is considerably longer (43 amino acids) in human (26 in primate and 20 in the mouse) MAdCAM-1.

Method of Producing Recombinant Proteins

Another aspect of the invention relates to a method of producing a primate MAdCAM or variant (e.g., portion) thereof. Recombinant protein can be obtained, for example, by the expression of a recombinant DNA molecule encoding a primate MAdCAM or variant thereof in a suitable host cell, for example.

Constructs suitable for the expression of a primate MAdCAM or variant thereof are also provided. The constructs can be introduced into a suitable host cell, and cells which express a recombinant primate MAdCAM or variant thereof, can be produced and maintained in culture. Such cells are useful for a variety of purposes, and can be used in adhesion assays (e.g., in an assay to screen for ligands and/or candidate inhibitors of MAdCAM-mediated adhesion), in the production of protein for characterization, isolation and/or purification, (e.g., affinity purification), and as immunogens, for instance. Suitable host cells can be procaryotic, including bacterial cells such as *E. coli, B. subtilis* and or other suitable bacteria, or eucaryotic, such as fungal or yeast cells (e.g., *Pichia pastoris*, Aspergillus species, *Saccharomyces cerevisiae, Schizosaccharomyces pombe, Neurospora crassa*), or other lower eucaryotic cells, and cells of higher eucaryotes such as those from insects (e.g., Sf9 insect cells) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)). In one embodiment, host cells capable of expressing membrane-bound mature protein are used. In another embodiment, host cells capable of secreting a soluble MAdCAM (e.g., soluble MAdCAM, such as MAdCAM lacking the C-terminal transmembrane region and cytoplasmic tail).

Host cells which produce a recombinant primate MAdCAM or variants thereof can be produced as follows. For example, a nucleic acid encoding all or part of the coding sequence for the desired protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

The transcriptional and/or translational signals of a a MAd-CAM-1 gene can be used to direct expression. Alternatively, suitable expression vectors for the expression of a nucleic acid encoding all or part of the coding sequence of the desired protein are available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting or secretion (of primate origin or from a heterologous primate or non-primate species). In a construct, a signal sequence can be provided by the vector, the primate MAdCAM coding sequence, or other source.

A promoter is provided for expression in a suitable host cell. Promoters can be constitutive or inducible. In the vectors, the promoter is operably linked to a nucleic acid encoding the primate MAdCAM or variant thereof, and is capable of directing expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a primate MAdCAM or variant thereof can be incorporated into the vector, operably linked to one or more expression control elements, and the construct can be introduced into host cells which are maintained under conditions suitable for expression, whereby the encoded polypeptide is produced. The construct can be introduced into cells by a method appropriate to the host cell selected (e.g., transformation, transfection, electroporation, infection). For production of a protein, host cells comprising the construct are maintained under conditions appropriate for expression, (e.g., in the presence of inducer, suitable media supplemented with appropriate salts, growth factors, antibiotic, nutritional supplements, etc.). The encoded protein (e.g., human MAdCAM-1) can be isolated from the host cells or medium.

Fusion proteins can also be produced in this manner. For example, some embodiments can be produced by the insertion of a primate MAdCAM cDNA or portion thereof into a suitable expression vector, such as Bluescript®II SK+/− (Stratagene), pGEX-4T-2 (Pharmacia), pcDNA-3 (Invitrogen) and pET-15b (Novagen). The resulting construct is then introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1-16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

Nucleic Acids, Constructs and Vectors

The present invention relates to isolated and/or recombinant (including, e.g., essentially pure) nucleic acids having sequences which encode a primate MAdCAM or variant thereof as described herein.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated (see e.g., Daugherty, B. L. et al., *Nucleic Acids Res.,* 19(9):2471-2476 (1991); Lewis, A. P. and J. S. Crowe, *Gene,* 101: 297-302 (1991)). Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid or portion thereof encodes a protein or polypeptide having at least one property, activity or function characteristic of a primate MAdCAM (as defined herein), such as binding function (e.g., the ability to bind an α4β7 integrin), and/or cellular adhesion molecule function (e.g., the ability to mediate cellular adhesion such as α4β7-dependent adhesion in vitro and/or in vivo), and/or an immunological property as defined herein.

The present invention also relates more specifically to isolated and/or recombinant nucleic acids or a portion thereof having sequences which encode human or macaque MAdCAM-1 or variants thereof.

The invention further relates to isolated and/or recombinant nucleic acids that are characterized by:
(1) their ability to hybridize to (a) a nucleic acid encoding a primate MAdCAM, such as a nucleic acid having a nucleotide sequence as set forth or substantially as set forth in FIG. 1 (SEQ ID NO:1), FIG. 2 (SEQ ID NO:3), or FIG. 3 (SEQ ID NO:5); (b) the complement of any one of (a); or (c) portions of either of the foregoing (e.g., a portion comprising the open reading frame); or
(2) by their ability to encode a polypeptide having the amino acid sequence of a primate MAdCAM (e.g., SEQ ID NO:2, SEQ ID NO:4, or SEQ ID NO:6); or
(3) by both characteristics.

In one embodiment, the nucleic acid shares at least about 50% nucleotide sequence similarity to any one of the nucleotide sequences shown in FIG. 1, FIG. 2, or FIG. 3 (SEQ ID NO:1, 3, or 5, respectively) or to one of the MAdCAM coding regions thereof. More preferably, the nucleic acid shares at least about 75% nucleotide sequence similarity, and still more preferably, at least about 90% nucleotide sequence similarity, to any one of the sequences shown in FIG. 1, FIG. 2, or FIG. 3 (SEQ ID NO:1, 3, or 5, respectively) or to one of the MAdCAM coding regions thereof.

Isolated and/or recombinant nucleic acids meeting these criteria comprise nucleic acids having sequences identical to sequences of naturally occurring primate MAdCAMs or variants of the naturally occurring sequences. Such variants include mutants differing by the addition, deletion or substitution of one or more residues, modified nucleic acids in which one or more residues are modified (e.g., DNA or RNA analogs), and mutants comprising one or more modified residues.

Nucleic acids of the present invention, including those which hybridize to a selected nucleic acid as described above, can be detected or isolated under high stringency conditions or moderate stringency conditions, for example. "High stringency conditions" and "moderate stringency conditions" for nucleic acid hybridizations are explained at pages 2.10.1-2.10.16 (see particularly 2.10.8-11) and pages 6.3.1-6 in *Current Protocols in Molecular Biology* (Ausubel, F. M. et al., eds., Vol. 1, Suppl. 26, 1991), the teachings of which are hereby incorporated by reference. Factors such as probe length, base composition, percent mismatch between the hybridizing sequences, temperature and ionic strength influence the stability of nucleic acid hybrids. Thus, high or moderate stringency conditions can be determined empirically, and depend in part upon the characteristics of the known nucleic acid (e.g., DNA) and the other nucleic acids to be assessed for hybridization thereto.

Isolated and/or recombinant nucleic acids that are characterized by their ability to hybridize (e.g. under high or moderate stringency conditions) to (a) a nucleic acid encoding a primate MAdCAM (for example, those nucleic acids depicted in FIG. 1 (SEQ ID NO:1), FIG. 2 (SEQ ID NO:3), and FIG. 3 (SEQ ID NO:5), (b) the complement of such nucleic acids, (c) or a portion thereof, can also encode a protein or polypeptide having at least one property, activity or function characteristic of a primate MAdCAM (as defined herein), such as binding function (e.g., the ability to bind an α4β7 integrin), and/or cellular adhesion molecule function (e.g., the ability to mediate cellular adhesion such as α4β7-dependent adhesion in vitro and/or in vivo), and/or an immunological property as defined herein. Preferred nucleic acids have lengths of at least about 40 nucleotides, more preferably at least about 50, and still more preferably at least about 75 nucleotides.

The binding function of a primate MAdCAM or variant thereof which is encoded by a nucleic acid of the present invention can be detected by standard assays for ligand binding (e.g., assays which monitor formation of a complex between isolated and/or recombinant MAdCAM and an α4β7 integrin) or standard adhesion assays (e.g., in which adhesion between a first cell expressing a recombinant primate MAdCAM, and a second cell bearing an α4β7 integrin is monitored), or other suitable methods. Binding and/or adhesion assays or other suitable methods can also be used in procedures for the identification and/or isolation of nucleic acids which encode a polypeptide of the present invention (see e.g., Example 1). The antigenic properties of proteins or polypeptides encoded by nucleic acids of the present invention can be determined by immunological methods employing antibodies that bind to a primate MAdCAM, such as immunoblotting, immunoprecipitation and immunoassay (e.g., radioimmunoassay, ELISA).

Nucleic acids of the present invention can be used in the production of proteins or polypeptides. For example, a nucleic acid (e.g., DNA) encoding a primate MAdCAM can be incorporated into various constructs and vectors created for further manipulation of sequences or for production of the encoded polypeptide in suitable host cells as described above.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the top strand shown in FIG. 1 (SEQ ID NO:1), FIG. 2 (SEQ ID NO:3), or FIG. 3 (SEQ ID NO:5). For example, antisense nucleic acid can be complementary to a target nucleic acid having the sequence shown as the top strand of the open reading frame in FIG. 1 (SEQ ID NO:1), FIG. 2 (SEQ ID NO:3), or FIG. 3 (SEQ ID NO:5), or to a portion thereof sufficient to allow hybridization. In another embodiment, the antisense nucleic acid is wholly or partially complementary to and can hybridize with a target nucleic acid which encodes a primate MAdCAM.

The nucleic acids can also be used as probes (e.g., in in situ hybridization) to assess associations between inflammatory bowel disease (IBD) (or other conditions) and increased expression of primate MAdCAM in affected tissues. The nucleic acids can also be used as probes to detect and/or isolate (e.g., by hybridization with RNA or DNA) polymorphic or allelic variants, for example, in a sample (e.g., inflamed tissue) obtained from a primate. Moreover, the presence or frequency of a particular variant in a sample(s) obtained from one or more affected primates, as compared with a sample(s) from normal primate(s), can be indicative of an association between inflammatory bowel disease (IBD) (or other conditions) and a particular variant, which in turn can be used in the diagnosis of the condition.

As described in the Examples, a cDNA clone encoding macaque MAdCAM-1 was isolated by expression cloning, and the cDNA was used as a probe to screen a human cDNA library. Two distinct nucleic acids encoding human MAdCAM-1 were isolated and characterized. Additional human, macaque or other primate genes or cDNAs can be obtained. For example, the genes described here, or sufficient portions thereof, whether isolated and/or recombinant or synthetic, can be used as probes or primers to detect and/or recover additional nucleic acids encoding primate MAdCAMs or variants thereof from a suitable source such as a primate genomic or cDNA library, according to methods described herein or other suitable methods (e.g., by hybridization, PCR, expression cloning or other suitable techniques).

In one embodiment, nucleic acids encoding primate MAdCAM are producible by methods such as PCR amplification. For example, appropriate primers (e.g., a pair of primers or nested primers) can be designed which comprise a sequence which is complementary or substantially complementary to a portion of a primate MAdCAM cDNA described herein. For instance, primers complementary to the 5'- or 3'-ends of the coding sequence and/or flanking the coding sequence can be designed. Such primers can be used in a polymerase chain reaction with a suitable template nucleic acid to obtain nucleic acid encoding primate MAdCAM, for example. Suitable templates include e.g., constructs described herein (such as pcD3PMAd, pcD3HuMAd-4 or pcD3HuMAd-20), a cDNA library or another suitable source of primate (e.g., human) cDNA or genomic DNA. Primers can contain portions complementary to flanking sequences of the construct selected as template as appropriate.

Additional genes or cDNAs can be used to express primate MAdCAM, with utilities corresponding to those described herein, and can be used in the production of constructs, host cells, and antibodies using methods described herein. The approaches described herein, including, but not limited to, the approaches used to isolate and manipulate macaque and human MAdCAM-1, to construct vectors and host strains, and to produce and use the proteins, to produce antibodies, etc., can be applied to other primates.

Therapeutic Methods and Compositions

The present invention also provides antibodies which (1) can bind a "primate MAdCAM" in vitro and/or in vivo; and/or (2) can inhibit an activity or function characteristic of a "primate MAdCAM", such as binding function (e.g., the ability to bind an α4β7 integrin) and/or cellular adhesion molecule function (e.g., the ability to mediate cellular adhesion such as α4β7-dependent adhesion in vitro and/or in vivo). Such antibodies include antibodies which can bind a human or macaque MAdCAM encoded by cDNA clone 4, cDNA clone 20 or cDNA clone 31D. Also encompassed are antibodies which can bind a naturally occurring or endogenous primate MAdCAM (e.g., human MAdCAM). Preferably the antibodies are capable of selective binding of primate MAdCAM in vitro and/or in vivo (e.g., bind selectively to primate MAdCAM expressed in mucosal tissue and/or spleen (e.g., as assessed immunohistologically)).

In one embodiment, the antibodies can bind primate MAdCAM and inhibit binding of "primate MAdCAM" to an α4β7 integrin (e.g., human), thereby inhibiting cellular adhesion mediated by MAdCAM, preferably selectively. Such an antibody can inhibit α4β7-dependent cellular adhesion to cells bearing an α4β7 integrin, such as leukocytes (especially lymphocytes such as T or B cells) in vitro and/or in vivo. For example, eleven hybridomas were identified which produced antibodies which specifically inhibit the adhesion of RPMI 8866 cells to MAdCAM-1 (Example 2, hybridomas designated 10G4, 8C1, 10G3, 9G12, 9E4, 7H12, 10F2, 10A6, 1E5, 2F5, 7G11). Thus, antibodies which can inhibit cellular adhesion of cells bearing an α4β7 integrin to vascular endothelial cells in mucosal tissues, including gut-associated tissues or lymphoid organs are encompassed by the antibodies of the present invention.

Preferably, the antibodies can bind a primate MAdCAM with high affinity (for example, a Ka in the range of about 1-10 nM, or a Kd in the range of about $1 \times 10^{-8}$ to $1 \times 10^{-10}$ mol$^{-1}$).

The antibodies of the present invention are useful in a variety of applications, including processes, research, diagnostic and therapeutic applications. For instance, they can be used to isolate and/or purify primate MAdCAM or variants thereof (e.g., by affinity purification or other suitable methods), and to study MAdCAM structure (e.g., conformation) and function.

The antibodies of the present invention can also be used to modulate MAdCAM function in diagnostic (e.g., in vitro) or therapeutic applications. For instance, antibodies can act as inhibitors of to inhibit (reduce or prevent) binding function and/or cellular adhesion molecule function of a primate MAdCAM as described herein.

In addition, antibodies of the present invention can be used to detect and/or measure the level of a primate MAdCAM in a sample (e.g., tissues or body fluids, such as an inflammatory exudate, blood, serum, bowel fluid, or on cells transfected with a nucleic acid of the present invention). For example, a sample (e.g., tissue and/or fluid) can be obtained from a primate and a suitable immunological method can be used to detect and/or measure primate MAdCAM levels, including methods such as enzyme-linked immunosorbent assays (ELISA), including chemiluminescence assays, radioimmunoassay, and immunohistology. In one embodiment, a method of detecting a selected primate MadCAM in a sample is provided, comprising contacting a sample with an antibody which binds an isolated primate MAdCAM under conditions suitable for specific binding of said antibody to the selected primate MAdCAM, and detecting antibody-MAdCAM complexes which are formed.

In an application of the method, antibodies reactive with a primate MAdCAM-1 can be used to analyze normal versus inflamed tissues in human and non-human primates for primate MAdCAM reactivity and/or expression (e.g., immunohistologically). Thus, the antibodies of the present invention permit immunological methods of assessment of expression of primate (e.g., human MAdCAM-1) in normal versus inflamed tissues, through which the presence of disease, disease progress and/or the efficacy of anti-primate MAdCAM-1 therapy in inflammatory disease can be assessed.

The present invention also provides "primate MAdCAM" as defined herein, including functional variants, such as soluble primate MAdCAM (e.g., lacking the all or part of the transmembrane region and cytoplasmic tail, such that the protein secreted) and functional fusion proteins (e.g., hybrid immunoglobulins comprising a primate MAdCAM moiety fused at its C-terminus, to the N-terminus of an immunoglobulin moiety). These molecules are useful in a variety of applications, including processes, research, diagnostic and therapeutic applications.

For example, primate MAdCAM, MAdCAM-Ig fusion proteins or other recombinant soluble primate MAdCAM molecules can be used in assays to identify ligands or inhibitors (e.g., a blocking antibody) of primate MAdCAM:α4β7 interaction. As used herein, an inhibitor is a compound which inhibits (reduces or prevents) the binding of primate MAdCAM-1 to a ligand, including α4β7 integrin, and/or which inhibits the triggering of a cellular response mediated by the ligand. An effective amount is an amount sufficient to achieve inhibition of binding or adhesion to primate MAdCAM-1 and/or signalling (e.g., an amount sufficient to inhibit adhesion of a cell bearing a primate MAdCAM-1 ligand (including α4β7 integrins, such as human α4β7 integrin, and its primate homologs)) to isolated/and or recombinant primate MAdCAM.

In one aspect, a method of detecting or identifying a ligand of primate MAdCAM or an agent which binds a primate MadCAM is provided, in which an (i.e., one or more) agent to be tested (or a candidate ligand) is contacted with an isolated and/or recombinant "primate MAdCAM", including "functional variants", as defined herein under conditions suitable for binding of ligand thereto, and the formation of a complex between said agent and primate MAdCAM is detected. In one embodiment, an agent to be tested is combined with a host cell expressing recombinant primate MAdCAM or a functional variant under conditions suitable for binding of ligand thereto. In one embodiment, the primate MAdCAM or functional variant is labeled with a suitable label (e.g., fluorescent label, isotope label), and binding is determined by detection of the label. Specificity of binding can be assessed by competition or displacement, for example, using unlabeled agent, an unlabeled isolated and/or recombinant primate MAdCAM or functional variant, or a second ligand of primate MAdCAM as competitor.

In another aspect, a method of detecting an inhibitor of cellular adhesion mediated by primate MAdCAM is provided. In one embodiment, an agent to be tested is combined with a ligand of primate MAdCAM, and an isolated and/or recombinant primate MAdCAM or functional variant (e.g., fusion protein) under conditions suitable for binding of ligand thereto. The formation of a complex between the ligand and primate MAdCAM or the functional variant is monitored. A decrease in binding of ligand in the presence of the agent relative to a suitable control (e.g., binding in the absence of agent) is indicative that the agent is an inhibitor. For example, the fusion proteins and assays described in Example 3 can be used to detect inhibitors. An agent to be tested can also be combined with a first cell expressing a recombinant primate MAdCAM, and a second cell bearing an α4β7 integrin under conditions suitable for adhesion of said first cell to said second cell. Adhesion between said first and second cells can be monitored, and decreased adhesion (reduced or abolished) as compared with a suitable control is indicative that the agent is an inhibitor. A cell or cells which naturally express a ligand for MAdCAM-1, such as a leukocyte (e.g., an α4β7+ B lymphocyte, T lymphocyte) or other cell which expresses a ligand for MAdCAM-1 (e.g., a recombinant cell) can be used.

Assays such as those described in Example 3 can be used to identify compounds which inhibit binding in vitro. As shown herein, fusion proteins comprising a primate MAdCAM moiety (two chimeric MAdCAM-Ig fusions) can bind to α4β7 positive lymphocytes in solution. Thus, primate MAdCAM, including functional variants, particularly soluble primate MAdCAM molecules and fusion proteins such as the chimeric MAdCAM-Ig fusions described in Example 3, provide candidate inhibitors of α4β7:MAdCAM interaction and of in vivo lymphocyte recruitment to inflammatory sites, which can be useful in therapy as described hereinbelow. The in vivo efficacy of these molecules can be assessed using methods described herein (see e.g., Examples 4 and 5) or other suitable methods. For example, primate models such as those described in Example 5 can be used. The CD45RB$^{Hi}$/SCID model provides a mouse model with similarity to both Crohn's disease and ulcerative colitis (Example 4, Powrie, F. et al., *Immunity,* 1: 553-562 (1994)). Efficacy in this model can be assessed using an experimental protocol similar to the one used for monoclonal antibodies (Example 4). Parameters such as inhibition of recruitment of $^{111}$In-labeled cells to the colon and reduction in the number of CD4+ T lymphocytes in the lamina propria of the large intestine after administration (e.g., intravenous (i.v.), intraperitoneally (i.p.) and per oral (p.o.)) can be assessed. Knockout mice which develop intestinal lesions similar to those of human inflammatory bowel disease have also been described (Strober, W. and Ehrhardt, R. O., *Cell,* 75: 203-205 (1993)), and NOD mice provide an animal model of insulin-dependent diabetes mellitus.

The invention further relates to the discovery that diseases associated with leukocyte recruitment to the gastrointestinal tract, such as IBD, or other mucosal tissues can be treated by inhibiting MAdCAM binding to the α4β7 integrin and/or triggering of α4β7-mediated cellular responses. Compounds or agents which inhibit binding include "primate MAdCAM" as defined herein, including soluble primate MAdCAM molecules and fusion proteins, as well as antibodies or antigen binding fragments thereof which bind MAdCAM and/or the α4β7 integrin. Antibodies which can be used in the method include recombinant or non-recombinant polyclonal, monoclonal, chimeric, humanized and/or anti-idiotypic antibodies.

Monoclonal antibodies that bind MAdCAM or α4β7 have been described. For example, MECA-367 is an anti-MAdCAM antibody of the IgG2a subtype and is described in Gallatin et al., *Nature,* 304: 30 (1983) and Michie et al., *Am. J. Pathol.,* 143: 1688-1698 (1993). ACT-1 is a monoclonal antibody which binds the α4β7 integrin (Lazarovits et al., *J. Immunol.,* 133: 1857 (1984); Schweighoffer et al., *J. Immunol.,* 151: 717-729 (1993)). FIB 21 binds the β7 chain is described and characterized in Berlin et al., *Cell,* 74: 184-195 (1993); Andrew, D. P. et al., *J. Immunol.,* 153: 3847-3861 (1994)).

Other polyclonal or monoclonal antibodies, such as antibodies which bind to the same or similar epitopes as the antibodies described above, can be made according to methods described herein, methods known in the art or other suitable methods (such as Kohler et al., *Nature,* 256:495-497 (1975), Harlow et al., 1988, Antibodies: A Laboratory Manual, (Cold Spring Harbor, N.Y.) or Current Protocols in Molecular Biology, Vol. 2 (Supplement 27, Summer '94), Ausubel et al., Eds. (John Wiley & Sons: New York, N.Y.), Chapter 11 (1991)). Antibodies can also be produced which can compete with any one of the antibodies produced by the hybridoma cell lines designated 10G4, 8C1, 10G3, 9G12, 9E4, 7H12, 10F2, 10A6, 1E5, 2F5, or 7G11 for binding to a cell bearing an α4β7 integrin, preferably human α4β7 integrin.

For example, antibodies can be raised against an appropriate immunogen in a suitable mammal (e.g., a mouse, rat, rabbit or sheep). Immunogens include, for example, MAdCAM, α4β7, or immunogenic fragments thereof. For example, aprimate MAdCAM or a variant thereof can be produced and used as an immunogen to raise antibodies in a suitable immunization protocol.

Antibody-producing cells (e.g., a lymphocyte) can be isolated from, for example, the lymph nodes or spleen of an immunized animal. The cells can then be fused to a suitable immortalized cell (e.g., a myeloma cell line), thereby forming a hybridoma. Fused cells can be isolated employing selective culturing techniques. Cells which produce antibodies with the desired specificity can be selected by a suitable assay (e.g., ELISA) (see e.g., Example 2).

In one embodiment, the immunogen can be an antibody which binds, for example, MAdCAM, α4β7, or immunogenic fragments thereof. The antibody raised thereby can be an anti-idiotypic antibody, which can also be used in the present invention (U.S. Pat. No. 4,699,880).

Single chain antibodies, and chimeric, humanized or primatized (CDR-grafted or resurfaced, such as, according to EP 0,592,406; Padlan et al., Apr. 13, 1994) antibodies, as well as chimeric or CDR-grafted single chain antibodies, comprising portions derived from different species, can also be used in the invention. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., *BioTechnology,* 10:1455-1460 (1992), regarding primatized antibody, and Ladner et al., U.S. Pat. No. 4,946,778 and Bird, R. E. et al., *Science,* 242:423-426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function of the full-length antibody from which they are derived and, preferably, retain the ability to inhibit interaction. For example, antibody fragments capable of binding to the α4β7 integrin, MAdCAM or portion thereof include, but are not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

Antibodies and antigen binding fragments thereof which can be used in the claimed method include antibodies which bind to MAdCAM and/or α4β7, such as anti-β7 chain antibodies. For example, antibodies from the group including FIB 21, FIB 30, FIB 504 and ACT-1 and mixtures thereof can be administered. Alternatively or in addition, antigen fragments of these antibodies can be administered.

Compounds or agents which inhibit the binding of MAdCAM and the α4β7 integrin can be administered according to the claimed method in the treatment of diseases associated with leukocyte (e.g., lymphocyte, monocyte) infiltration of tissues (including recruitment and/or accumulation of leukocytes in tissues) which express the molecule MAdCAM-1. An effective amount of a compound or agent (i.e., one or more) is administered to an individual (e.g., a mammal, such as a human or other primate) in order to treat such a disease. For example, inflammatory diseases, including diseases which are associated with leukocyte infiltration of the gastrointestinal tract (including gut-associated endothelium), other mucosal tissues, or tissues expressing the molecule MAdCAM-1 (e.g., gut-associated tissues, such as venules of the lamina propria of the small and large intestine; and mammary gland (e.g., lactating mammary gland)), can be treated according to the present method. Similarly, an individual having a disease associated with leukocyte infiltration of tissues as a result of binding of leukocytes to cells (e.g., endothelial cells) expressing the molecule MAdCAM-1 can be treated according to the present invention.

In a particularly preferred embodiment, diseases which can be treated accordingly include inflammatory bowel disease (IBD), such as ulcerative colitis, Crohn's disease, ileitis, Celiac disease, nontropical Sprue, enteropathy associated with seronegative arthropathies, microscopic or collagenous colitis, eosinophilic gastroenteritis, or pouchitis resulting after proctocolectomy, and ileoanal anastomosis.

Pancreatitis and insulin-dependent diabetes mellitus are other diseases which can be treated using the present method. It has been reported that MAdCAM-1 is expressed by some vessels in the exocrine pancreas from NOD (nonobese diabetic) mice, as well as from BALB/c and SJL mice. Expression of MAdCAM-1 was reportedly induced on endothelium in inflamed islets of the pancreas of the NOD mouse, and MAdCAM-1 was the predominant addressin expressed by NOD islet endothelium at early stages of insulitis (Hanninen, A., et al., *J. Clin. Invest.*, 92: 2509-2515 (1993)). Further, accumulation of lymphocytes expressing α4β7 within islets was observed, and MAdCAM-1 was implicated in the binding of lymphoma cells via α4β7 to vessels from inflamed islets (Hanninen, A., et al., *J. Clin. Invest.*, 92: 2509-2515 (1993)).

Examples of inflammatory diseases associated with mucosal tissues which can be treated according to the present method include mastitis (mammary gland), cholecystitis, cholangitis or pericholangitis (bile duct and surrounding tissue of the liver), chronic bronchitis, chronic sinusitis, asthma, and graft versus host disease (e.g., in the gastrointestinal tract). As seen in Crohn's disease, inflammation often extends beyond the mucosal surface, accordingly chronic inflammatory diseases of the lung which result in interstitial fibrosis, such as hypersensitivity pneumonitis, collagen diseases, sarcoidosis, and other idiopathic conditions can be amenable to treatment.

The compound is administered in an effective amount which inhibits binding of MAdCAM to the α4β7 integrin. For therapy, an effective amount will be sufficient to achieve the desired therapeutic and/or prophylactic effect (such as an amount sufficient to reduce or prevent MAdCAM-mediated binding and/or signalling, thereby inhibiting leukocyte adhesion and infiltration and/or associated cellular responses). The compounds can be administered in a single dose or multiple doses. The dosage can be determined by methods known in the art and is dependent, for example, upon the individual's age, sensitivity, tolerance and overall well-being. Suitable dosages for antibodies can be from 0.1-1.0 mg/kg body weight per treatment.

According to the method, a compound or agent can be administered to an individual (e.g., a human) alone or in conjunction with another agent. A compound or agent can be administered before, along with or subsequent to administration of the additional agent. In one embodiment, more than one monoclonal antibody which inhibits the binding of leukocytes to endothelial MAdCAM is administered. Alternatively, a monoclonal antibody which inhibits the binding of leukocytes to endothelial ligands is administered in addition to an anti-MAdCAM or anti-β7 antibody. For example, an antibody that inhibits the binding of leukocytes to an endothelial ligand other than MAdCAM, such as an anti-ICAM-1 or anti-VCAM-1 antibody can also be administered. In another embodiment, an additional pharmacologically active ingredient (e.g., sulfasalazine, an antiinflammatory compound, or a steroidal or other non-steroidal antiinflammatory compound) can be administered in conjunction with the compound or agent (e.g., the antibody of the present invention).

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound can be solubilized and loaded into a suitable dispenser for administration (e.g., an atomizer, nebulizer or pressurized aerosol dispenser).

EXEMPLIFICATION

The present invention will now be illustrated by the following Examples, which are not intended to be limiting in any way.

Introduction

Hybridization studies using zoo blots with murine MAdCAM DNA probes under low stringency conditions indicated that nucleotide conservation between murine MAdCAM-1 and higher species was poor. A functional expression approach was used to clone primate and human homologs, whereby cells transfected with cDNAs which conferred the ability to adhere to a target lymphocyte cell line expressing high levels of the MAdCAM-1 ligand (α4β7) were identified and the cDNAs recovered. As human tissue sources were scarce, a primate homolog of MAdCAM-1 was first identified.

For expression cloning, a primate cDNA expression library, derived from mesenteric lymph nodes of a macaque, was made in a eukaryotic expression vector pRSVsport (from Gibco/BRL). A high efficiency transfection system using the CHO/P cell line (Heffernan, M. and J. D. Dennis, *Nucleic Acids Res.*, 19: 85-92 (1991)) was used. The library was separated and individual pools (representing approximately 1,500 clones) were transfected in wells of 24 well tissue culture plates. Cell adhesion assays were performed to identify cDNAs which conferred an adhesive phenotype on T and B cell lines expressing the α4β7 integrin, a known ligand for MAdCAM-1. Adhesion was identified microscopically by rosetting of the T and B cell lines on the transfected cells. A pool conferring the desired phenotype was subfractionated until a single full-length cDNA clone designated clone 31D was identified. DNA sequencing of the amino-terminal portion of the cDNA revealed homology of the macaque clone to murine MAdCAM-1 (Briskin, M. J., et al, *Nature (Lond.)*, 363:461-464 (1993)) at both the protein and nucleic acid level.

When introduced into CHO/P cells by transient transfection, the cDNA insert obtained from clone 31D directed the expression of a protein which could mediate binding to two cell lines which express α4β7: (1) TK1, a murine T cell lymphoma (Butcher, E. C., et al., *Eur. J. of Immunol.*, 10: 556-561 (1980)); and (2) RPMI 8866, a human B cell lymphoma (Erle, D. J., et al., *J. Immunol.*, 153: 517-528 (1994)). Binding of TK1 cells to cells transfected with the macaque cDNA could be blocked by antibodies to either the α4 (MAb PS/2) or the β7 (MAb FIB 504) integrins, and binding of RPMI 8866 to CHO/P cells transiently transfected with macaque cDNA (clone 31D in pSV-SPORT) was blocked by the anti-α4β7 MAb, ACT-1. In control experiments, a cDNA encoding human VCAM-1 failed to bind the RPMI 8866 human B cell line. Jurkat cells, a T cell line which expresses α4β1 and not α4β7, was shown to bind VCAM-1, but failed to bind transfectants expressing macaque cDNA.

The cDNA encoding a primate (macaque) homolog of murine MAdCAM-1 was used as a probe to obtain a clone encoding a human homolog by hybridization. To obtain a human MAdCAM-1 clone, two cDNA libraries, one derived from histologically normal human mesenteric lymph node (MLN) and one derived from an inflamed MLN lymph node from a patient with Crohn's disease, were constructed in the λZiplox phage vector from Gibco/BRL. cDNA from the macaque clone was used to screen these libraries. Two different human cDNA clones of similar size were isolated. These clones each appeared to be full-length by preliminary sequence analysis. Analysis of human, as well as macaque, MAdCAM-1 cDNAs indicates that each of the encoded proteins has a predicted hydrophobic leader sequence (underlined in FIGS. 1-3), with the remaining portions of the proteins corresponding to predicted mature human or macaque MAdCAM-1, respectively.

To assess function, the human cDNA inserts were subcloned into the pCDNA3 expression vector (Invitrogen) and transient expression assays were used to demonstrate function. The human cDNAs can be expressed as functional proteins, and are capable of mediating specific binding to cells expressing α4β7. Accordingly, these two human cDNA clones are designated as human MAdCAM-1 cDNAs.

Stable transfectants of both the primate and human cDNAs were generated in a mouse pre-B cell line, L1-2 and CHO cells. L1-2 transfectants were used to immunize mice and generate monoclonal antibodies against human MAdCAM-1. Antibodies capable of inhibiting the interaction between MAdCAM-1 and α4β7 were identified. The production of blocking antibodies directed against human MAdCAM-1 is a significant advance, as previous attempts to produce such blocking antibodies having cross-reactivity with the human homolog using murine MAdCAM-1 have failed.

Example 1

Cloning of Macaque and Human MAdCAM-1 cDNAs

RNA Isolation and Selection of Message

Total RNA was isolated from (a) primate (macaque) mesenteric lymph nodes (MLN); (b) histologically normal human mesenteric lymph nodes; (c) human mesenteric lymph nodes (inflamed ileal nodes) from a patient with Crohn's disease; and (d) tissue culture cells by use of the CsTFA™ (cesium trifluoroacetate) reagent (Pharmacia; Cat. #17-087-02). Total RNA from mesenteric lymph node was obtained from two species of macaque (*Macaca fascicularis*, and *Macaca mulatta*), and was combined prior to isolation of poly-A RNA. Tissue was first snap frozen in liquid nitrogen and subjected to dounce homogenization in a solution consisting of 5.5 M guanidinium isothiocyanate, 25 mM sodium citrate, 0.5% sodium laurel sarcosine and 0.2 M 2-mercaptoethanol, while tissue culture cells ($1\text{-}5\times10^8$) were washed once in phosphate buffered saline (PBS) and homogenized by pipetting. A clarified lysate was then layered on a cushion of CsTFA and total RNA was pelleted by centrifugation for 20 hours at 30,000 RPM.

mRNA was selected by the polyATract mRNA isolation system from Promega. The system uses a biotinylated oligo (dT) primer to hybridize (in solution) to poly A tails of eukaryotic messages. The hybrids were captured and washed at high stringency using streptavidin coupled to paramagnetic particles and a magnetic separation stand. mRNA was selected by a single purification in this system and the yields ranged from 1-2% of the total RNA yield. The integrity of both the total and mRNA was analyzed by gel electrophoresis and ethidium bromide staining.

cDNA Synthesis cDNA was synthesized using the Superscript™ lambda system (Cat. #18256-016) in conjunction with either the λZiplox™ vector (Gibco/BRL, Gaithersburg, Md., Cat. #19643-014) in the case of the human libraries, or the pSV-SPORT-1 vector (Gibco/BRL, Cat. #15388-010) in the case of the macaque library. The following modifications from the standard protocol were made. cDNA was labeled only in the first or second strand (but not both) with $\alpha^{32}$P-dCTP and estimates of quantity were made by inspection of ethidium bromide staining of aliquots of cDNA fractions.

DNA Sequencing

The entire macaque and human MAdCAM-1 cDNAs were first isolated in the library vectors pSV-SPORT-1 and pZL1 (rescued from λZiplox™), respectively. Based on restriction mapping, fragments were subcloned into Bluescript® vectors (Stratagene) to facilitate sequencing from internal regions of the cDNAs. After sequence analysis of these clones, oligonucleotide primers were made to complete the sequence. Overlapping sequence of both strands was obtained. Sequence analysis utilized the Sequenase™ 7-deaza-dGTP DNA sequencing kit with sequenase version 2.0 T7 DNA polymerase (United States Biochemical) and $^{35}$S-dCTP (Amersham Life Science and New England Nuclear). The delta TAQ seqeuncing kit (USB) and gamma $^{32}$P-ATP (Amersham) G-C rich sequence were also used for G-C rich sequences.

Sequences were entered and analyzed using the Lasergene system (DNASTAR, Inc.). Nucleotide sequence alignments were performed by the Clustal method with Weighted residue weight table, using a gap penalty of 10 and a gap length penalty of 10, and default parameters (Pairwise alignment parameters were: ktuple=2, gap penalty=5, window=4, and diagonals saved=4).

Amino acid sequence alignments were performed by the Clustal method with the PAM250 residue weight table, using a gap penalty of 10 and a gap length penalty of 10 and default parameters (Pairwise alignment parameters were: ktuple=1, gap penalty=3, window=4, and diagonals saved=5).

Preparation of Macaque Expression Library

The size fractionation procedure was also modified slightly for construction of the macaque expression library to ensure large (>1.5 kb) inserts. After one round of fractionation, only the first (largest) fraction of cDNA was saved and the remaining fractions were pooled and subjected to a subsequent round of fractionation. The top fraction from the next round was pooled with the top fraction from the previous round and the second fraction from this round was also used. These two fractions were precipitated and put into ligations with the pSV-SPORT-1 vector and a fraction of each ligation was transformed into electrocompetent DH10B bacteria (Gibco) to estimate both the titer of the library and the average insert size. Estimates from ligation of only top largest cDNA fraction revealed the potential of making up 2.4 million independent clones with an average insert size of 1.9 kb and a median size of 2 kb.

The actual library screened consisted of 150,000 independent clones which were plated at a density of 1,500 clones/plate on 100 LB agar plates (to generate 100 pools of 1,500 clones/pool) with ampicillin at 50 µg/ml and grown overnight at 37° C. For purification of individual pools, each plate was overlayed with approximately 2 ml of Luria broth (LB), and the colonies were scraped off of each plate with a standard tissue culture cell scraper, and bacterial suspensions were transferred to microfuge tubes. Prior to purification, a glycerol stock was generated from each pool. Plasmid DNAs were purified using QIAprep spin columns (QIAGEN) according to manufacturer's instructions.

Transfections

CHO/P cells (Heffernan, M. and J. D. Dennis, *Nucleic Acids Res.*, 19:85-92 (1991)) were seeded into 24 well plates approximately 24 hours prior to transfection at a density of 40,000 cells/well. DNAs were transiently transfected using the LipofectAMINE™ reagent (GIBCO; Cat. #18324-012), essentially following the recommended protocol with further optimization for 24-well plates as follows: 200 ng of DNA (representing either a plasmid pool or purified control DNAs) was diluted to 20 µl with Opti-MEM 1 reduced serum media (GIBCO) and diluted into 20 µl of a mixture that consists of 18 µl Opti-MEM 1 and 2 µl of LipofectAMINE™ reagent. This liposome mixture was then incubated for approximately 30 minutes at ambient temperature after which, 200 µl of Opti-MEM 1 was added, and the entire mixture was then overlayed onto a well of CHO/P cells and returned to the incubator. After a 2.5 hour incubation at 37° C., 240 µl of MEM-α (Gibco) media with 20% fetal calf serum (FCS) was added to each well, and the cells were incubated for an additional 18-24 hours at 37° C. The media was then changed to standard MEM-α with 10% FCS, and the adhesion assay was performed approximately 20-24 hours later.

Adhesion Assays for Expression Cloning

For the adhesion assays in the expression cloning screen, the murine T cell lymphoma TK1 which expresses high levels of α4β7 (Butcher, E. C., et al., *Eur. J. Immunol.*, 10: 556-561 (1980)) was used to detect CHO/P cells transfected with cDNAs capable of conferring an adhesive phenotype. TK1 cells were resuspended at a density of $2 \times 10^6$/ml in an assay buffer which consisted of HBSS (Hanks Balanced Salt Solution, without $Ca^{2+}$ or $Mg^{2+}$), supplemented with 2% bovine calf serum, 20 mM HEPES, pH 7.3, 2 mM $Mg^{2+}$, and 2 mM $Ca^{2+}$. Each well transfected with a DNA pool was preincubated with 0.25 ml of a combined supernatant containing monoclonal antibodies to both human VCAM-1 (MAb 2G7; Graber, N. T., et al., *J. Immunol.*, 145:819-830 (1990)) and murine MAdCAM-1 (MAb MECA-367; American Type Culture Collection (Rockville, Md.), Accession No. HB9478; Streeter, P. R., et al., *Nature*, 331:41 (1988)); see also, U.S. Pat. No. 5,403,919 to Butcher) in order to eliminate adhesion mediated by VCAM-1 (which is expressed at high levels in primate lymph nodes) or any potential contaminating murine MAdCAM-1 expression plasmids. After incubation at 4° C. for 15 minutes, 0.25 ml of the TK1 cell suspension ($5 \times 10^5$ TK1 cells) was added to each well, and incubation on a rocking platform was continued for an additional 30 minutes at 4° C. Plates were washed by gently inverting in a large beaker of phosphate buffered saline (PBS) followed by inversion in a beaker of PBS with 1.5% gluteraldehyde for fixation for a minimum of 1 hour. Wells were then examined microscopically (10× objective) for rosetting of TK1 cells.

Purification of Macaque Clones

Pools yielding one or more TK1 rosettes were further subfractionated by the following protocol: DNA representative of a positive pool was retransformed into DH10B and plated on ninety-six 100 mm petri dishes at a density of approximately 200 colonies/plate. Nitrocellulose filters were used to generate replica plates, and one set of each plate was then subjected to DNA purification and subsequent adhesion assays as described above. A replica plate representative of a positive pool was then further subfractionated into pools of 5 colonies, which were replica plated and grown overnight in LB media containing ampicillin. After one more round of DNA purification and adhesion assays, individual clones could then be grown up and the clones conferring adhesion of the TK1 cells were identified.

A full-length clone which was shown to encode MAdCAM-1 was obtained and designated clone 31D. Clone 31D, constructed in pSV-SPORT-1 (P25), contains a 5'-SalI to NotI-3' cDNA insert. Transformants of *E. coli* strain DH10B containing clone 31D were obtained. For expression in stable cell lines, this cDNA was subcloned into expression vector pcDNA-3 (Invitrogen), which carries a neo resistance gene suitable for G418 selection. In particular, insert of clone 31D was released by digestion with EcoRI (5') and NotI, and inserted into pcDNA-3 which had been cleaved with EcoRI and NotI to obtain pcD3pMAd.

Results

A cDNA expression library, divided into pools of 1,500 independent clones, was constructed from mRNA purified from macaque mesenteric lymph nodes (MLNs). Each pool was transiently transfected into the CHO/P cell line, and 48 hours after transfection, a cell adhesion assay was performed using the murine T cell lymphoma TK1. As VCAM-1 is expressed in MLNs, assays were done in the presence of anti-VCAM-1 MAb 2G7 (Graber, N. T., et al., *J. Immunol.*, 145:819-830 (1990)). Additionally, assays were performed at 4° C. in order to eliminate adhesion mediated by ICAM cDNAs (TK1 cells express high levels of LFA-1 and LFA-1 is not functional at 4° C.). Microscopic examination of the assays revealed several wells with noticeable resetting of TK1 cells. Two wells were chosen for further analysis by repeating the transfection and determining whether the binding mediated by the pools could be blocked by anti-β7 or anti-α4 MAbs. TK1 binding to one of the pools was completely inhibited by pre-incubation of TK1 cells with either anti-α4

MAb PS/2 or anti-β7 MAb FIB 504. This pool was subjected to three rounds of subfractionation until a single clone, called 31D, was isolated. Purified clone 31D mediated TK1 cell binding which could be inhibited by anti-α4 or anti-β7 antibodies.

The insert size of clone 31D was approximately 1.8 kb. Sequencing of the amino-terminus revealed several features consistent with a primate homolog of murine MAdCAM-1. The signal peptides were both 21 amino acids in length. Although the amino acid similarity was found to be only 48%, identity was 71% if non-conservative substitutions were considered. In addition, the protein encoded by clone 31D had a characteristic unique to Ig-family adhesion receptors: two pairs of cysteines separated by 3-4 (3 in this case) amino acids in the first immunoglobulin domain. Finally, 8 amino acids C-terminal to the first double cysteines is a stretch of 9 amino acids that is identical to a sequence in murine MAdCAM-1. Within this region was the sequence LDTSL (SEQ ID NO:17), which aligns with a consensus motif for integrin/Ig family member interactions. Although this motif has general conservation with respect to other Ig adhesion receptors such as ICAM-1, ICAM-2, ICAM-3 and VCAM-1 (Osborn, L., et al., *J. Cell. Biol*, 124:601-608 (1994); Renz, M. E., et al., *J. Cell. Biol.*, 125:1395-1406 (1994)), this exact sequence was previously found only in murine MAdCAM-1. The functional significance of this motif is suggested by the fact that a point mutation which changes the first L (leucine) of the motif at amino acid 61 to an R (arginine) in murine MAdCAM-1 had a dramatic effect on MAdCAM-1: α4β7 binding (not shown). The results of the functional studies together with these sequence characteristics indicate that clone 31D encodes a primate homolog to murine MAdCAM-1.

Screening of a Human Phage Library and Purification of Human Clones

Human phage cDNA libraries were constructed in the λZiplox™ vector (Gibco/BRL). Human cDNA was made from RNA isolated from either normal or inflamed mesenteric lymph nodes (MLN) as described above. cDNA was synthesized as described above, ligated into the phage vector, and titered on bacterial strain Y1090 (ZL) ("ZL"=Ziplox). Duplicate filters from approximately 500,000 independent clones (50,000 clones/filter) from both the normal and the Crohn's MLN phage libraries were screened with $^{32}$P-labeled full-length macaque MAdCAM-1 cDNA.

To prepare the probe, a ~1.7 kb EcoRI-NotI fragment was excised from clone 31D, and isolated using GeneClean (BIO 101). The fragment was labeled with α$^{32}$P-dCTP by priming with random hexamers (Maniatis et al., In: Moleculer Cloning (Cold Spring Harbor Laboratory, Cold Spring Harbor, N.Y., 1990)).

Screening conditions were as follows: 50,000 phage clones were plated on 150 mm petri dishes containing NZYCM agar (Gibco/BRL). After incubation ranging from 7-16 hours, the plates were overlaid with 132 mm nitrocellulose filters (Schleicher and Schuell, Keene, N.H.) for 2 minutes and then five minutes to transfer first and second (duplicate) lifts of phage clones, respectively. Filters were then soaked for 5 minutes in denaturing solution (1.5 M sodium chloride, 0.5 N sodium hydroxide) followed by neutralization in 1.5 M sodium chloride, 0.5 M Tris-HCl, pH 7.5. Filters were air dried for 15 minutes and then baked under vacum for 2 hours at 80° C.

Filters were pre-hybridized for 2 hours at 55° C. in 2M Na$_2$HPO$_4$, 0.5% SDS, 5×Denhardt's (1×Denhardt's solution is 0.02% bovine serum albumin, 0.02% ficoll, and 0.02% polyvinyl-pyrolidone), 1 mM EDTA, and 50 µg/ml denatured salmon sperm DNA, and subsequently hybridized overnight at 55° C. in the same buffer. Filters were washed once at room temperature in 2×SSC, 0.1% SDS (1×SSC is 0.15 M sodium chloride, 0.015 M sodium citrate), followed by three to four washes at 65° C. in 0.1×SSC and 0.1% SDS. Filters were monitored with a Geiger counter to see that the background was reduced.

Positive clones were plaque purified, and the plasmid pZL1 containing the cDNA inserts was rescued using the CRE LOX recombination system (GIBCO) (plasmid pZL1 is contained within the body of the lambda Ziplox vector). In particular, a purified phage plaque was suspended in 200 µl of phage buffer (20 mM Tris HCl, pH 7.5, 145 mM NaCl, 8 mM MgSO$_4$.7H$_2$O, 0.01% gelatin) for 5 minutes at room temperature. 20 µl of the phage suspension was then added to 100 µl of an overnight culture of DH10B (ZL) and incubated for an additional 5 minutes. Dilutions of the mixture were then plated on LB plates supplemented with ampicillin at 50 µg/ml and 10 mM MgCl$_2$, and incubated overnight at 30° C. Single colonies, now containing the cDNA inserted into the pZL1 vector were grown as standard overnight cultures and plasmids were then purified using Qiagen plasmid purification reagents.

Identification of Distinct Functional Human MAdCAM-1 cDNA Clones

Two human cDNA libraries from histologically normal human mesenteric lymph nodes, and inflamed mesenteric lymph nodes from a patient with Crohn's disease were screened using the entire macaque MAdCAM-1 cDNA as a probe. One cross-hybridizing clone was isolated from the normal library, and two cross-hybridizing clones were isolated from the Crohn's library. One of the two clones isolated from the Crohn's library was about 1.3 kb, appeared to be incomplete at the 5'-end, and was not sequenced. The clone from the normal library (clone 4) was slightly larger (1624 bp) than the longer clone (1558 bp) isolated from the Crohn's library (clone 20). Although these two cDNAs differ in size by approximately 100 bp, their 5' and 3' untranslated sequences were almost identical in length. Each clone appeared full-length, as they both contained an amino-terminal signal sequence that was almost identical to the macaque sequence.

Additionally, preliminary sequencing demonstrated the same distinguishing characteristics of the amino-terminal Ig-like domain as the primate cDNA. Since the differences in the size of these clones could not be attributed to the length of the untranslated sequences, it seemed likely that the variation resided in the coding region.

In order to determine whether each clone encoded functional human MAdCAM-1, the inserts of each clone were subcloned into the pCDNA-3 expression vector (Invitrogen, San Diego, Calif.), which carries a neo resistance gene suitable for G418 selection. The human cDNAs (which were made using NotI oligo-dT primers at the 3'-end, and SalI adapters at the 5'-end) were ligated into the λZipLox vector, which contains plasmid pZL1. pZL1 vectors with cDNA inserts were rescued as described above. For subcloning, the inserts of clones 4 and 20 were each released by digestion from the pZL1 backbone with EcoRI and NotI. The EcoRI-NotI (5'→3') fragments were isolated by Geneclean (Bio 101) following electrophoresis on a 1% agarose gel, and the fragments were ligated into pcDNA-3 which had been cleaved with EcoRI and NotI. The ligation mixture was used to transform a DH10B *E. coli* Max efficiency strain (GIBCO), and transformants were obtained following selection on LB agar supplemented with 50 µg/ml ampicillin (Amp). Plasmids designated pcD3huMAd4 (insert from clone 4) and pcD3huMAd20 (insert from clone 20) were obtained and analyzed by restriction digestion.

Clone pcD3huMAd4 (insert from clone 4) or pcD3huMAd20 (insert from clone 20) was transiently transfected into CHO/P cells. Each clone directed the expression of a functional protein which could mediate binding and adhesion, as assessed by adhesion of CHO/P transfectants to the human B cell lymphoma RPMI 8866 (FIG. 5) or to TK1 cells (not shown).

Adhesion of the CHO/P transfectants to RPMI 8866 cells was blocked by preincubation with anti-α4β7 MAb ACT-1, but not by control IgG. Adhesion of transfectants to TK1 cells was blocked by anti-β7 MAb FIB 504. These results indicate that clone 4 (from a normal mesenteric node library) and clone 20 (from a Crohn's library) each encode functional MAdCAM-1 proteins. To further characterize these distinct cDNAs, both clones were completely sequenced.

Results

The cDNAs from Clones 4 and 20, encoding human MAdCAM-1, are 1628 bp and 1543 bp, respectively, in length. cDNA from Clone 4 (FIG. 1; SEQ ID NO:1) contains an open reading frame of 1218 bp encoding a predicted protein of 406 amino acids (SEQ ID NO:2), and a 3' untranslated region of 410 bp, but contains no 5' untranslated region. cDNA from Clone 20 (FIG. 2; SEQ ID NO:3) contains 4 bp of 5' untranslated sequence, an open reading frame of 1146 bp encoding a predicted protein of 382 amino acids (SEQ ID NO:4), and a 3' untranslated region of 393 bp. The predicted molecular masses of the encoded proteins, after cleavage of a predicted signal sequence of 18 amino acids are 40,910 (clone 4) and 38,375 (clone 20) daltons.

Multiple alignments were performed to analyze the degree of similarity between the different cloned species of MAdCAM-1. Nucleotide alignments revealed 81.9% sequence similarity between mouse and rat MAdCAM-1 cDNAs, 41.8% similarity between mouse and macaque cDNAs, 42.1% similarity between murine and human (Clone 4) MAdCAM-1 cDNAs, and 41.8% similarity between murine and human (Clone 20) MAdCAM-1 cDNAs. Alignment of the nucleotide sequences of macaque MAdCAM-1 with human Clone 4 and Clone 20 cDNAs revealed sequence similarities of 70.7% and 75.0%, respectively.

The amino acid sequence similarities were determined to be 78.5% between mouse and rat MAdCAM-1, 44.3% between mouse and macaque, and 39% between murine and MAdCAM-1 encoded by human Clone 4.

Comparisons of cDNA clones 4 and 20 revealed a region which is homologous to the mucin domain of murine MAdCAM-1, due to a prevalence of serine, threonine and proline (69% for clone 4 and 76% for clone 20) residues (boxed in FIG. 1 and FIG. 2). This region, although similar in amino acid composition to murine MAdCAM-1, is highly divergent from murine MAdCAM-1. The domain is 71 amino acids long in clone 4, and 47 amino acids long in clone 20. This region also contains two polymorphisms: (1) a polymorphism at amino acid 240, which is proline (P) in clone 4 and serine (S) in clone 20; and (2) a polymorphism at amino acid 242, which is asparagine (N) in clone 4 and aspartate (D) in clone 20. In addition, the human mucin domains contain a repeat of 8 amino acids consisting of the sequence PPDTTS(Q/P)E (see e.g., amino acid residues 264-271 and 232-239, respectively, of SEQ ID NOS:1 and 2), which appears eight times in clone 4 and five times in clone 20.

To assess the origin of clones 4 and 20, PCR primers flanking the repeat were used to amplify human genomic DNA. The following primers were used:

```
5'-CTC TAC TGC CAG GCC ACG-3'    (Primer #1, SEQ ID
                                  NO: 7)
5'-AGC CTG GGA GAT CTC AGG G-3'   (Primer #2, SEQ ID
                                  NO: 8)
5'-GCC ACG ATG AGG CTG CCT GG-3'  (Primer #3, SEQ ID
                                  NO: 9)
5'-GTG GAG CCT GGG CTC CTG GG-3'  (Primer #4, SEQ ID
                                  NO: 10)
```

The primers were nested primers. In the first reaction, primers 1 and 2 were used. For the second amplification reaction, a 1:1000 dilution of the first reaction was prepared, and 1 µl was used with primers 3 and 4. Amplification reactions contained either 0.5 µg of genomic DNA, 10 picograms of control plasmids (pcD3HuMAd4 or pcD3HuMAd20), or approximately 1 ng of double-stranded cDNA that was prepared previously for the ZipLox libraries. Genomic DNA was obtained from three sources (Promega; ClonTech, and by purification from Jurkat cells). The conditions of amplification were: one cycle for 5 minutes at 94° C.; 25 cycles at 94° C. for 45 seconds; 60° C. for 45 seconds and 72° C. for one minute followed by one cycle for 5 minutes at 72° C.

The amplification reactions from genomic DNA yielded two bands which comigrated with the individual products of PCR reactions using either clone 4 or clone 20 cDNA as template. This data suggests that the two cDNA clones are isoforms encoded by genomic DNA, and are probably generated by alternative splicing or by transcription of two different alleles. Extensive polymorphism and sequence divergence has been documented in other mucin sequences (e.g., Hilkens, J. et al., *Trends, Biochem. Sci*, 17: 359-363 (1992)). For example, repetitive portions of intestinal mucins are not well-conserved between rodents and humans (Gum, J. G. et al., *J. Biol. Chem.*, 266: 22733-22738 (1991)). One caveat is that, based on an analysis of murine genomic structure, the human genomic DNA could contain an intron in this region. If so, the PCR primers used in this experiment would span the intron, and amplification of human genomic DNA would not be expected to produce bands of the same size as those produced by amplification of the cDNA controls. Isolation and analysis of human MAdCAM-1 genomic clones can conclusively exclude the possibility of a cloning artifact. Further assessment of normal and/or inflamed tissue from normal individuals and from patients with IBD, Crohn's disease or other inflammatory conditions can be performed to determine if there is a correlation between the clone 20 isoform and an inflammatory disease or activity.

The comparison of murine, macaque, and two isoforms of human MAdCAM-1 indicates that the amino-terminal portions of these receptors exhibit domain structures likely to be involved in recognition of α4β7. In contrast, the regions of these receptors in a location corresponding to the location of the mucin/IgA domain of murine MAdCAM-1 display similar amino acid compositions (serine, threonine, proline-rich mucin regions), but are more divergent from one another.

Expression of Human MAdCAM-1 RNA

Northern analysis was carried out using human multiple tissue Northerns I and II (commercially prepared by Clontech, Palo Alto, Calif.), or 2 µg of poly A+ RNA from cell lines and tissues that were prepared as described above. RNA was denatured and electrophoresed through a 1% agarose formaldehyde gel and transferred to a PVDF (Immobilon, Millipore) membrane by standard capillary blot procedures. RNA samples were stained with ethidium bromide to initially ensure that the quality and quantity of each cell or tissue RNA was equivalent. After transfer, RNA was fixed to membranes by UV crosslinking (Stratalinker, Stratagene) and this blot and the commercially prepared blots were pre-hybridized at 68° C. for 1 hour in ExpressHyb (Clontech). The cDNA insert from clone 4 was labeled with $\alpha^{32}$P-dCTP by priming with random hexamers (Maniatis et al., In *Molecular Cloning: A Laboratory Manual*, Cold Spring Harbor Laboratory, Cold Spring Harbor, N.Y., (199)). Hybridization was performed at 68° C. for 1 hour in ExpressHyb with denatured probe at a concentration of $2\times10^6$ cpm/ml.

Blots were then washed in 0.1×SSC, 0.1% SDS for 60 minutes at 65° C. with one change of wash at 30 minutes. The exposure time was 48 hours with an intensifying screen. After this exposure, the blot was stripped by washing for 10 minutes in 0.5% SDS and rehybridized under the same conditions with a β-actin cDNA. The exposure time was 2 hours.

Results

Northern blots were probed for MAdCAM-1 expression using the entire cDNA insert from clone 4 as a probe. A single RNA species of approximately 1.6 kb was highly expressed in the small intestine and was expressed to a lesser extent in the colon and spleen. No significant expression was observed in other tissues examined under these conditions, including thymus, prostate, ovaries, testes and peripheral blood leukocytes (PBL). This tissue-specific pattern of expression is consistent with studies in the mouse showing restricted expression of MAdCAM-1 in Peyer's Patches, MLN (mesenteric lymph node), intestinal lamina propria and some expression in the marginal sinus around splenic white pulp nodules in the spleen (Hemler, M. E., *Annu. Rev. Immunol.*, 8:365 (1990); Berg, E. L., et al., *Cellular and molecular mechanisms of inflammation*, 2:111 (1991); Briskin, M. J., et al., *Nature*, 363:461 (1993)). No significant expression was observed in other tissues examined, including heart, brain, placenta, lung, liver, skeletal muscle, or kidney; however, low levels of expression were detected in pancreas. These data indicate that human MAdCAM-1 expression is tissue-specific with expression in mucosal tissues and spleen; a thorough immunohistochemical analysis of tissue distribution can be performed using monoclonal antibodies against human MAdCAM-1 (see below).

Example 2

Characterization of MAdCAM-1 Clones

Functional Adhesion Assays

Plasmids:

The following plasmids were used in the functional adhesion assays: (1) pSV-SPORT-1 (Gibco/BRL) or pcDNA-3 (Invitrogen) were used as controls; (2) murine MAdCAM-1 in pCDM8 (pCDMAD-7; Briskin, M. J., et al., *Nature*, 363: 461 (1993)); (3) seven domain human VCAM-1 (Polte, T., et al., *Nucleic Acids Res.*, 18:5901 (1990)) in pcDNA3 (pCD3VCAM); and (4) human MAdCAM-1 in pcDNA-3 (pCDhuMAd4) (see above).

Monoclonal Antibodies:

The following monoclonal antibodies (MAb) were used in the functional adhesion assays: (1) anti-murine MAdCAM-1 MAb MECA-367 (American Type Culture Collection (Rockville, Md.), Accession No. HB9478; Streeter, P. R., et al., *Nature*, 331:41 (1988); and U.S. Pat. No. 5,403,919 to Butcher); (2) anti-human VCAM-1 MAb 2G7 (American Type Culture Collection (Rockville, Md.); Graber, N. T., et al., *J. Immunol.*, 145:819-830 (1990)); (3) anti-murine $\alpha 4\beta 7$ MAb DATK 32 (Andrew, D. P., et al., *J. Immunol.*, 153:3847-3861 (1994)); (4) anti-murine $\beta 7$ MAb FIB 504 (Andrew, D. P., et al., *J. Immunol.*, 153: 3847 (1994)); (5) anti-human $\alpha 4\beta 7$ MAb ACT-1 (Lazarovits, A. I., et al., *J. Immunol.*, 133:1857 (1984)); (6) anti-human integrin $\beta 1$ (CD29) (Becton Dickinson; San Jose, Calif., Cat. #550034); and (7) murine IgG1 and rat IgG2A as irrelevant controls.

Cell Lines:

The following cell lines were used in functional adhesion assays:

(1) Murine T cell lymphoma TK1 (Butcher, E. C., et al., *Eur. J. Immunol.*, 10:556-561 (1980); E. Butcher (Stanford, Calif.); (2) RPMI 8866, a human B cell lymphoma line which expresses $\alpha 4\beta 7$ (and not $\alpha 4\beta 1$) (American Type Culture Collection (Rockville, Md.); Erle, D. J., et al., *J. Immunol.*, 153: 517 (1994); a gift from D. Erle); (3) JURKAT, a human T cell line which expresses $\alpha 4\beta 1$ (and not $\alpha 4\beta 7$) (American Type Culture Collection (Rockville, Md.)); and (4) Ramos, a human (B lymphocytic) Burkitt lymphoma cell line that expresses $\alpha 4\beta 1$ (and not $\alpha 4\beta 7$) (American Type Culture Collection (Rockville, Mass.), Accession No. ATCC CRL 1596).

Functional Adhesion Assays:

For functional adhesion assays, plasmids encoding various species of MAdCAM-1, human VCAM-1, and control plasmids were introduced by transient transfection into CHO/P cells as described above (Example 1) with the following modifications. As several wells were to be transfected for antibody inhibition studies, a master liposome mix with multiples of the wells to be transfected was first made for each plasmid. This ensured that the same liposome mixture was transfected into each well.

48 hours after transfection, the medium was removed. An antibody supernatant (0.25 mls) (containing either anti-human VCAM-1 MAb 2G7 or anti-murine MAdCAM-1 MAb MECA-367), or 0.25 mls of adhesion assay buffer as a control were added, and the mixture was preincubated at 4° C. for 15 minutes.

In parallel, lymphocyte cell lines (RPMI 8866 or Jurkat) were spun down and resuspended at a density of $2\times10^6$/ml in assay buffer consisting of HBSS (without $Ca^{++}$ or $Mg^{++}$) supplemented with 2% bovine calf serum, 20 mM HEPES pH 7.3, 2 mM $Mg^{++}$ and 2 mM $Ca^{++}$. 0.25 ml aliquots ($5\times10^5$ cells) of these RPMI 8866 or JURKAT cell suspensions were preincubated with a small volume of various purified antibodies or with an equal volume of DATK 32 supernatant at 4° C. for 15 minutes. Where DATK 32 was used in a preincubation with a cell line, prior to the start of the assay, the supernatant or buffer present in the wells (containing the transfectants) was aspirated in order to obtain volume of 0.5 ml total for the adhesion assay.

For preincubations, purified antibodies (ACT 1, FIB 504 anti-β1) and control IgG antibodies were used at concentrations of 20 µg/ml. 0.25 mls of antibody supernatant (used neat) containing anti-human VCAM-1 (MAb 2G7) or anti-murine MAdCAM-1 (MAb MECA-367) were used in preincubations. 0.25 mls of antibody supernatant of DATK 32 were used in the preincubation.

After the preincubations, cell lines (Jurkat or RPMI 8866) were combined with the tranfectants in the wells, and incubation on a rocking platform was continued for an additional 30 minutes at 4° C.

Assays were fixed as described above. Plates were washed by gentle inversion in a large beaker of phosphate buffered saline (PBS), followed by inversion in a beaker of PBS with 1.5% gluteraldehyde for fixation for a minimum of 1 hour. Adhesion was assessed by counting both lymphocytes and CHO cells in a field at 20× magnification. For each assay, the number of lymphocytes bound per CHO/P cell was averaged as a minimum of four fields with standard error. Results in each case are from one of three experiments performed with similar results.

Results

Murine MAdCAM-1 specifically binds lymphocytes expressing α4β7 (and not α4β1). In order to determine the specificity of human MAdCAM-1 lymphocyte interactions, adhesion assays were performed to assess the ability of transiently transfected CHO/P cells expressing human MAdCAM-1 to bind to the RPMI 8866 cell line which only expresses α4β7 (Erle, D. J., et al., *J. Immunol.*, 153:517 (1994)), or to the T cell line Jurkat, which exclusively express α4β1. Binding of these cell lines was compared to that of transiently transfected CHO/P cells expressing murine MAdCAM-1 and human VCAM-1. The results are presented in FIGS. 4A-4B.

RPMI 8866 cells did not bind to control transfectants, but avidly bound to transfectants expressing human or murine MAdCAM-1. This binding was completely inhibited by preincubation with anti-α4β7 MAb ACT-1 (FIG. 4A). VCAM-1 transfectants failed to bind RPMI 8866, which is consistent with the previous demonstration that α4β7/VCAM-1 interactions are activation-dependent (Postigo, A. A., et al., *J. Immunol.*, 151:2471-2483 (1993); Ruegg, C., et al., *J. Cell. Biol.*, 117:179-189 (1992)). The failure of RPMI 8866 cells to bind VCAM-1 transfectants was not due to lack of expression, as FACS analysis using anti-VCAM-1 MAb 2G7 indicated a transfection efficiency of ~60%. Moroever, the same VCAM-1 transfectants were able to bind Jurkat cells, and binding was completely inhibited by preincubation with either anti-VCAM-1 or anti-β1 MAbs (FIG. 4B). Murine and human MAdCAM-1 transfectants did not bind Jurkat cells (an α4β1 positive line). These data demonstrate that human MAdCAM-1 can selectively bind to human leukocytes lymphocytes expressing α4β7 integrins.

L1-2 and CHO Cell Transfectants

The mouse L1-2 cell line is derived from a pre-B lymphoma, and was obtained from Dr. Eugene Butcher (Stanford University, Stanford, Calif.). The genes encoding either the macaque or human cDNAs for MAdCAM-1 were subcloned into the pcDNA-3 vector (Invitrogen) as described above. The resulting plasmids (pcD3HuMAd4, pcD3HuMAd20, or pCD3PMad (macaque)) were introduced into L1-2 cells by transfection as follows: L1-2 cells were grown to a density of approximately $10^6$/ml. Either 50, 25 or 12.5 million cells were washed in HBSS and then resuspended in a 0.8 ml of a buffer consisting of Hanks balanced salt solution supplemented with 20 mM HEPES, pH 7.05. A solution consisting of 20 µg of linearized plasmid, 500 µg of tRNA and HBSS to bring the final volume to 200 µl was added to the cell suspension to bring the total volume to 1 ml. After a 10 minute incubation at room temperature the cell/DNA mixture was transferred to an electroporation cuvette (BioRad, Richmond, Calif.) and electroporated at 250 volts, 960 mF in a BioRad gene pulser. Following another 10 minute incubation at room temperature, the cells were diluted to 25 ml in standard L1-2 growth media (RPMI 1640, 10% Hyclone fetal bovine serum, 50 U/ml Penicillin/Styreptomycin (Gibco) and 0.29 mg/ml L Glutamine (Gibco) and returned to the incubator at 37° C. 48 hours later, the cells were pelleted by centrifugation and resuspended in 50 ml of L1-2 media supplemented with G418 (Geneticin; Gibco) at 0.8 mg/ml. Dilutions of the cell suspension were plated in 96-well microtiter plates and single colonies were grown up analyzed for expression of MAdCAM-1.

L1-2 cell clones expressing MAdCAM-1 could be detected by adherence to TK1 cells. L1-2 (non-transfected cells) and TK1 cells both grow as single cell suspensions.

Surface expression of MAdCAM-1 can be detected by its ability to mediate adhesion by virtue of its interaction with α4β7 expressed on TK1 cells. Specificity of this interaction was further demonstrated by inhibition by pretreatment of TK1 cells with anti-β7 MAb FIB 504.

CHO cells (Chinese Hamster Ovary Cells; American Type Culture Collection (Rockville, Md.)) stably transfected with either the macaque or human MAdCAM-1 clones were prepared by electroporation as described above for the L1-2 cells with the following exceptions. Media for CHO cell growth was α-MEM with deoxyribonucleosides (Gibco) and 10% fetal calf serum (Gibco) and 50 U/ml Penicillin/Streptomycin (Gibco) and 0.29 mg/ml L Glutamine (Gibco). Selection media consisted of the same media with 0.55 mg/ml G418 (Gibco). Single clones were grown up and analyzed for their ability to exhibit α4β7-dependent binding of RPMI 8866 cells using the functional adhesion assay described above (for transients), except that cells were plated at 50,000 cells per well in a 24-well plate the day before the assay. Using this criteria, a line called CHO HuMAd 4 was established.

Monoclonal Antibodies Capable of Inhibiting Adhesion

Monoclonal antibodies against human MAdCAM-1 were generated by immunizing C57BL/6 mice with L1-2 MAdCAM-1 transfectants. Mice were immunized intraperitoneally with 10 million cells resuspended in HBSS three times at two week intervals, and a final fourth immunization (of 10 million cells resuspended in HBSS) was injected intravenously. The first immunization was performed with a mixture of two clones (L1-2 cell clone 23 and clone 19) expressing macaque MAdCAM-1. The remaining boosts were done with a single L1-2 clone (L1-2 clone HuMAD4/17) expressing human MAdCAM-1.

A successful fusion was performed which generated approximately 5,000 hybridomas. Four days after the final intravenous injection, the spleen was removed and a single cell suspension was prepared in serum free DMEM media. These cells were fused with the fusion partner SP2/0, according to the method of Galfre et al. (Galfre, G., et al., *Nature,* 299:550-552 (1977)). 20 ml of spleen cells and 20 ml of SP2/0 cells were combined, spun at 800 g for 5 minutes and the media was removed by aspiration. A solution of 50% polyethylene glycol 1500 (PEG 1500) (Boehringer Mannheim, Indianapolis, Ind.) prewarmed to 37° C. was added to the cell pellet over 2 minutes, followed by 10 ml of DMEM media over 3 minutes. The cell suspension was spun at 600 g for 3 minutes and the supernatant was removed. The pellet was resuspended gently in DMEM media containing 20% fetal calf serum, 2 mM L-glutamine, 100 U/ml penicillin, 100 µg/ml streptomycin sulfate, and HAT selection media (Sigma, St. Louis, Mo.). Cells were plated into ten 96-well flat bottom microtiter plates at 200 µl/well.

Ten days after the fusion, supernatants from the wells were screened for reactivity against CHO human MAdCAM-1 transfectants (CHO HuMAd 4 cells), by fluorescence staining. Staining of 500,000 cells per sample was performed essentially as described, using 50 µl of each supernatant and 50 µl cells (E. Harlow and D. Lane, 1989, In: *Antibodies: A Laboratory Manual*, Cold Spring Harbor Laboratory, Cold Spring Harbor, N.Y.). The secondary antibody was an FITC-labeled anti-murine IgG (H+L) (Jackson Labs) that was diluted 1:200. Strong reactivity was judged as a 2-3 log increase in fluorescence of as compared with untransfected CHO cells.

48 antibody supernatants were selected for strong reactivity against CHO HuMAd 4 cells. These antibody supernatants were then screened for their ability to block the adhesion of CHO HuMAd 4 cells to RPMI 8866 cells. As a control, the ability of supernatants to inhibit Ramos cell binding to VCAM-1 transfectants was examined, as it should not be affected by a specific anti-human MAdCAM-1 MAb. To identify blocking anti-human MAdCAM-1 monoclonal antibodies, the following assay was performed. To provide control transfectants, CHO/P cells were transfected with pCD3VCAM as described above, and were assayed 48 hours after transfection. 48 hours before the adhesion inhibition assay, 40,000 cells per well of VCAM-1 transient transfectants were plated into 24 well plates. 24 hours before assay, 50,000 cells per well of CHOHuMAd 4 transfectants were plated in 24 well plates. On the day of the assay, each anti-human MAdCAM-1 supernatant (0.25 mls) was added to a well containing either CHOHuMAD 4 transfectants or VCAM-1 transfectants, and the mixture was preincubated at 4° C. for 15 minutes. Adhesion assays were performed, using (1) RPMI 8866 cells with the MAdCAM-1 transfectants or (2) Ramos cells (a human B cell line that expresses α4β1) with the VCAM-1 transfectants.

In parallel, cells (RPMI 8866 or Ramos) were resuspended at a density of $2 \times 10^6$/ml in an assay buffer consisting of HBSS (without $Ca^{++}$ or $Mg^{++}$) supplemented with 2% bovine calf serum, 20 mM HEPES pH 7.3, 2 mM $Mg^{++}$ and 2 mM $Ca^{++}$. After the preincubation of the transfectants with antibody, 0.25 mls of the RPMI 8866 or Ramos cell suspensions (5×105 cells) were added to each well, and incubation on a rocking platform was continued for an additional 30 minutes at 4° C. The wells were washed, fixed and examined as described above to assess inhibition of binding.

Eleven out of 48 of the hybridoma supernatants examined displayed substantial blocking activity, inhibiting the adhesion of RPMI 8866 cells to transfectants expressing MAdCAM-1. Adhesion of Ramos cells to transfectants expressing VCAM-1 was unaffected, indicating selective inhibition of α4β7-mediated interactions. Selected blocking hybridomas were subcloned by limiting dilution.

Results

Stable cell lines expressing macaque or human MAdCAM-1 were made in the murine pre-B lymphoma L1-2. These cells were used to immunize C57BL/6 mice and prepare hybridomas. The resulting fusion was screened by immunoflourescence staining of CHO HuMAd 4 transfectants expressing human MAdCAM-1. Screening of approximately 1,000 wells produced 48 supernatants exhibiting strong reactivity against the CHO HuMAd 4 transfectants, while non-transfected CHO cells were negative. These supernatants were subsequently tested for their ability to specifically block adhesion of RPMI 8866 cells to human MAdCAM-1 transfectants.

11 of the 48 hybridoma supernatants examined could specifically inhibit the adhesion of RPMI 8866 cells to MAdCAM-1, while adhesion of Ramos cells (which express α4β1) to VCAM-1 transfectants was unaffected by the same supernatants. These hybridomas were designated 10G4, 8C1, 10G3, 9G12, 9E4, 7H12, 10F2, 10A6, 1E5, 2F5, 7G11.

Example 3

Design and Functional Analysis of a Human MAdCAM-1-IgG Chimera

Construction of MAdCAM-IgG Chimera

Human MAdCAM-1 clone 4 cDNA in pCDNA3 (Invitrogen, San Diego, Calif.), called pcD3huMAd4 (Example 1) was used as a template for PCR amplification of extracellular regions of human MAdCAM-1 to be fused with the constant region of human IgG1. Primer HUMADIG4/2 (SEQ ID NO:11), which contains the 5' end of human MAdCAM-1 coding sequence (ATG codon, bold), was synthesized:

```
     HindIII
5'-GGAAGCTTCCACCATGGATTTCGGACTGGCCC-3'
```

This 5' primer was used in conjunction with a 3' primer designated HUMADIG2 (SEQ ID NO:12) to amplify regions encoding the two amino-terminal immunoglobulin-like (Ig) domains of human MAdCAM-1. Primer HUMADIG2 (SEQ ID NO:12), which contains a portion complementary to coding strand nucleotides 667-683 of SEQ ID NO:1, has the following sequence:

```
        SpeI
5'-CCGACTAGTGTCGGGCTGTGCAGGAC-3'
```

Alternatively, the 5' primer was used in conjunction with 3' primer HUMADIG3 to amplify a region encoding the entire extracellular domain of human MAdCAM-1 (clone 4). The 3' primer HUMADIG2 (SEQ ID NO:13), which contains a portion complementary to coding strand nucleotides 992-1010 of SEQ ID NO:1, has the following sequence:

```
         SpeI
5'-GGACTAGTGGTTTGGACGAGCCTGTTG-3'
```

The primers were designed with a 5' HindIII site or 3' SpeI sites as indicated. These primers were used to PCR amplify two different MAdCAM fragments, using a PCR optimizer kit from Invitrogen (San Diego, Calif.). The PCR products were digested with the enzymes HindIII and SpeI to generate ends for cloning. The products were subsequently purified by gel electrophoresis using the Glassmax DNA isolation system (Gibco, Bethesda Md.).

A ~1 kb fragment encompassing the CH1, H (hinge), CH2 and CH3 regions was excised by digestion with SpeI and EcoRI from a construct encoding a human immunoglobulin γ1 heavy chain having an Fc-mutated human constant region. The antibody encoded by this construct was used as an isotype matched irrelevant control hereinbelow. The human constant region in this construct was originally obtained by PCR amplification of the CAMPATH-1H heavy chain (Reichmann, L. et al., Nature, 322: 323-327 (1988)) as described by Sims, M. J. et al. (J. Immunol., 151: 2296-2308 (1993)) and Waldmann et al. (WO 93/02191, Feb. 4, 1993 (page 23)), the teachings of which are each incorporated herein by reference in their entirety. The mutations in the constant region of this construct ($Leu^{234} \rightarrow Ala^{234}$ and $Gly^{237} \rightarrow Ala^{237}$) were designed to reduce binding to human Fcγ receptors, and were produced by oligonucleotide-directed mutagenesis. Thus, the MAdCAM-Ig fusions produced contain the SpeI-EcoRI constant region fragment described by Sims et al. (J. Immunol., 151: 2296-2308 (1993)) and Waldmann et al. (WO 93/02191), except for the introduction of $Leu^{234} \rightarrow Ala^{234}$ and $Gly^{237} \rightarrow Ala^{237}$ mutations.

The 1 kb SpeI-EcoRI fragment encoding the Fc-mutated IgG1 constant region was isolated by gel electrophoresis using the Glassmax DNA isolation system (Gibco, Bethesda Md.). This constant region fragment, the HindIII-SpeI fragments containing either (a) the two N-terminal Ig domains of MAdCAM-1 or (b) the entire extracellular domain, were ligated in a three-way ligation to vector pEE12 (Stephens, P. L. and M. L. Cockett, *Nucl. Acids Res.,* 17: 7110 (1989) and Bebbington, C. R. and C. C. G. Hentschel, 1987, *The use of vectors based on gene amplification for the expression of cloned genes in mammalian cells,* (Academic Press, N.Y.), which had been digested with HindIII and EcoRI. Transformants of the bacterial strain DH10B were obtained. Colonies were grown and mini plasmid preps were analyzed by restriction mapping. Three constructs which encode fusion proteins comprising either the entire extracellular domain of MAdCAM-1 (construct HuMAdIg21) or the two N-terminal Ig domains (construct HuMAdIg31 or HuMAdIg38) fused to the Fc-mutated IgG1 constant region, were sequenced across the entire MAdCAM-1 portions, confirming proper fusion of segments and the absence of PCR induced mutations.

For initial testing, each construct was transiently transfected onto monolayers of $5 \times 10^7$ COS cells in 1 ml of RPMI buffer (no serum) and 25 µg of plasmid using electroporation with a Biorad Gene Pulser under standard conditions (960 µF, 250 V). 72-96 hours after transfection, supernatants were harvested, passaged through 0.45µ filters and stored at 4° C. in the presence of 0.05% sodium azide. Production of chimera was confirmed by a sandwich ELISA, using an anti-human IgG1 antibody as capture antibody and the same antibody, which was conjugated to alkaline phosphatase as second antibody for detection. Irrelevant control antibody (having an identical constant region) was used as a standard. The chimera was also analyzed by western blotting using an anti-human MAdCAM-1 monoclonal antibody, and was found to run at approximately 200 kd, consistent with the size of a homodimer.

Soluble Human MAdCAM-Ig Chimeras Specifically Bind α4β7 Positive Cells

Supernatants from four different transfections were assayed for their ability to stain the T cell line HuT 78, which was previously shown to bind MAdCAM-1 only in the presence of Mn++. Accordingly, each solution used in this assay contained 2 mM Mn++. HuT 78 cells (a human T cell lymphoma line; American Type Culture Collection, Accession No. ATCC TIB 161) are α4β7-bearing cells. To test the binding specificity of the chimeras, Hut 78 cells were preincubated with either media alone (RPMI 1640 with 2% FCS) or media and 10 µg/ml of the anti-β7 antibody FIB 504. Approximately 100,000 cells were incubated on ice for 15 minutes and then washed with HBSS plus 2% FCS/2 mM $Ca^{++}$/2 mM $Mn^{++}$. Cells were then incubated for 20 minutes on ice with media once again or with supernatants from one of four independent transfections, two with a chimera containing the entire extracellular domain of MAdCAM-1 (clone 21) and two with a truncated form of MAdCAM containing the two N-terminal Ig domains (clone 38) for 20 minutes. After washing, cells were then incubated with an anti-human IgG antibody conjugated with phycoerythrin and staining above background was assessed by flow cytometry (FACScan). Only cells incubated with the chimera supernatants stained above background, while preincubation with the β7 MAb reduced this staining to background levels, indicating a specific interaction of the chimera with the α4β7 integrin (FIGS. 17A-17E).

Permanent NSO cell lines secreting human MAdCAM-Ig chimera were selected after transfection by electroporation, by growth in a glutamine free media as previously described (Cockett, M. L., et al., *Bio/Technology,* 8: 662-667 (1990)). Cloned lines were adapted to growth in spinner culture. Supernatants from three of these cloned lines (samples B-D), and a partially purified chimera (Clone 21, purified by binding to protein A, sample A) were tested for their ability to support adhesion of the B cell line RPMI 8866. Briefly, NEN maxisorb plates were incubated with 100 µl/well of Protein A at 20 µg/ml in carbonate buffer, pH 9.5 overnight at 4° C. Plates were then washed 2× with RPMI 1640 media (no serum). 100 µl of chimera (or serial dilutions in RPMI) were bound to the wells at 37° for 2 hours and then washed once. Wells were then blocked with FCS for 1 hour at 37° C., washed once, and then preincubated with tissue culture supernatants containing either an anti-human VCAM-1 MAb (2G7) as a control or the anti-human MAdCAM-1 MAb 10G3 (Example 2). 2G7 and 10G3 MAbs were removed before addition of cells. RPMI 8866 cells were fluorescently labeled by preincubation with BCECF-AM stain (BCECF-AM; 2′,7′-bis-(2-carboxyethyl)-5-(and-6)-carboxyflourescein, acetoxymethyl ester; Molecular Probes), 100 µl of cells were added to each well (to a final concentration of $10^5$ cell/well), and incubated on a rotary shaker for 30 minutes at room temperature. Binding of RPMI 8866 cells to immobilized chimeras was assessed by reading flourescence values using a Fluorescence Concentration Analyzer (IDEXX). Specific binding was demonstrated as only the anti-human MAdCAM-1 MAb could block binding of cells to MAdCAM-Ig chimera (Table 1).

These and other such chimeric fusion proteins can be used for assessing the ability of an agent (e.g., small molecule) to block α4β7 binding to chimera, to identify inhibitors of α4β7-MAdCAM interaction. Additionally, since chimeric fusion proteins can bind to α4β7 positive lymphocytes in solution, they provide candidate inhibitors of in vivo lymphocyte recruitment to inflammatory sites.

TABLE 1

| Sample | Anti HUMAd MAbs | Neat | 1:2 | 1:4 | 1:8 | 1:16 | 1:32 |
|---|---|---|---|---|---|---|---|
| A | − | 195527 | 195527 | 195527 | 18560 | 4254 | 3558 |
|   | + | 3860 | 3092 | 1746 | 2200 | 482 | 564 |
| B | − | 195527 | 195527 | 195527 | 195528 | 52056 | 2932 |
|   | + | 6526 | 3626 | 3274 | 2978 | 1648 | 1518 |
| C | − | 195527 | 195527 | 35548 | 9570 | 21782 | 1926 |
|   | + | 4566 | 4094 | 3922 | 3492 | 2436 | 2566 |
| D | − | 195527 | 30840 | 46852 | 16270 | 5474 | 2656 |
|   | + | 7350 | 6794 | 6020 | 4510 | 6548 | 5122 |

The α4β7 Positive B Cell Line RPMI 8866 Specifically Binds Soluble Human MAdCAM Ig Chimera. The Human MAdCAM-1 Ig Chimera Clone 21 that was partially purified over protein A (Sample A) or tissue culture supernatants from different NSO clones (Samples B-D) were immobilized on 96 well plates with protein A, and either pre-incubated with an anti-VCAM-1 MAb 2G7 (designated "-"under MAbs) as a negative control or with the anti-human MAdCAM MAb 10G3 ("+"). Purified chimera orsupernatants (used either undiluted ("neat") or at serial 1:2 dilutaions) was bound to wells via Protein A, and incubated with flourescently-labeled RPMI 8866 cells on a rotary shaker for 30 minutes at room temperature. After washing with an automated plate washer (EL 404 Microplate Autowasher, BIO-TEK Instruments), bound cells were counted with an automated plate reader (IDEXX). Raw numbers are thus a reflection of numbers of cells bound.

Example 4

Inhibition of Lymphocyte Recruitment to Colon

A. DSS-Induction of Colitis in Mice

BALB/c mice were given access to a 5% solution of dextran sodium sulfate (DSS) in their drinking water for a period of 10 days, as previously described (*Lab. Invest.* 69:238-249, 1993). During this time period, the mice developed clinical symptoms of colitis including softening of stools and bloody diarrhea. Multifocal epithelial injury and ulceration, similar to ulcerative colitis in humans, was evident on histologic examination of colonic mucosa from affected mice. Moreover, affected mice lost 20-30% of their initial body weight by day 10.

Antibody Blockade of β7 and MAdCAM Interactions

To determine the efficacy of β7-specific antibodies in blocking the recruitment of lymphocytes to the colon, BALB/c mice were given daily intraperitoneal (i.p.) injections of 100 µg of monoclonal antibodies against β7, consisting of either FIB21 or FIB30 in saline, as previously characterized and described (Berlin, C., et al., *Cell* 74:185-195, 1993; Michie, S. A., et al., *Am. J. Pathol.* 143:1688-1698, 1993; Hamann, A., et al., *J. Immunol.* 152:3282-3293, 1994) or an isotype-matched control rat monoclonal antibody at the same dose (Andrew et al., supra) over the 10 day course of DSS treatment.

Methods of Evaluation

Two methods were used to evaluate efficacy of the antibody therapy to inhibit leukocyte infiltration and mucosal injury in the colitic mouse. In the first method, treatment was judged histologically by two blinded observers using a scoring system for the evaluation of epithelial injury and degree of leukocyte cellular infiltration (Table 2). For this assessment, colon tissue was first fixed in 10% neutral buffered formalin, dehydrated, embedded in paraffin, sectioned, and the sections were stained with hematoxylin and eosin prior to examination.

TABLE 2

PATHOLOGY EVALUATION

| Grade | | Definition |
|---|---|---|
| INFLAMMATION | | |
| Normal | (0) | Absence of clusters of polymorphonoclear leukocytes (PMNs) or mononuclear cells in the lamina propria; absence of intraepithelial PMNs |
| Mild | (1) | Focal aggregates of PMNs and/or mononuclear cells in the lamina propria (equivocal or slight) or presence of isolated intraepithelial PMNs in 3 or fewer crypts per cross-section |
| Moderate | (2) | Focal aggregates of PMNs and/or mononuclear cells in the lamina propria (multi-focal or diffuse 2-5X) or intraepithelial PMNs in more than 3 crypts per cross-section |
| Severe | (3) | Diffuse infiltration of PMNs or mononuclear cells in the lamina propria (diffuse >5X) or crypt abscesses |
| STRUCTURAL OR EPITHELIAL ALTERATIONS | | |
| Normal | (0) | Tight crypts, no erosion, columnar epithelial cells |
| Mild | (1) | Epithelial immaturity; equivocal irregularity of epithelial surface |
| Moderate | (2) | At least two foci of crypt branching or loss of crypts (<50%); loss of surface epithelium |
| Severe | (3) | Diffuse or multifocal branching or loss of crypts (>50%); fibrosis; complete loss of epithelium (focal) |

Additional histologic assessment was performed using immunohistochemistry for the detection and semiquantification of lymphocytes expressing β7 integrins and mucosal venules expressing MAdCAM. As previously described (Ringler, D. J., et al., *Am. J. Pathol.*, 134: 373-383 (1989)), colon tissue was first snap-frozen in OCT compound, sectioned while frozen, and the sections were subsequently fixed in acetone for 10 min at 4° C. After washing in phosphate buffered saline (PBS), nonspecific antibody binding sites were blocked with 10% normal rabbit serum diluted in PBS for 10 min, followed in sequence with washes by FIB21 antibody at 20 µg/ml in PBS for 30 min at room temperature (RT), biotinylated rabbit anti-rat polyclonal antibody, avidin-peroxidase complexes, and finally the chromogen, diaminobenzidine and hydrogen peroxide diluted in Tris buffer.

In the second method, recruitment of lymphocytes to the colon was quantitatively assessed using radiolabeled mesenteric lymph node lymphocytes from syngeneic donor mice. The experimental design of the animal experiments was similar to that described above except that BALB/c mice were placed on 5% DSS for 9 days (instead of 10) and on day 8, mice were given i.p. injections of 100 µg of FIB21 (anti-β7), MECA-367 (anti-MAdCAM), a mixture of both, or an isotype-matched control monoclonal antibody in saline. On day 9, mesenteric lymph node cells were isolated from donor syngeneic BALB/c mice, labeled with $^{51}$Cr, and $5.0 \times 10^6$ cells/mouse were incubated for 30 minutes at 37° C. with 500 µg control antibody, 250 µg of MECA-367, 500 µg FIB21, or both (total amount is 750 µg) in saline. The labeled cells and antibody were then injected intravenously (i.v.) into the DSS-treated recipient mice. Full-length colons were harvested from all experimental animals 1 hour after injection, and γ-irradiation was measured using a γ-counter.

Data Analysis

Differences between mean scores obtained for each group of animals were assessed for statistical significance using a paired Student's t-test. Differences between means were considered significant when $P<0.05$.

Results

Histologically, inflammation and epithelial injury to the mucosa were most severe in the descending colon, rectum and cecum. Analysis of frozen tissue sections of colon by immunohistochemistry revealed that the most significant recruitment of β7+ lymphocytes was to the right colon. In addition, the level of expression of the mucosal vascular addressin, MAdCAM-1, was found to be expressed only at low levels in vessels in the intestinal mucosa early in DSS treatment (3 days), but increased dramatically after 9 days of DSS treatment, supporting the conclusion that β7 and MAdCAM-1 interactions are relevant to the inflammatory process in the colonic mucosa during DSS-induced colitis.

Figure 7A:
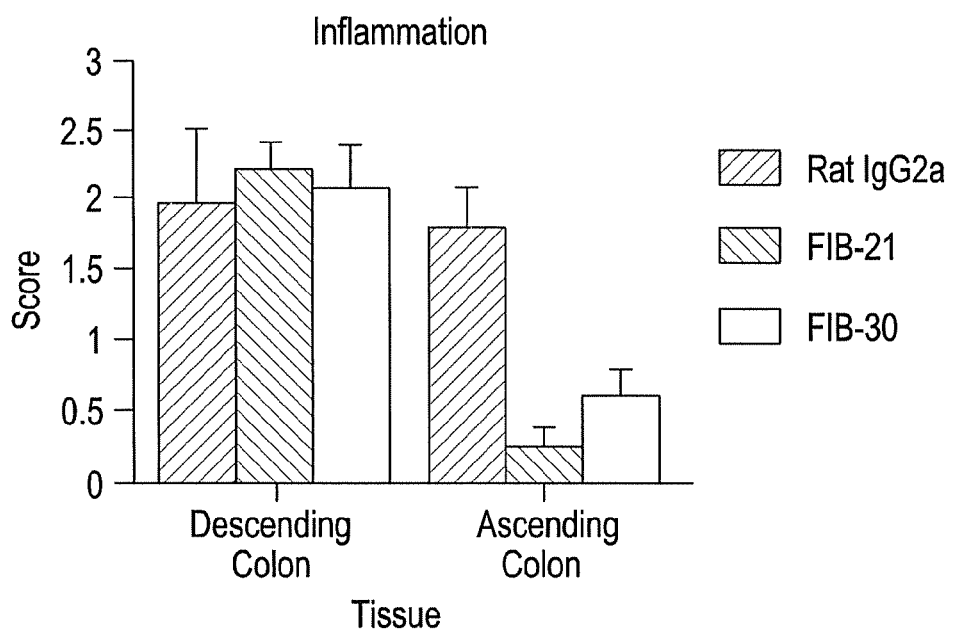
FIGS. 7A and 7B are graphic illustrations of histologic scores of inflammatory activity and epithelial injury from left (descending) and right (ascending) colon of mice exposed to 10 days of DSS in their drinking water. Three groups of mice are shown, consisting of groups receiving an irrelevant rat IgG2a antibody, FIB 21, or FIB 30 antibodies.
Figure 7B:
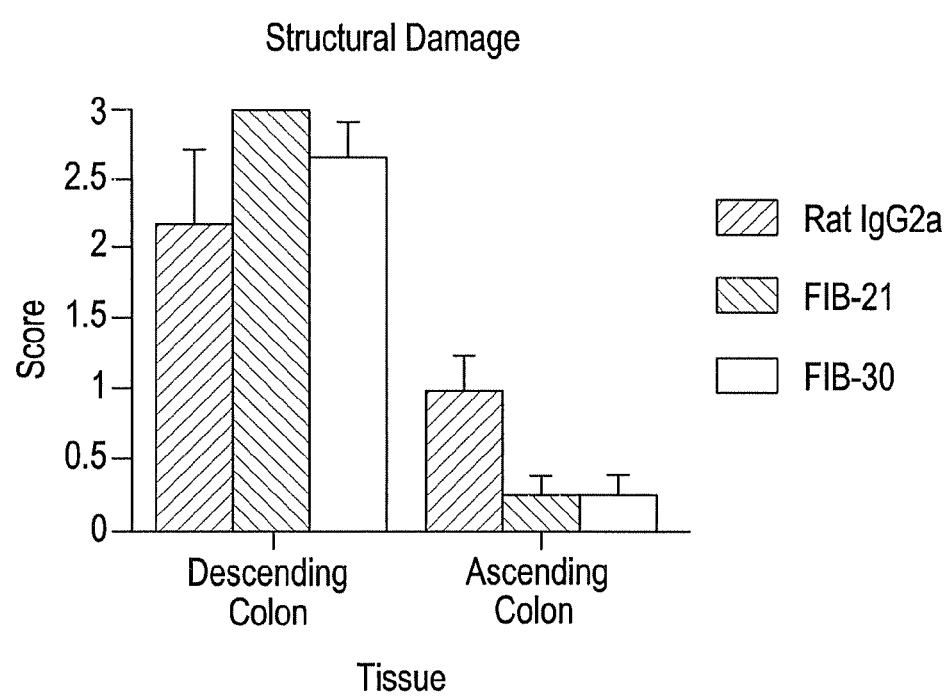

Histologic evaluation of mice exposed to a 10-day course of DSS and daily therapy using β7-specific antibodies demonstrated that substantial reductions of leukocyte recruitment ($P<0.01$ for FIB30 and $P<0.001$ for FIB21) and epithelial injury ($P<0.05$) occurred in right (ascending) colon compared to animals receiving a control antibody at the same dose (FIGS. 7A and 7B). Furthermore, analysis using immunohistochemistry of frozen sections from these animals suggested that the number of β7$^+$ cells recruited to the right colon, but not other sections of colon, during DSS treatment was reduced.

Figure 8:
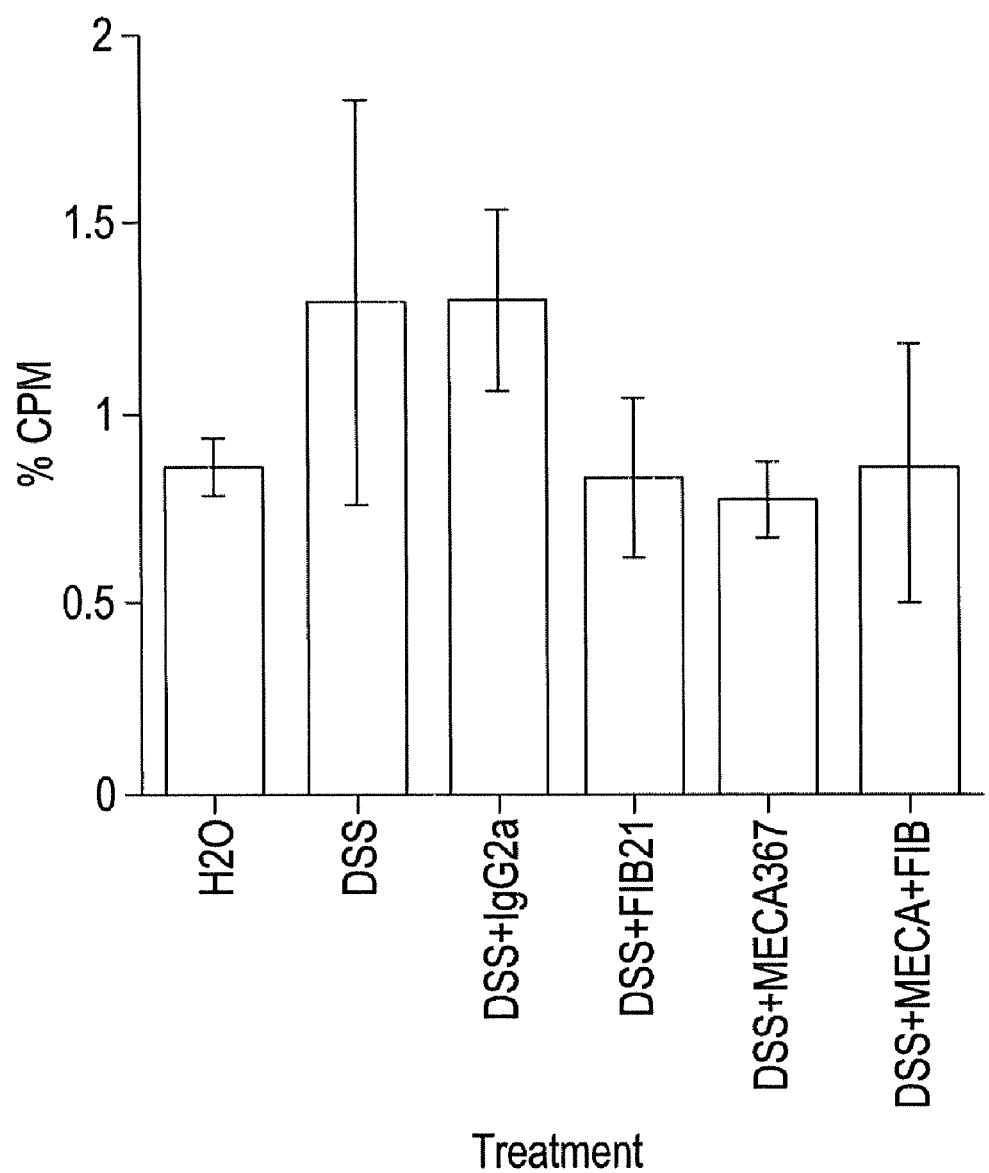
FIG. 8 is a graph of γ counts per minute (cpm) (±1 SEM) as a percentage of total input counts from mice given DSS in the drinking water for 10 days. Six groups consisted of negative controls given water alone, positive controls given DSS alone, test groups given irrelevant rat IgG2a antibody, FIB21, MECA-367, or FIB21 with MECA-367.

Lymphocyte recruitment to inflamed colon was then quantitatively assessed using radiolabeled mesenteric lymphocytes taken from syngeneic donors. One hour after injection of these cells in DSS-treated recipients, there was a trend towards a reduction in the number of $^{51}$Cr-labeled cells recruited to colon in mice that were treated with either β7-specific antibodies or the MAdCAM-specific antibodies, but not in mice treated with the isotype-matched control antibodies (FIG. 8).

B. Induction of Colitis in Scid Mice and Inhibition of Recruitment of Lymph Node Cells to Colon Scid mice reconstituted with CD45RB$^{hi}$ CD4$^+$ T cells develop colitis and a severe wasting syndrome. The colitis that develops in scid mice reconstituted with CD45RB$^{hi}$ CD4$^+$ T cells differs from most other murine models of IBD in that the induced colitis in the scid mouse clearly requires the presence of CD4$^+$ T cells for the induction, if not the pathogenesis, of the disease (Powrie, *Immunity*, 3:171 (1995), the teachings of which are incorporated herein in by reference their entirety)).

A modification of the method of Morrissey et al. and Powrie et al. (Morrissey et al., *J. Exp. Med.*, 178:237 (1993); Powrie et al., *Int. Imm.*, 5:1461 (1993), the teachings of which are both incorporated herein by reference in their entirety) was used to enrich for CD4+ T cells, isolated from BALB/c spleen, by depletion of granulytic leukocytes, CD8$^+$ T cells, B220$^+$ cells, I-A$^+$ cells and MAC-1$^+$ macrophages. CD45RB$^{hi}$ cells were selected by cell sorter, gating on the brightest 40-45% of CD4$^+$ cells stained with anti-CD45RB. Recipient scid mice were reconstituted by intravenous (i.v.) injection of 1×10$^6$ CD45RB$^{hi}$ or CD45RB$^{lo}$ T cells into the tail vein. Four mice were reconstituted with CD45RB$^{hi}$ T cells and four mice with CD45RB$^{lo}$ T cells.

Figure 18:
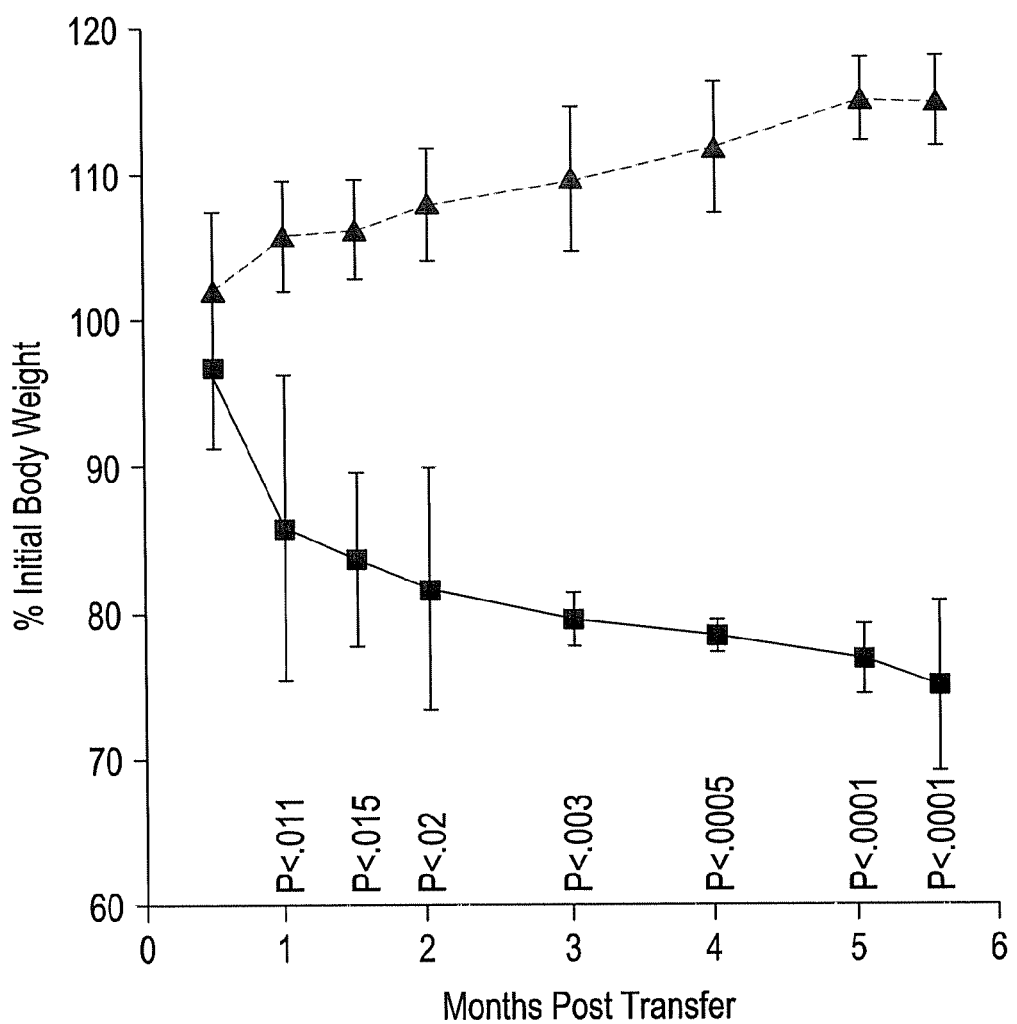
FIG. 18 is a graph illustrating the difference in body weight of scid mice reconstituted with $1\times10^6$ CD45RB$^{hi}$ T cells (■) relative to control scid mice reconstituted with an equal number of CD45RB$^{lo}$ T cells (▲) derived from BALB/c spleen. Recipient mice were weighed at weekly intervals to evaluate progression of disease.

Reconstituted mice were monitored weekly for changes in weight and the development of fecal occult blood. Typically, within 4-6 weeks post reconstitution, the difference in body weight of mice reconstituted with CD45RB$^{hi}$ T cells relative to control scid mice reconstituted with an equal number of CD45RB$^{lo}$ T cells, became statistically significant (FIG. 18).

Colitis can be induced in this model with as few and 5×10$^4$ cells. Generally, from 1-5×10$^5$ is used. Although the kinetics of onset of disease is not uniform among mice in a given reconstitution, the colitis is of similar severity once the body weight has decreased to 75-85% of initial weight. Histological observations were consistent with the reports of others, and indicate that the colitis in this model is characterized by massive infiltration of CD4$^+$ T cells in the mucosa and submucosa, epithelial immaturity, ulceration, crypt hyperplasia, loss of goblet cells and crypt abscesses. Similar to Crohn's Disease, the IBD in the scid model is also characterized by transmural infiltration with deep fistulas. Unlike the other murine models of colitis, the severity of the disease is not limited to the distal colon but is of equal severity in the transverse and proximal colon.

Antibody Blockade of β7 and MAdCAM Interactions

Anti-murine MAdCAM-1 antibody (MAb MECA-367; American Type Culture Collection (Rockville, Md.), Accession No. HB 9478; Streeter, P. R., et al., *Nature*, 331:41 (1988); see also, U.S. Pat. No. 5,403,919 to Butcher) and anti-murine β7 antibody (MAb FIB 504; Andrew, D. P., et al., *J. Immunol.*, 153: 3847 (1994)) were used in these studies.

scid mice were reconstituted with 2×10$^5$ CD45RB$^{hi}$ or CD45RB$^{lo}$ CD4+ T cells. Five months post-reconstitution, mice were injected for 14 days with 200 μg/day of Rat IgG2a control antibody or a mixture of 100 μg/day FIB-504 (murine β7-specific)+100 μg/day MECA-367 (murine MAdCAM-specific). Antibody was in PBS. There were five mice in each treatment group. After 14 days, mice were injected intravenously with 5×10$^6$ mesenteric lymph node cells (BALB/c) labeled with $^{111}$In-oxine. 24 hours after adoptive transfer of labeled cells, tissues were harvested and assessed for radioactivity. Background levels of radioactivity in tissues, contributed by non-specific trapping of cells, were assessed by injection of 5×10$^6$ labeled cells fixed with 2% PBS-buffered formaldehyde. Results were expressed as % counts per minute (CPM) in colon normalized to CPM in spleen and corrected for background.

Figure 19:
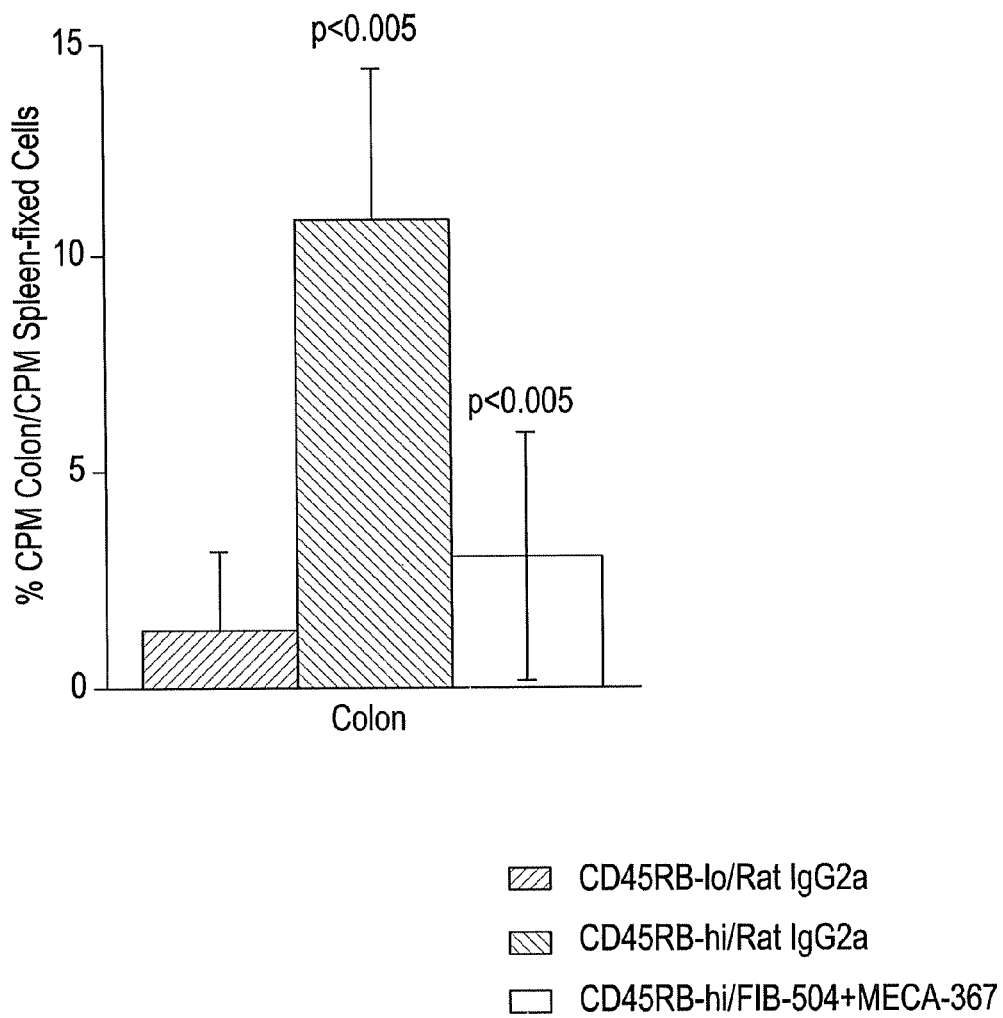
FIG. 19 is a histogram illustrating the increased accumulation in the colon of intravenously injected $^{111}$In-labeled mesenteric lymph node cells in scid mice reconstituted with CD45RB$^{hi}$ T cells as compared with the accumulation in colon of scid mice reconstituted with an equal number of CD45RB$^{hi}$ T cells, and the inhibition of accumulation by treatment for 2 weeks with a combination of anti-β7 (FIB 504) and anti-MAdCAM (MECA-367) monoclonal antibodies. Results are expressed as % counts per minute (CPM) in colon normalized to CPM in spleen and corrected for background.

This quantitative assessment of infiltration to the colon in scid mice reconstituted with CD45RB$^{hi}$ CD4+ T cells revealed an increase in localization of 10- to 100-fold as compared with the level observed in scid recipients reconstituted with an equal number of CD45RB$^{lo}$ CD4+ T cells. This increased accumulation of labeled cells in the colon was inhibited 50-75% by treatment for 2 weeks with a combination of anti-β7 and anti-MAdCAM monoclonal antibodies (FIG. 19).

In another experiment, scid mice were reconstituted with 5×10$^4$ CD45RB$^{hi}$ or CD45RB$^{lo}$ CD4$^+$ T cells. At the time of reconstitution, mice were treated with either (a) 500 μg of FIB 504 (β7-specific) (6 mice); (b) 500 μg MECA-367 (MAdCAM-specific) (3 mice); (c) 1 mg isotype-matched control antibody (7 mice); or (d) 1 mg FIB 504+MECA-367 (500 μg each) (5 mice). Following reconstitution, antibodies were administered at weekly intervals: (a) 250 μg FIB 504; (b) 250 μg MECA-367; (c) 500 μg isotype-matched control; or (d) 500 μg FIB 504+MECA-367 (250 μg each).

Figure 20:
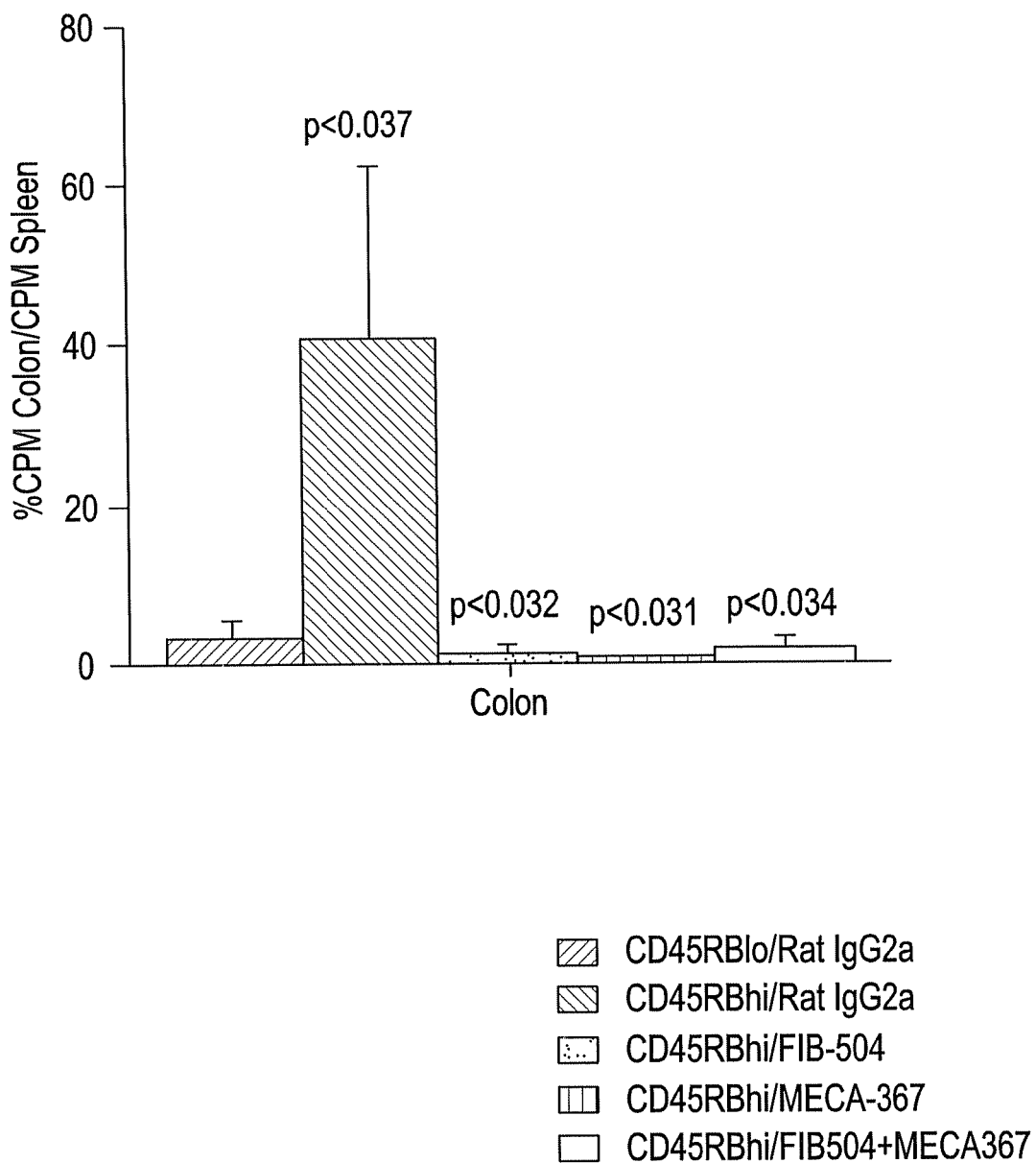
FIG. 20 is a histogram illustrating the complete inhibition accumulation of $^{111}$In-labeled cells (injected intravenously) in the colon of scid mice by treatment for 4 months (starting from the time of reconstitution) with FIB 504, MECA-367, or FIB 504 plus MECA-367. From left to right: scid mice reconstituted with CD45RB$^{lo}$ T cells, receiving irrelevant isotype-matched control rat IgG2a; scid mice reconstituted with CD45RB$^{hi}$ T cells, receiving either irrelevant isotype-matched control rat IgG2a, FIB 504, MECA-367, or FIB 504+MECA-367.

After 4 months of treatment, mice were injected with 5×10$^6$ $^{111}$In-labeled mesenteric lymph node cells (BALB/c), and recruitment to the colon was assessed by measuring levels of radioactivity. Results were calculated as described for FIG. 19. Treatment of scid mice for 4 months, starting from the time of reconstitution, with FIB 504 and MECA-367, alone or in combination, inhibited the increased recruitment of lymphocytes to the colon by 100% (FIG. 20).

scid mice were reconstituted with 2.0×10$^5$ to 4.0×10$^5$ CD45RB$^{hi}$ or CD45RB$^{lo}$ CD4$^+$ T cells. After 4 months, the mice were treated for 14 days with a combination of FIB 504 (β7-specific)+MECA-367 (MAdCAM-specific) (100 μg of each MAb per day for a total of 200 μg/day) or an isotype-matched control antibody (200 μg/day). Antibody was in PBS. Each experimental group consisted of 4 mice. Frozen sections of left and right colon were stained with a rat monoclonal antibody specific for mouse CD4 and developed with either Fast Red or AEC (3-amino-9-ethyl-carbazole) chromogen. One cross-section of left colon and right colon from each mouse was analyzed for positive staining for CD4 using a Leica Quantimet 500 Image analyzer. Each section was surveyed in its entirety using a 10× objective. Significance was determined using a students t-test. Data represents the mean positive count/tissue area±1 standard deviation.

Histological assessment by immunohistochemistry with a panel of antibodies specific for markers of cell lineage and state of differentiation, suggested that virtually all infiltrating cells in the colons of scid mice reconstituted with CD45RB$^{hi}$ T cells were CD4$^+$ T cells. No CD8+ T cells or B220$^+$ B cells could be identified under the conditions used. Further, treatment of these mice with a combination of β7- and MAdCAM-specific monoclonal antibodies significantly reduced the number of CD4$^+$ T cells in the ascending or descending colon relative to the controls (FIG. 21). As mesenteric lymph node cells are ~95% lymphocytes, these results indicate that the interaction of α4β7 on lymphocytes with MAdCAM is important in the recruitment of lymphoycytes to sites of inflammation in the colon and that agents which block this interaction can reduce inflammation.

Example 5

Resolution of Villus Alterations in the Common Marmoset (*Callithrix jacchus*) with Malabsorptive Enteritis Description of Model Common marmosets (*Callithrix jacchus*) are a new world nonhuman primate that, under captive conditions at the New England Regional Primate Research Center (NERPRC), develop a steroid-nonresponsive, spontaneous malabsorption syndrome characterized by weight loss, diarrhea, and small intestinal mucosal changes consistent with loss of absorptive capacity. These histologic changes include small intestinal villus atrophy and fusion, and a mononuclear leukocyte infiltrate within the lamina propria similar to Celiac disease (non-tropical sprue) in humans. Retrospective analysis from the pathology archive files at NERPRC demonstrated that up to 80% of common marmosets have, to various degrees, malabsorptive enteritis at the time of postmortem examination.

Antibody Therapy Protocol

Adult common marmosets were selected for study from the colony-at-large at NERPRC. Base-line studies on all animals included physical examination, complete blood count (CBC), blood chemistry profile, serum B12, c-reactive protein, and full-thickness jejunal biopsy by laparotomy. Following recovery from abdominal surgery, the animals were treated for 14 days with 2 mg/kg/day of ACT-1 monoclonal antibody, a blocking monoclonal antibody against a conformational epitope of $\alpha 4\beta 7$ (Schweighoffer, T., et al., *J. Immunol.* 151: 717-729, 1993). Previous studies indicated that this antibody cross-reacted to *Callithrix* $\alpha 4\beta 7$. All assessments that were performed prior to antibody therapy were repeated between the 10th and 14th day of antibody therapy.

Analysis of Jejunal Biopsies

Full-thickness jejunal biopsies from each marmoset were evaluated histologically by two independent pathologists, and villus architecture was scored according to the following grading criteria:

| | Villus atrophy |
|---|---|
| 0 | normal mucosal thickness and villus height |
| 1 | mild atrophy; slight shortening of villi; height approximately 75% of normal |
| 2 | moderate atrophy; villi approximately 33-50% normal height |
| 3 | severe atrophy; short (<33% normal) or no observable villi |
| | Villus fusion |
| 0 | normal; no fusion |
| 1 | 1-2 villi in specimen fused |
| 2 | Between 1-2 and 50% of villi in specimen fused |
| 3 | >50% villi in specimen fused |

Data Analysis

Differences between mean scores obtained for each group of animals were assessed for statistical significance using a paired Student's t-test. Differences between means were considered significant when P<0.05.

Results

Figure 9:
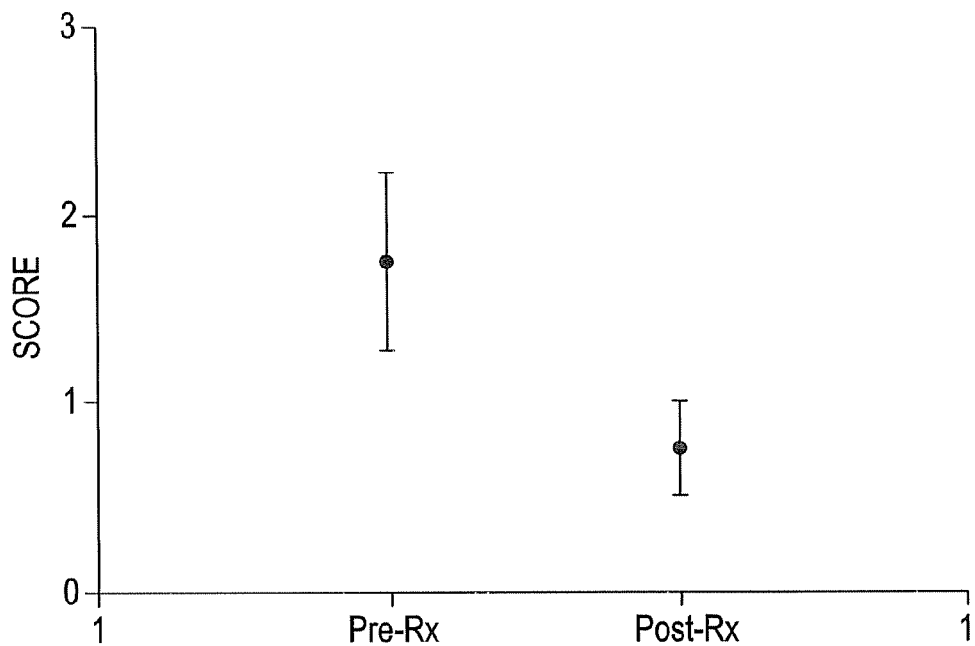
FIG. 9 is a graph depicting the histologic scores (±1 SEM) for villus fusion obtained from jejunal biopsy samples of common marmosets before and on the 14th day of treatment with 2 mg/kg/day of ACT-1 monoclonal antibody.
Figure 10:
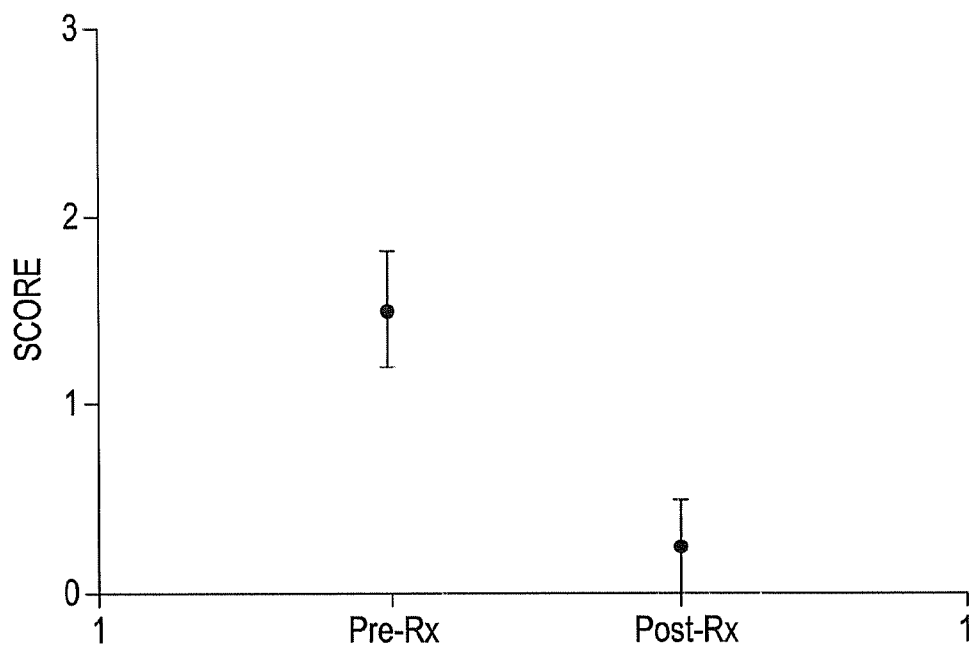
FIG. 10 is a graph depicting the histologic scores (±1 SEM) for villus atrophy obtained from jejunal biopsy samples of common marmosets before and on the 14th day of treatment with 2 mg/kg/day of ACT-1 monoclonal antibody.

The mean scores for villus fusion and atrophy before and after antibody therapy with the ACT-1 monoclonal antibody are shown in FIGS. 9 and 10, respectively. As demonstrated, there was almost complete resolution of villus atrophy (P<0.01) and a trend for improvement of villus fusion after a two-week course of therapy with the ACT-1 antibody. The effect was not secondary to nonspecific effects of exposure to foreign immunoglobulin since other animals treated with various monoclonal antibodies directed against epitopes other than that recognized by ACT-1 were ineffective in reducing villus fusion and atrophy scores.

Example 6

Resolution of Colitis in the Cotton Top Tamarin

Description of Model

The cotton-top tamarin (CTT) (*Saguinus oedipus*) is a New World nonhuman primate which develops spontaneous, and often chronic, colitis which is clinically and histologically similar to ulcerative colitis in man (Madara, J. L., et al., Gastroenterology, 88: 13-19 (1985)).

Immunotherapy, Clinical Assessment and Mucosal Biopsy

Figure 13:
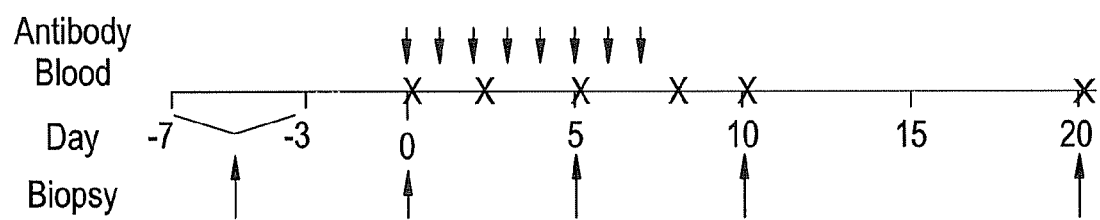
FIG. 13 is a diagram illustrating the experimental protocol for treatment of chronically colitic cotton-top tamarins with ACT-1 antibody.

An experimental protocol involving clinical assessment, colonic mucosal biopsy, and ACT-1 immunotherapy of colitic CTTs was instituted (FIG. 13). ACT-1 is a murine IgG1 monoclonal antibody reactive with human $\alpha 4\beta 7$ (Schweighoffer, T., et al., *J. Immunol.*, 151: 717-729 (1993); Lazarovits, A. I., et al., *J. Immunol.*, 133: 1857-1862 (1984); and Erle, D. J., et al., *J. Immunol.*, 153: 517-528 (1994)). ACT-1 was found to cross-react in the tamarin as assessed by immunohistologic staining with ACT-1 antibody of colitic mucosa from affected animals. These initial pilot studies demonstrated that from 40-80% of mononuclear cells within the lamina propria of colon from affected animals were $\alpha 4\beta 7+$, similar to human colitic mucosa. ACT-1 was also found to cross-react with $\alpha 4\beta 7$ from the CTT using flow cytometry on CTT peripheral blood lymphocytes (PBLs).

CTTs with chronic colitis were chosen from the colony-at-large at the New England Regional Primate Research Center, Southborough, Mass. based upon clinical observation of diarrhea and weight loss. To confirm the presence of colitis (as defined by a histologic inflammatory activity score of 2 or 3), colony animals noted to have clinical emaciation and diarrhea were evaluated for colonic inflammatory activity by routine histological assessment of colonic mucosal biopsy samples on multiple occasions prior to experimental assessment of antibody immunotherapy (FIG. 13). Chronically colitic CTTs were screened for colitis inflammatory activity on at least two occasions by examination of mucosal specimens from the terminal descending colon, 2-3 cm from the anus, using a pediatric fiberoptic endoscope. Inflammatory activity scores were based upon the relative numbers of neutrophils within the lamina propria, crypt lumena, crypt epithelium, and surface epithelium. In particular, a histopathologic scoring system of acute and chronic inflammatory activity was used (described by Madara, J. L., et al., *Gastroenterology*, 88: 13-19 (1985)). All biopsy samples were scored and categorized into four groups, with 0 representing normal mucosa and 3 representing the most severe and inflamed mucosa. Scores of 0 and 1 do not represent symptomatic colitis, while scores of 2 to 3 represent mild to severe colitic activity. Animals selected for study had: (1) moderate (grade 2) or severe (grade 3) structural alterations of surface and crypt epithelium on the first biopsy specimen, suggestive of colitis of a chronic nature, and (2) moderate (grade 2) or severe (grade 3) inflammatory activity on at least two biopsy samples taken 3-7 days apart prior to immunotherapy. Biopsy samples satisfying these criteria were characterized by the presence of crypt branching and/or loss with polymorphonuclear leukocyte (PMNs) infiltration to either the lamina propria and/or epithelial compartment.

Thus, animals selected for study had repeated evidence of colonic inflammatory activity and clinically-relevant colitis of a chronic nature with no recent evidence of remission. Moreover, persistence of diarrhea to the first day of administration of monoclonal antibody was requisite for the animal to be included in the study. Within 5 days of confirmation of colitis, the animals began immunotherapy with ACT-1 monoclonal antibody.

ACT-1 antibody was produced by culture in a hollow fiber cell fermenter using a sterile pyrogen-free flowpath, purified by protein A affinity chromatography, and diluted in sterile 0.9% NaCl prior to use in vivo. Because CTTs are an endangered species, ACT-1 was also demonstrated to cross-react to $\alpha 4\beta 7$ on PBLs from a related species, the common marmoset (*Callithrix jacchus*) in order to perform a pharmacokinetic analysis of the antibody prior to administration to colitic CTTs. In this component of the study, ACT-1 was administered to two normal adult common marmosets, first as a single intravenous infusion and then as a single intramuscular injection 24 hrs later. Intravenous administration of 2.0 mg/kg of ACT-1 in these animals yielded an estimated serum half life of approximately 50 hours, with continued absorption of antibody from 2-24 hours after a single intramuscular injection. Using this dosing regime, peak serum concentrations of antibody were approximately 60 µg/ml, while trough concentrations were $\geq 18.0$ µg/ml. No adverse clinical effects were observed in marmosets given ACT-1.

In view of these observations, half of the cotton top tamarins satisfying the study requirements (n=4; collective age=31 years) were given a single intravenous (I.V.) bolus of ACT-1 at a dose of 2.0 mg/kg the first day, and 7 subsequent intramuscular (I.M.) injections of the same amount every 24 hours, for a total of 8 days of immunotherapy. The other half of the chronically colitic control animals (n=4; collective age=26 years) received antibody 86D, a murine monoclonal antibody (IgG1) to sheep TCR $\gamma\delta$ (Mackay, C. R., et al., *Eur. J. Immunol.*, 19: 1477-1483 (1989)), which does not cross-react in CTTs (data not shown). This irrelevant, isotype-matched antibody was produced, purified, and administered under identical conditions as ACT-1.

Colonic mucosal biopsies were again obtained at the time of the first antibody infusion (Day 0) and on days 5, 10 and 20. The biopsies were evaluated by an independent pathologist. Additional colon biopsies were frozen for immunohistology. For histologic analyses, colonic mucosal biopsy specimens, taken 2-3 cm for the anus, were immediately snap-frozen in OCT compound, and duplicate samples taken from the adjacent area were fixed in 10% phosphate-buffered formalin, processed by routine histological techniques, embedded in paraffin, cut at a thickness of 6.0 µm, and sections stained with hematoxylin and eosin. The formalin-fixed samples were then examined histopathologically. Acetone-fixed, frozen sections were used to detect murine IgG1 administered in vivo by eliminating the primary antibody in the sequence of a previously described avidin-biotin peroxidase immunohistochemical technique (Ringler, D. J., et al., *Clin. Immunol. Immunopathol.*, 49: 349-364 (1988)).

Animal caretakers were blinded as to therapeutic regime (ACT-1 vs. isotype-matched irrelevant monoclonal antibody), and evaluated stool consistency in each animal on a daily basis by categorizing stool as diarrhea, semi-solid, or solid. Scores were assigned as follows: 0, formed, solid stool; 1, liquid stool with some solid components (semi-solid); or 2, liquid stool (diarrhea). Animals were weighed every other day, while blood was drawn at the same intervals for flow cytometry, hematology, and storage of serum or plasma for further analyses, such as antibody concentration, anti-mouse IgG titer, clinical chemistry, or acute phase proteins.

Computer-Assisted Morphometric Image Analysis

Quantitative, computer-assisted, morphometric analysis of mucosal biopsy sections was performed using a Leica Quantimet 500 Image Analyzer. First, immunohistochemical analysis of mucosal sections was performed to delineate specific leukocyte cell types using an avidin-biotin peroxidase technique, as previously described (Ringler, D. J., et al., *Clin. Immunol. Immunopathol.*, 49: 349-364 (1988)). Paraformaldehyde-, acetone-, or formalin-fixed, frozen sections were used to identify neutrophils, $\beta 7+$ cells, and monocyte/macrophages (M$\phi$), respectively, by using, as primary reagents in the sequence, a sheep anti-elastase polyclonal antibody (Biodesign, Kennebunk, Me.) to identify neutrophils, FIB21 monoclonal antibody (rat IgG2a) to identify the $\beta 7$ chain (Andrew, D. P., et al., *J. Immunol.*, 153: 3847-3861 (1994)), and HAM-56 monoclonal antibody (mouse IgM) to identify macrophages (Dako Corp., Carpinteria, Calif.). Examination of stained tissue sections using the elastase antibody documented that this reagent only recognized polymorphonuclear cells in CTT colonic mucosa. Formalin-fixed, paraffin-embedded tissue sections were used to enumerate T and B cells, using a rabbit polyclonal antibody to human CD3 (Dako Corp., Carpinteria, Calif.) and L26 monoclonal antibody (mouse IgG2a) (Dako Corp., Carpinteria, Calif.), respectively, as primary reagents in the sequence. For detection of primary antibodies, species- and isotype-specific secondary reagents were used in order to eliminate recognition of ACT-1 or irrelevant murine IgG1 antibody in tissues. After immunohistochemical procedures, each cell population was enumerated on 2-4 random fields/section of mucosa. Cells were selected based on the color wavelength generated from the brown diaminobenzidine reaction product, and color selection criteria were identical on all sections analyzed for each cell-specific marker. Because of frozen section morphology and the high relative density of $\beta 7+$ lymphocytes and macrophages, quantification of these cell types was evaluated as the immunoreactive fractional area of mucosa, while all other leukocyte cell types were enumerated as the cell number/mucosal area. The values were expressed as the mean ($\pm 1$ SEM) percent of the pretreatment (day 0) value within a treatment group, obtained by comparing the value from each animal's biopsy sample at a particular timepoint to the value obtained from the same animal at day 0. Thus, values less than 100% (shown in bold in Table 3 below) represent a decrease of leukocyte cell density compared to the pretreatment samples, while values greater than 100% represent an increase of mucosal leukocyte cell density. Significance was determined using a paired Student's t-test and comparing mean raw scores of cell density at a particular time point to those at pretreatment. Differences between means were considered significant when $P<0.05$.

Hematology and Flow Cytometry

Lymphocytes expressing $\alpha 4\beta 7$ integrin were enumerated by flow cytometry and the ACT-1 monoclonal antibody using methods previously described (Mackay, C. R., et al., *Eur. J. Immunol.*, 19: 1477-1483 (1989)). Because saturating serum concentrations of ACT-1 were achieved with the infusion protocol, exogenously-administered ACT-1 in the serum could be used to enumerate the number of $\alpha 4\beta 7+$ lymphocytes in the blood. Briefly, whole blood from each animal at each blood collection was analyzed by diluting 100 µl of EDTA-anticoagulated blood with PBS/10% rabbit serum/5% human AB serum for 20 min at 4° C. After removal of the blocking serum, in the case of animals treated with ACT-1, blood cells were directly incubated with either 100 μl of fluorescein-conjugated, rabbit anti-mouse IgG (Dako Corporation, Carpinteria, Calif.), or in the case of the animals given irrelevant antibody or pretreatment blood samples, ACT-1 was added to blood at 10 μg/ml followed then by the secondary antibody. For each sample, a minimum of 10,000 cells was analyzed. Routine blood cell counts and differential analyses were performed using a Baker 5000 hematology analyzer and appropriate gating for cotton-top tamarin red cells, white cells, and platelets. From the hematology analysis and flow cytometry results, absolute numbers of $\alpha 4\beta 7+$ lymphocytes per μl of blood were calculated.

Results/Progress

Serum Concentrations

Serum concentrations of ACT-1 and an irrelevant isotype-matched antibody were generally both $\geq 10$ μg/ml for the first 10 days of the study. On days 2-10 of the study, biotinylated ACT-1, used in whole blood at a concentration of 10 μg/ml, failed to significantly label peripheral lymphocytes as assessed by flow cytometry in animals treated with ACT-1, while on day 0 and in animals treated with an irrelevant antibody, the same antibody recognized between 70-90% of the peripheral lymphocyte pool, similar to the staining profile of ACT-1 on human lymphocytes. Collectively, these results suggested that the therapeutic protocol for ACT-1 in colitic CTTs resulted in saturation of the $\alpha 4\beta 7$ integrin on lymphocytes in the peripheral circulation.

The ability of ACT-1 to recognize extravascular $\alpha 4\beta 7^+$ cells within the lamina propria of colonic mucosa of colitic CTTs was also assessed. Immunohistochemical techniques were used to detect murine IgG1 in colonic mucosal biopsies from the study animals, and ACT-1 was observed on cell membranes of mononuclear cells within the lamina propria on all biopsy time points for the first 10 days of the study in animals treated with ACT-1, but not, as expected, from Day 0 prior to antibody infusion. No labeling of lamina propria cells was observed in animals given irrelevant antibody. Therefore, the dosing regime utilized in the study resulted in neutralizing serum concentrations of ACT-1, and concomitant extravascular recognition and labeling of immune cells within colitic mucosa. ACT-1 antibody localized to the target site, namely lymphocytes within the peripheral blood and specifically to the extravascular compartment within colitic mucosa.

Clinical Effect

All four test animals maintained either a grade 2 or 3 colitic inflammatory activity in both the pre-treatment and Day 0 biopsy samples, which for 3 animals was separated by 5 days. In addition, changes within the mucosal architecture of all four animals demonstrated that these four animals had colitis of a long-lasting nature. Therefore, all animals appeared to have a chronic disease course.

Histopathologic analysis of colonic mucosal biopsies was performed. The results from representative CTTs (animals Sgo 326-84 and Sgo 17-85) before and 5 days after immunotherapy with ACT-1 illustrated the therapeutic effect of ACT-1 immunotherapy on microscopic changes to the colonic mucosa in colitic CTTs. Prior to immunotherapy, there was a purulent exudate within the epithelial compartment and crypt lumen, epithelial immaturity characterized by loss of fully-differentiated goblet cells, and the lamina propria was expanded by a mononuclear and purulent inflammatory infiltrate (Sgo 326-84, muscularis mucosae). After ACT-1 immunotherapy, ACT-1 was localized to membranes of mononuclear cells within the lamina propria using immunohistochemical techniques (Sgo 17-85, muscularis mucosae), and the neutrophilic component of the inflammatory infiltrate had resolved, fully-differentiated goblet cells were observed, and the lamina propria were no longer expanded by mononuclear cells and/or neutrophils (Sgo 326-84).

Figure 14:
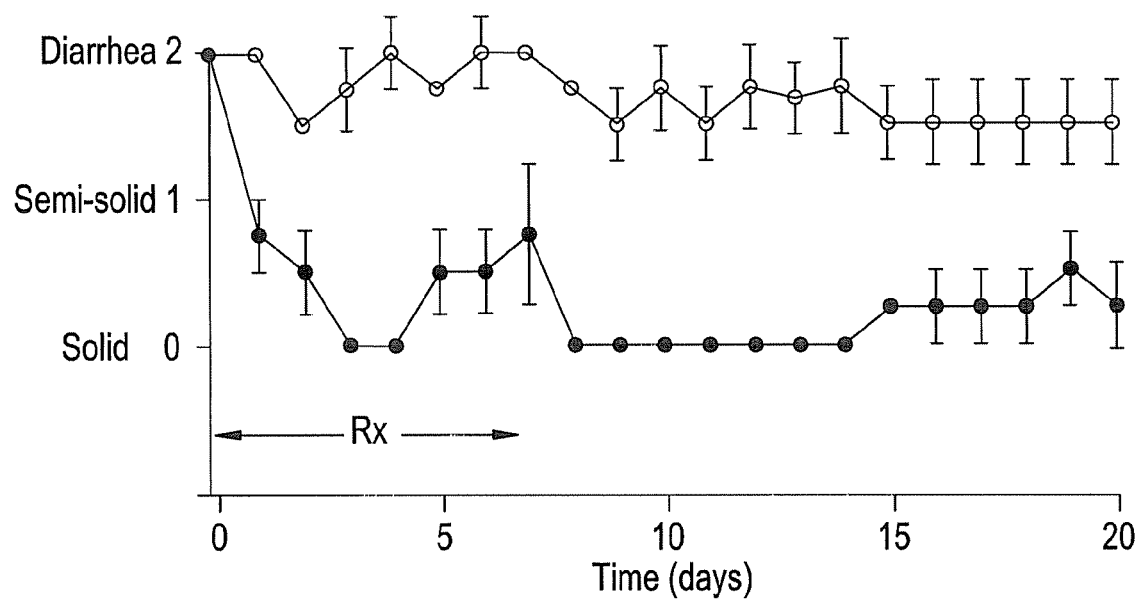
FIG. 14 is a graph illustrating the therapeutic effect on stool consistency of administration of ACT-1 antibody (-●-) or an irrelevant, isotype-matched antibody (-○-) to chronically colitic cotton-top tamarins.

The clinical effect of ACT-1 on stool consistency in colitic CTTs was striking (FIG. 14). An improvement in diarrhea to at least a semi-solid stool consistency was observed in all animals within 24 hours after the first dose, while complete resolution to solid stool occurred in all animals by 72 hours. Control animals did not improve and were observed to have diarrhea for the entire study period, showing, in addition, that the preselection criteria for this group of animals effectively eliminated those with spontaneous remissions.

Figure 11:
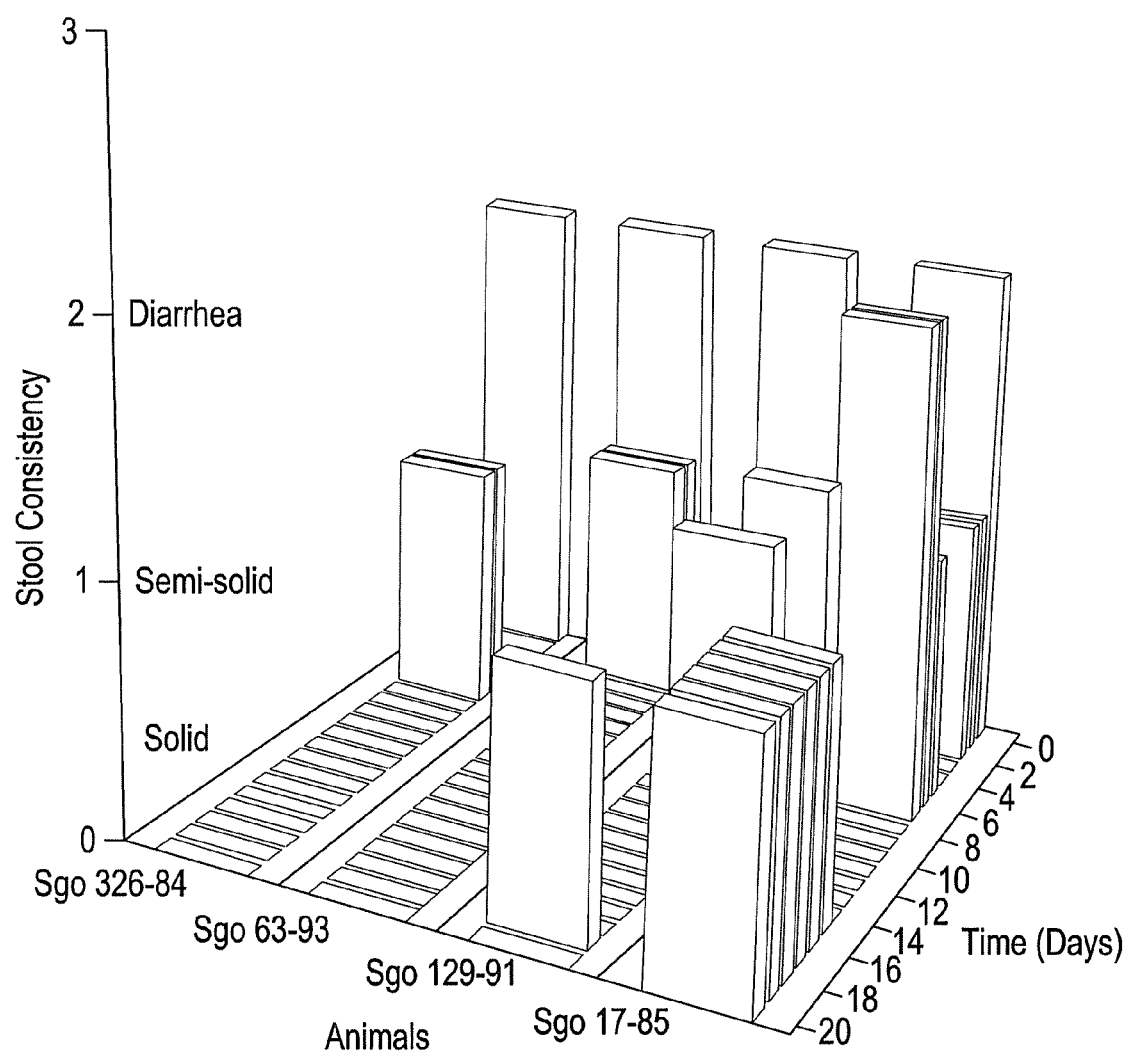
FIG. 11 is an illustration of the stool consistency of colitic animals (cotton-top tamarins) treated with ACT-1 antibody.

All animals maintained solid stools for approximately 1 week after termination of antibody injections (FIG. 11). With respect to individual animals, one animal (Sgo 63-93) had solid stool from Day 4 until the end of the protocol at Day 20 (FIG. 11). Two animals (Sgo 129-91 and Sgo 17-85) had slight relapses to semi-solid stools after Day 14 in the study (FIG. 11). The fourth animal (Sgo 326-84) showed a persistent improvement/resolution of diarrhea from Day 6 to Day 20.

Figure 15:
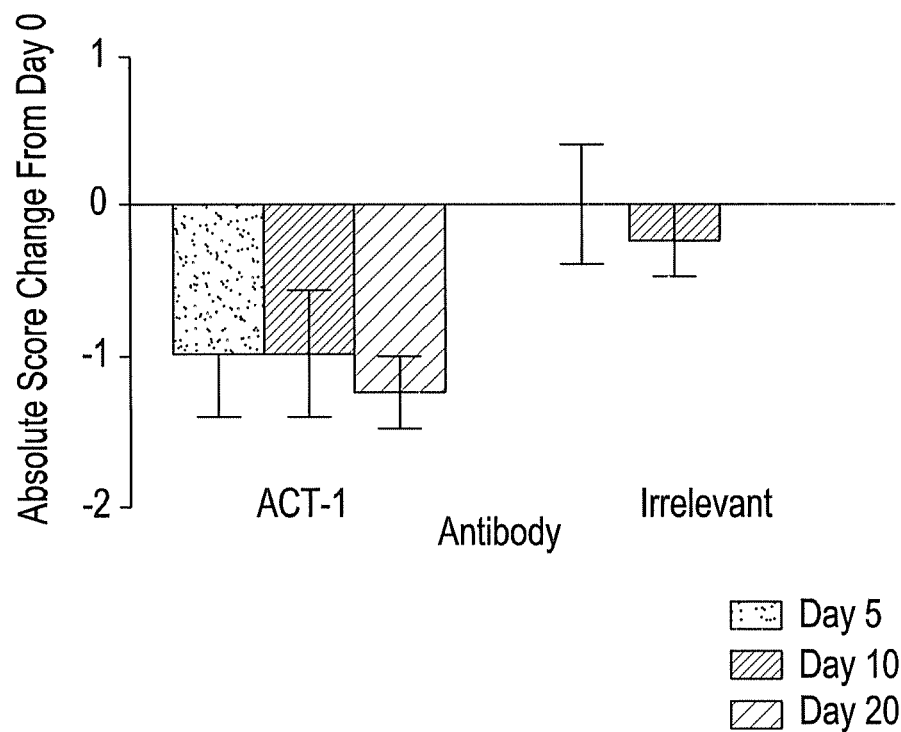
FIG. 15 is a histogram illustrating the therapeutic effect of ACT-1 immunotherapy on colonic inflammatory activity in chronically colitic colitic cotton-top tamarins treated with ACT-1 antibody or an irrelevant control monoclonal antibody. Each bar represents the mean within a treatment group of the absolute change in the inflammatory activity score ±1 SEM, computed for each animal by comparing the score at a particular time point with the same animal's score on Day 0.

Similarly, leukocyte infiltrates in the colon were markedly attenuated in CTTs given ACT-1. Compared to pretreatment biopsies, histologic analysis of colonic mucosa (formalin-fixed biopsy specimens of colonic mucosa) from animals treated with ACT-1 showed an improvement in inflammatory activity and associated structural alterations of the mucosa. Using a histologic scoring system of colonic inflammatory activity (Madara, J. L., et al., *Gastroenterology*, 88: 13-19 (1985)), animals treated with ACT-1 had marked decreases in inflammatory activity scores at all time points compared to baseline pretreatment scores, while scores from animals given the control antibody did not change (FIG. 15). There were no changes in inflammatory scores for the irrelevant treatment group on Day 20 (FIG. 15). Mean raw scores of inflammatory activity at all time points in the ACT-1-treated group were statistically lower than those from the same animals at Day 0 (Days 5 and 10, $P<0.05$; Day 20, $P<0.01$).

Figure 12:
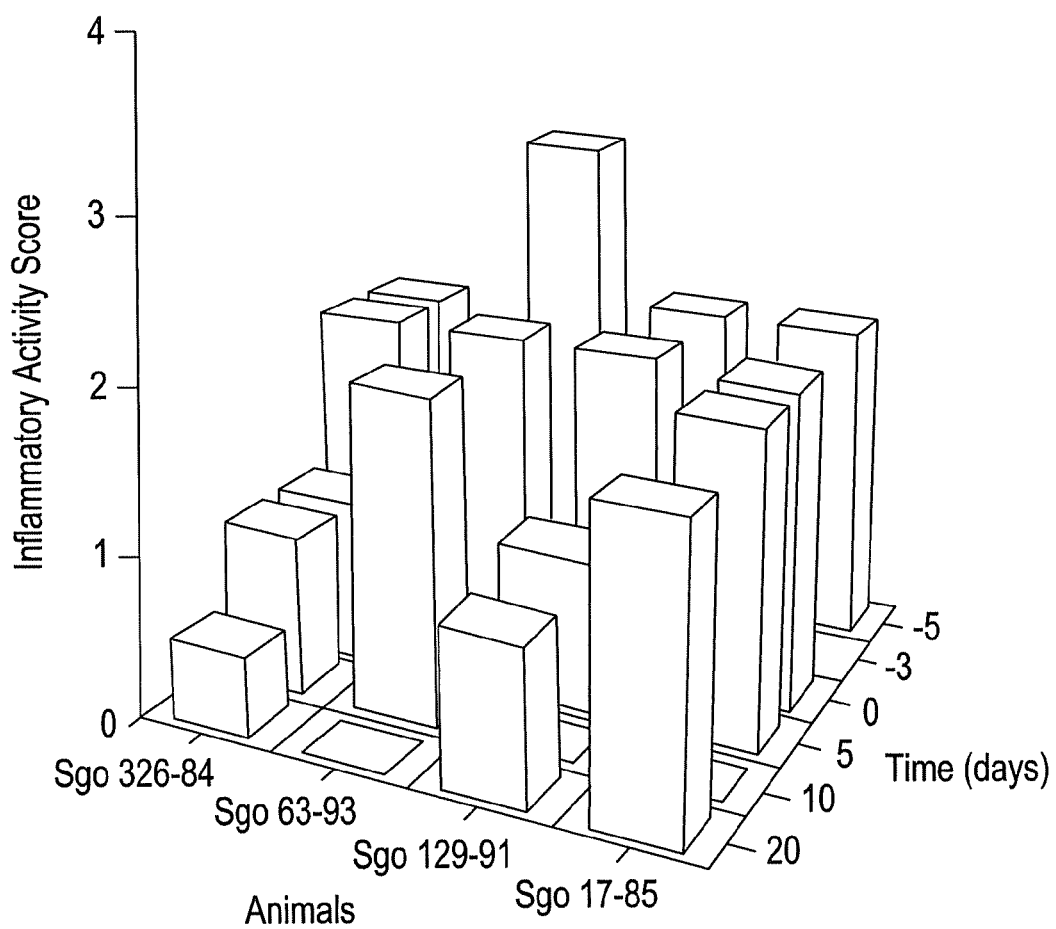
FIG. 12 is an illustration of the inflammatory activity in colitic animals (cotton-top tamarins) treated with ACT-1 antibody as assessed histologically.

With respect to individual animals, all four test animals showed improvement in inflammatory activity during or after ACT-1 immunotherapy. The colitis in two animals (Sgo 129-91 and Sgo 17-85) completely resolved by Day 10 (FIG. 12). Another animal (Sgo 63-93) did not show complete abrogation of colitis activity until Day 20 (FIG. 12), while mucosal biopsy scores from the fourth animal (Sgo 326-84) showed improvement during the entire study period (FIG. 12; two biopsies on day 20 in Sgo 326-84 were scored as 0 and 1). Furthermore, animal 326-84 gained 20% of its original body weight during the study period.

Figure 16:
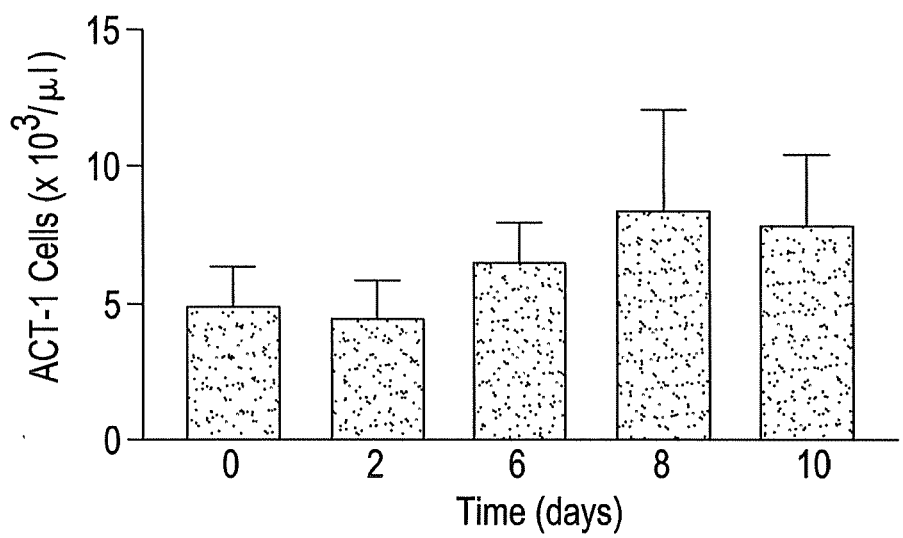
FIG. 16 is a histogram illustrating the absolute numbers of α4β7+ lymphocytes in the peripheral circulatory pool in colitic cotton-top tamarins treated with ACT-1 antibody. Each bar represents the mean (±1 SEM) of the concentration of α4β7+ cells in blood as detected by ACT-1.
Figure 17A:
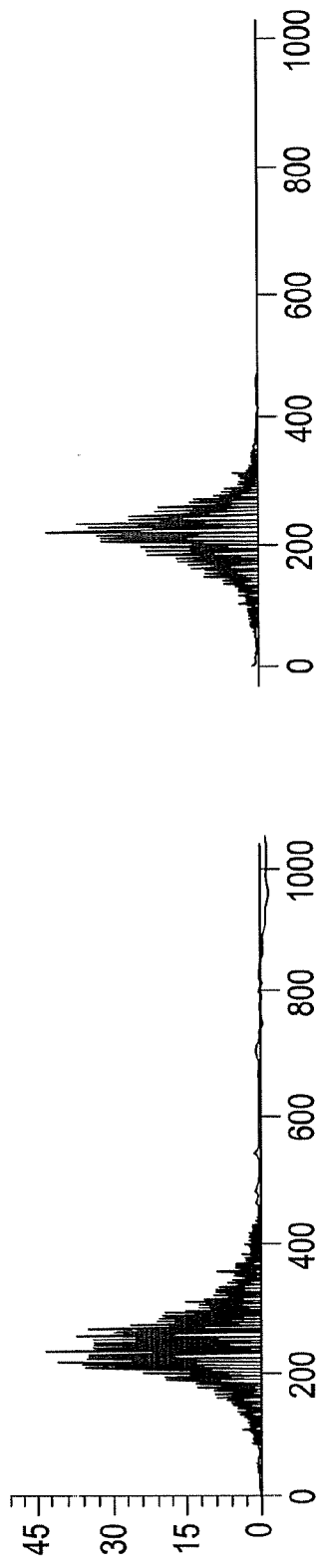
FIGS. 17A-17E are plots illustrating the results of a FACS analysis showing the specific staining of Hut 78 cells with MAdCAM-Ig chimeras. Supernatants from COS cells transiently transfected with a human MAdCAM-Ig chimeric constructs (from four independent transfections) were incubated with HuT 78 cells in the presence of 2 mM Mn++, and bound chimera was detected using a phycoerythrin-conjugated antibody specific for human IgG1.
Figure 17B:
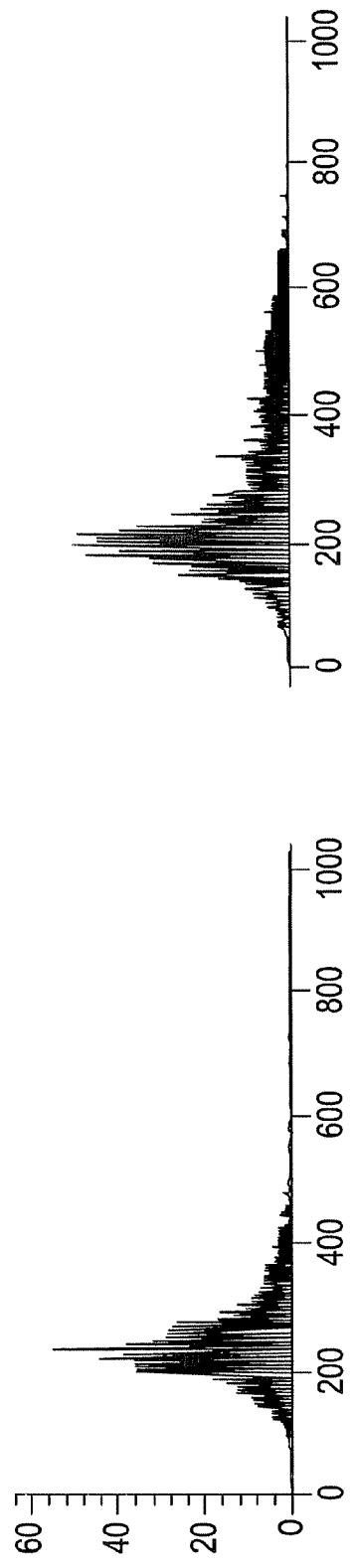
Figure 17C:
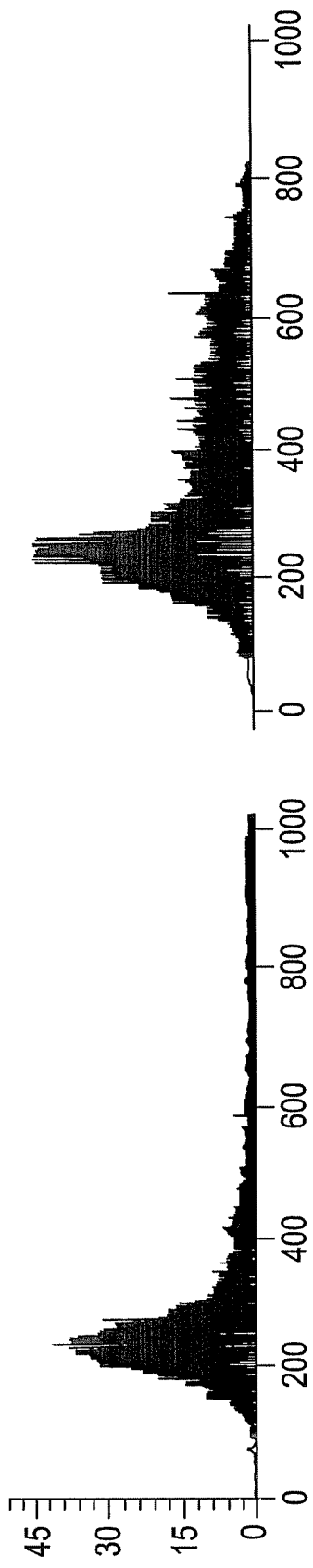
Figure 17D:
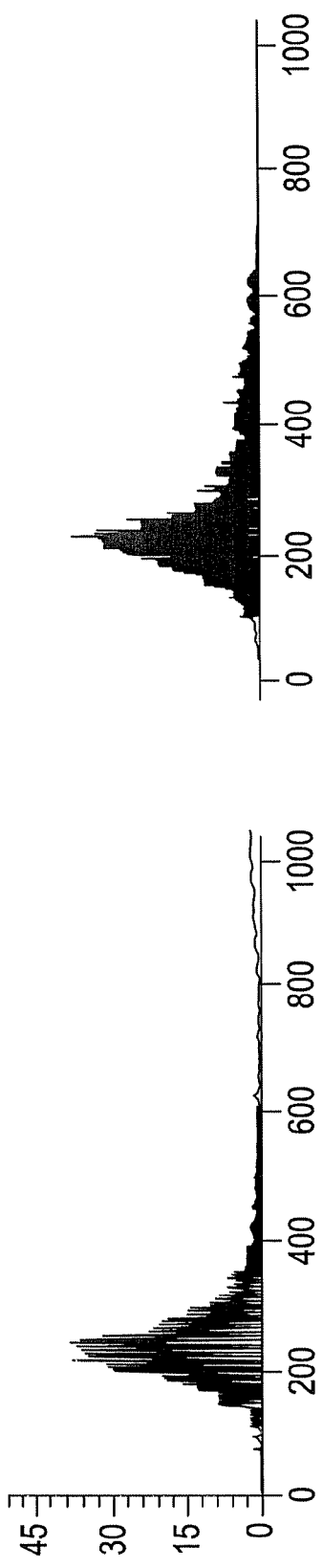
Figure 17E:
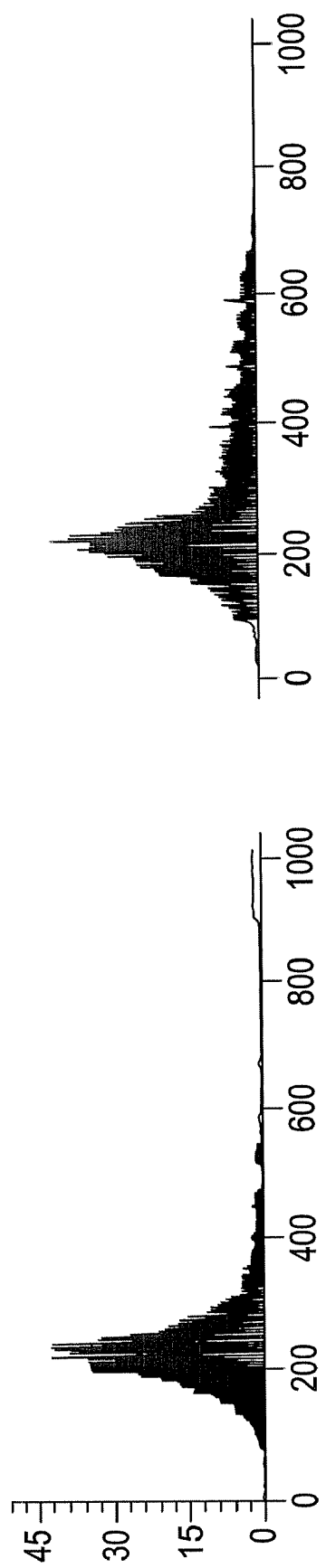

In order to provide a more quantitative assessment of efficacy, computer-assisted morphometric image analysis of leukocyte subsets within colonic mucosa from all study animals was performed. Table 3 illustrates the results of an analysis of the effect of ACT-1 immunotherapy on colonic inflammatory activity in chronically colitic CTTs (expressed as a percent of pretreatment values). ACT-1 immunotherapy resulted in significant reductions in the densities of mucosal leukocytes compared to baseline numbers established prior to antibody administration, while the control group generally had either similar or increased numbers of mucosal leukocytes after administration of irrelevant antibody. Ten days after the first dose of ACT-1 antibody, there were approximately 30% fewer mucosal mononuclear leukocytes expressing $\beta 7$ integrins compared to pretreatment values. This decrease was not attributed to decreases in the numbers of $\alpha 4\beta 7+$ lymphocytes in the peripheral circulatory pool (FIG. 16), nor was it related to manipulation or nonspecific effects since the numbers of β7+ leukocytes in colonic mucosa from the control animals either increased or remained largely unchanged. Similarly, mucosal T cells were reduced by approximately 50% at day 5 and by about 25% by day 10 in animals treated with ACT-1, while mucosal T cells in the irrelevant antibody group at the same time points did not change. Comparable reductions in mucosal B cells were seen in the ACT-1-treated group but not in the control group. Interestingly, ACT-1 immunotherapy also reduced the density of mucosal leukocytes which have either little or no expression of α4β7. Neutrophils were reduced by 40-45% at days 10 and 20 in animals treated with ACT-1, yet reductions in PMNs were not observed in the control group. Similarly, mucosal macrophages were reduced in all post-treatment biopsy samples by 30-45% in animals given ACT-1, while macrophages in the control group did not change. Interestingly, using immunohistochemistry and a cross-reactive monoclonal antibody specific for cloned human MAdCAM (10G3, Example 2), no change in expression was observed in colitic CTTs treated with ACT-1 or control antibody.

Summary

When administered to chronically colitic cotton-top tamarins, a monoclonal antibody to α4β7 integrin rapidly resolved diarrhea and colonic inflammatory activity, indicating efficacy in improving colitis. There appeared to be a good correlation between histologic inflammatory activity scores and stool consistency. The observation that stool consistency generally improved in 1-2 days in animals receiving ACT-1 antibody is noteworthy. Furthermore, the relative density of mucosal leukocyte subsets was greatly attenuated in response to immunotherapy with anti-α4β7 antibodies. These results also demonstrate an efficacious therapy for an inflammatory process which may be organ- or tissue specific (mucosal-specific).

The therapeutic effect of ACT-1 in colitic CTTs may be mediated by inhibition of lymphocyte recruitment to gut. Alternatively, or in addition, the therapeutic effect observed may reflect alterations in other cell interactions or signalling

TABLE 3

Quantitative analysis of leukocyte density in colonic mucosa of CTTs treated with ACT-1 or control monoclonal antibodies

| | ACT-1 | | | | | Irrelevant IgG1 | | | | |
|---|---|---|---|---|---|---|---|---|---|---|
| | PMNs | β7⁻ Cells | T Cells | B Cells | Mø | PMNs | β7⁺ Cells | T Cells | B Cells | Mø |
| Day 5 (%) | 83.0 ± 11.3 | 69.9 ± 12.0 | 50.4 ± 5.9 † | 53.1 ± 11.8† | 70.3 ± 6.4‡ | 75.7 ± 17.8 | 73.8 ± 10.0 | 104.0 ± 8.0 | 256.1 ± 67.7 | 141.8 ± 21.6 |
| Day 10 (%) | 57.5 ± 13.7† | 68.4± 7.1† | 75.9 ± 44.4§ | 82.1 ± 17.6 | 58.5 ± 4.3 † | 148.3 ± 49.3 | 118.8 ± 27.6 | 105.6 ± 9.6 | 357.0 ± 108.4 | 80.7± 9.8 |
| Day 20 (%) | 61.1 ± 11.4§ | 59.8 ± 12.6§ | 96.4 ± 10.4 | 61.3 ± 13.4§ | 58.5 ± 5.0§ | 339.6 ± 94.1 | 113.7 ± 28.1 | 72.4 ± 11.3† | 209.0 ± 51.0 | 174.5 ± 48.0 |

† $P < 0.05$;

‡ $P < 0.02$;

§ $P < 0.01$;

†$P < 0.001$.

No overt toxicity was observed in the study animals that could be attributed to ACT-1 administration. None of the study animals showed changes in clinical chemistry assessments of liver and renal function (data not shown). The ACT-1 antibody is a nonlytic monoclonal reagent (Lazarovits, A. I., et al., *J. Immunol.*, 133: 1857-1862 (1984)), and leukopenia was not observed in any animal during the study. Indeed, there was a trend for neutrophilia (peak numbers in peripheral blood approaching $40 \times 10^3/\mu l$; CTT normal range is 1.4-$12.0 \times 10^3/\mu l$) in all study animals, including the control animals, during the first week of study when daily anesthesia/manipulation was used to administer the antibodies. There was also a trend for lymphocytosis in the animals given ACT-1, with absolute numbers of lymphocytes in peripheral blood approaching $18 \times 10^3/\mu l$ (CTT normal range is $0.6$-$5.7 \times 10^3/\mu l$). Therefore, decreased recruitment of any leukocyte cell type to the colon in the ACT-1-treated group could not be attributed to changes in the number of leukocytes in the peripheral circulatory pool.

events mediated by α4β7 integrin. These results indicate that ACT-1 antibody is an effective antagonist of α4β7 integrin function, and that inhibition of α4β7 integrin function can be an organ- or tissue-specific treatment modality in the clinical management of individuals with inflammatory bowel disease. Further, the results indicate a role for α4β7 integrin in the pathogenesis of inflammatory bowel disease. α4β7 integrin provides a potentially organ-specific, therapeutic target for inflammatory bowel disease.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A fusion protein comprising a naturally occurring primate MAdCAM, wherein said naturally occurring primate MAdCAM binds α4β7 integrin and has at least about 75% amino acid sequence similarity to an amino acid sequence selected from the group consisting of SEQ ID NO:2, SEQ ID NO:4 and SEQ ID NO:6.

2. The fusion protein of claim 1, comprising a first moiety and a second moiety, wherein said first moiety is a naturally occurring primate MAdCAM and said second moiety is at least a portion of an immunoglobulin chain.

3. The fusion protein of claim 2, wherein said first moiety is joined at its C-terminal end to the N-terminal end of the second moiety.

4. The fusion protein of claim 2, wherein the second moiety is at least a portion of an immunoglobulin heavy chain constant region.

5. The fusion protein of claim 4, wherein the immunoglobulin heavy chain is of the IgG class.

6. The fusion protein of claim 4, wherein the second moiety comprises hinge, CH2 and CH3 domains of an immunoglobulin heavy chain.

7. A hybrid immunoglobulin comprising a fusion protein of claim 2.

8. The hybrid immunoglobulin of claim 7, wherein said hybrid immunoglobulin is a homodimer.

9. The fusion protein of claim 1, comprising a first moiety and a second moiety, wherein said first moiety is a naturally occurring primate MAdCAM and said second moiety is at least a portion of a mutant immunoglobulin chain, said mutant having reduced binding affinity for Fc receptor and/or complement relative to wild type immunoglobulin.

10. The fusion protein of claim 1 wherein said primate MAdCAM is encoded by SEQ ID NO:1, SEQ ID NO:3 or SEQ ID NO:5 or a nucleic acid that shares at least about 75% nucleotide sequence similarity with SEQ ID NO:1, SEQ ID NO:3 or SEQ ID NO:5.

11. The fusion protein of claim 1 wherein said primate MAdCAM is encoded by SEQ ID NO:1, SEQ ID NO:3 or SEQ ID NO:5 or a nucleic acid that shares at least about 90% nucleotide sequence similarity with SEQ ID NO:1, SEQ ID NO:3 or SEQ ID NO:5.

12. A fusion protein comprising an α4β7 integrin-binding fragment of a naturally occurring primate MAdCAM, wherein said primate MAdCAM has at least about 75% amino acid sequence similarity to an amino acid sequence selected from the group consisting of SEQ ID NO:2, SEQ ID NO:4 and SEQ ID NO:6, and said α4β7 integrin-binding fragment comprises the N-terminal immunoglobulin-like domain of said primate MAdCAM.

13. The fusion protein of claim 12 wherein said α4β7 integrin-binding fragment is selected from the group consisting of a fragment comprising the entire extracellular domain of primate MAdCAM and a fragment comprising the two N-terminal immunoglobulin domains of primate MAdCAM.

14. A hybrid immunoglobulin comprising a fusion protein of claim 12.

15. The hybrid immunoglobulin of claim 14, wherein said hybrid immunoglobulin is a homodimer.

16. A fusion protein comprising a naturally occurring human MAdCAM, wherein said naturally occurring human MAdCAM binds α4β7 integrin and has at least about 75% amino acid sequence similarity to SEQ ID NO:2 or SEQ ID NO:4.

17. The fusion protein of claim 16 wherein said human MAdCAM is encoded by SEQ ID NO:1, SEQ ID NO:3 or a nucleic acid that shares at least about 75% nucleotide sequence similarity with SEQ ID NO:1 or SEQ ID NO:3.

18. The fusion protein of claim 16 wherein said human MAdCAM is encoded by SEQ ID NO:1, SEQ ID NO:3 or a nucleic acid that shares at least about 90% nucleotide sequence similarity with SEQ ID NO:1 or SEQ ID NO:3.

19. The fusion protein of claim 18, comprising a first moiety and a second moiety, wherein said first moiety is a human MAdCAM and said second moiety is at least a portion of a mutant immunoglobulin chain, said mutant having reduced binding affinity for Fc receptor and/or complement relative to wild type immunoglobulin.

20. A hybrid immunoglobulin comprising a fusion protein of claim 16.

21. The hybrid immunoglobulin of claim 20, wherein said hybrid immunoglobulin is a homodimer.

22. A fusion protein comprising an $\alpha 4\beta 7$ integrin-binding fragment of a naturally occurring human MAdCAM, wherein said naturally occurring human MAdCAM binds $\alpha 4\beta 7$ integrin and has at least about 75% amino acid sequence similarity to SEQ ID NO:2 or SEQ ID NO:4, and said $\alpha 4\beta 7$ integrin-binding fragment comprises the two N-terminal immunoglobulin-like domains of said human MAdCAM.

23. The fusion protein of claim 22, wherein said $\alpha 4\beta 7$ integrin-binding fragment is selected from the group consisting of a fragment comprising the entire extracellular domain of human MAdCAM and a fragment comprising the two N-terminal immunoglobulin domains of human MAdCAM.

24. A hybrid immunoglobulin comprising a fusion protein of claim 22.

25. The hybrid immunoglobulin of claim 24, wherein said hybrid immunoglobulin is a homodimer.

26. A fusion protein comprising a primate MAdCAM moiety, wherein said primate MAdCAM moiety has binding affinity for $\alpha 4\beta 7$ integrin and comprises an amino acid sequence selected from the group consisting of SEQ ID NO:2 and the amino acid sequence of an $\alpha 4\beta 7$ integrin-binding portion of the polypeptide shown in FIG. 1 (SEQ ID NO:2), wherein said $\alpha 4\beta 7$ integrin-binding portion comprises the N-terminal immunoglobulin-like domain.

27. The fusion protein of claim 26 wherein said $\alpha 4\beta 7$ integrin-binding portion is a mature protein.

28. The fusion protein of claim 26 wherein said $\alpha 4\beta 7$ integrin-binding portion is the complete extracellular domain of the polypeptide shown in FIG. 1 (SEQ ID NO:2).

29. The fusion protein of claim 26 wherein said $\alpha 4\beta 7$ integrin-binding portion consists of the two amino-terminal immunoglobulin domains of the polypeptide shown in FIG. 1 (SEQ ID NO:2).

30. The fusion protein of claim 26 further comprising a second moiety, wherein said second moiety is at least a portion of an immunoglobulin chain.

31. A fusion protein comprising a primate MAdCAM moiety, wherein said primate MAdCAM moiety has binding affinity for $\alpha 4\beta 7$ integrin and comprises an amino acid sequence selected from the group consisting of SEQ ID NO:4 and the amino acid sequence of an $\alpha 4\beta 7$ integrin-binding portion of the polypeptide shown in FIG. 2 (SEQ ID NO:4), wherein said $\alpha 4\beta 7$ integrin-binding portion comprises the N-terminal immunoglobulin-like domain.

32. The fusion protein of claim 31 wherein said $\alpha 4\beta 7$ integrin-binding portion is a mature protein.

33. The fusion protein of claim 31 wherein said $\alpha 4\beta 7$ integrin-binding portion consists of the complete extracellular domain of the polypeptide shown in FIG. 2 (SEQ ID NO:4).

34. The fusion protein of claim 31 wherein said $\alpha 4\beta 7$ integrin-binding portion is the two amino-terminal immunoglobulin domains of the polypeptide shown in FIG. 2 (SEQ ID NO:4).

35. The fusion protein of claim 31 further comprising a second moiety, wherein said second moiety is at least a portion of an immunoglobulin chain.

36. A fusion protein comprising a naturally occurring primate MAdCAM, wherein said naturally occurring primate MAdCAM binds $\alpha 4\beta 7$ integrin and has at least about 90% amino acid sequence similarity to an amino acid sequence selected from the group consisting of SEQ ID NO:2, SEQ ID NO:4 and SEQ ID NO:6.

37. The fusion protein of claim 36, comprising a first moiety and a second moiety, wherein said first moiety is the naturally occurring primate MAdCAM and said second moiety is at least a portion of an immunoglobulin chain.

38. The fusion protein of claim 37, wherein said first moiety is joined at its C-terminal end to the N-terminal end of the second moiety.

39. The fusion protein of claim 37, wherein the second moiety is at least a portion of an immunoglobulin heavy chain constant region.

40. The fusion protein of claim 39, wherein the immunoglobulin heavy chain is of the IgG class.

41. The fusion protein of claim 39, wherein the second moiety comprises hinge, CH2 and CH3 domains of an immunoglobulin heavy chain.

42. A hybrid immunoglobulin comprising a fusion protein of claim 37.

43. The hybrid immunoglobulin of claim 42, wherein said hybrid immunoglobulin is a homodimer.

44. The fusion protein of claim 36 wherein said primate MAdCAM is encoded by SEQ ID NO:1, SEQ ID NO:3 or SEQ ID NO:5 or a nucleic acid that shares at least about 90% nucleotide sequence similarity with SEQ ID NO:1, SEQ ID NO:3 or SEQ ID NO:5.

45. A fusion protein comprising an $\alpha 4\beta 7$ integrin-binding fragment of a naturally occurring primate MAdCAM, wherein said naturally occurring primate MAdCAM has at least about 90% amino acid sequence similarity to SEQ ID NO:2, SEQ ID NO:4 or SEQ ID NO:6, and said $\alpha 4\beta 7$ integrin-binding fragment comprises at least one immunoglobulin-like domain of said primate MAdCAM.

46. The fusion protein of claim 45, wherein said $\alpha 4\beta 7$ integrin-binding fragment is selected from the group consisting of a fragment comprising the extracellular domain of said naturally occurring primate MAdCAM and a fragment comprising the two N-terminal immunoglobulin domains of said naturally occurring primate MAdCAM.

47. A hybrid immunoglobulin comprising a fusion protein of claim 45.

48. The hybrid immunoglobulin of claim 47, wherein said hybrid immunoglobulin is a homodimer.

49. A fusion protein comprising a naturally occurring human MAdCAM, wherein said naturally occurring human MAdCAM binds $\alpha 4\beta 7$ integrin and has at least about 90% amino acid sequence similarity to SEQ ID NO:2 or SEQ ID NO:4.

50. The fusion protein of claim 49 wherein said human MAdCAM is encoded by SEQ ID NO:1, SEQ ID NO:3 or a nucleic acid that shares at least about 90% nucleotide sequence similarity with SEQ ID NO:1 or SEQ ID NO:3.

51. The fusion protein of claim 49, comprising a first moiety and a second moiety, wherein said first moiety is a human MAdCAM and said second moiety is at least a portion of a mutant immunoglobulin chain, said mutant having reduced binding affinity for Fc receptor and/or complement relative to wild type immunoglobulin.

52. A hybrid immunoglobulin comprising a fusion protein of claim 49.

53. The hybrid immunoglobulin of claim 52, wherein said hybrid immunoglobulin is a homodimer.

54. A fusion protein comprising an α4β7 integrin-binding fragment of a naturally occurring human MAdCAM, wherein said naturally occurring human MAdCAM binds α4β7 integrin and has at least about 90% amino acid sequence similarity to SEQ ID NO:2 or SEQ ID NO:4, and said α4β7 integrin-binding fragment comprises the two N-terminal immunoglobulin-like domains of said human MAdCAM.

55. A hybrid immunoglobulin comprising a fusion protein of claim 54.

56. The hybrid immunoglobulin of claim 55, wherein said hybrid immunoglobulin is a homodimer.

57. A fusion protein comprising a primate MAdCAM or α4β7 integrin-binding fragment thereof, wherein said primate MAdCAM binds α4β7 integrin and has at least about 90% amino acid sequence similarity to an amino acid sequence selected from the group consisting of SEQ ID NO:2, SEQ ID NO:4, and said α4β7 integrin-binding fragment comprises at lease one immunoglobulin-like domain of said primate MAdCAM.

58. The fusion protein of claim 57, wherein said primate MAdCAM binds α4β7 integrin and has at least about 90% amino acid sequence similarity to SEQ ID NO:2.

59. The fusion protein of claim 57, wherein said primate MAdCAM binds α4β7 integrin and has at least about 90% amino acid sequence similarity to SEQ ID NO:4.

60. The fusion protein of claim 57, wherein said α4β7 integrin-binding fragment is selected from the group consisting of a fragment comprising the extracellular domain of said primate MAdCAM and a fragment comprising the two N-terminal immunoglobulin domains of said primate MAdCAM.

* * * * *

UNITED STATES PATENT AND TRADEMARK OFFICE
CERTIFICATE OF CORRECTION

| | | |
|---|---|---|
| PATENT NO. | : 7,803,904 B2 | Page 1 of 1 |
| APPLICATION NO. | : 08/875849 | |
| DATED | : September 28, 2010 | |
| INVENTOR(S) | : Michael J. Briskin et al. | |

It is certified that error appears in the above-identified patent and that said Letters Patent is hereby corrected as shown below:

Title Page, Item (54) and at Column 1, line 1, in the title, "Addressing" should read --addressins--

Claim 57

Column 76, line 5, delete "lease" and insert --least--

Signed and Sealed this
Fourteenth Day of June, 2011

David J. Kappos
*Director of the United States Patent and Trademark Office*

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
       (A) LENGTH: 1624 base pairs
       (B) TYPE: nucleic acid
       (C) STRANDEDNESS: double
       (D) TOPOLOGY: linear (ii) MOLECULE TYPE: cDNA (ix) FEATURE:
       (A) NAME/KEY: CDS
       (B) LOCATION: 1..1218

(xi) SEQUENCE DESCRIPTION: SEQ ID NO: 1:

```
ATG GAT TTC GGA CTG GCC CTC CTG CTG GCG GGG CTT CTG GGG CTC CTC        48
Met Asp Phe Gly Leu Ala Leu Leu Leu Ala Gly Leu Leu Gly Leu Leu
 1               5                  10                  15

CTC GGC CAG TCC CTC CAG GTG AAG CCC CTG CAG GTG GAG CCC CCG GAG        96
Leu Gly Gln Ser Leu Gln Val Lys Pro Leu Gln Val Glu Pro Pro Glu
                20                  25                  30

CCG GTG GTG GCC GTG GCC TTG GGC GCC TCG CGC CAG CTC ACC TGC CGC       144
Pro Val Val Ala Val Ala Leu Gly Ala Ser Arg Gln Leu Thr Cys Arg
         35                  40                  45

CTG GCC TGC GCG GAC CGC GGG GCC TCG GTG CAG TGG CGG GGC CTG GAC       192
Leu Ala Cys Ala Asp Arg Gly Ala Ser Val Gln Trp Arg Gly Leu Asp
 50                  55                  60

ACC AGC CTG GGC GCG GTG CAG TCG GAC ACG GGC CGC AGC GTC CTC ACC       240
Thr Ser Leu Gly Ala Val Gln Ser Asp Thr Gly Arg Ser Val Leu Thr
 65                  70                  75                  80

GTG CGC AAC GCC TCG CTG TCG GCG GCC GGG ACC CGC GTG TGC GTG GGC       288
Val Arg Asn Ala Ser Leu Ser Ala Ala Gly Thr Arg Val Cys Val Gly
                 85                  90                  95

TCC TGC GGG GGC CGC ACC TTC CAG CAC ACC GTG CAG CTC CTT GTG TAC       336
Ser Cys Gly Gly Arg Thr Phe Gln His Thr Val Gln Leu Leu Val Tyr
        100                 105                 110

GCC TTC CCG GAC CAG CTG ACC GTC TCC CCA GCA GCC CTG GTG CCT GGT       384
Ala Phe Pro Asp Gln Leu Thr Val Ser Pro Ala Ala Leu Val Pro Gly
        115                 120                 125

GAC CCG GAG GTG GCC TGT ACG GCC CAC AAA GTC ACG CCC GTG GAC CCC       432
Asp Pro Glu Val Ala Cys Thr Ala His Lys Val Thr Pro Val Asp Pro
130                 135                 140

AAC GCG CTC TCC TTC TCC CTG CTC GTC GGG GGC CAG GAA CTG GAG GGG       480
Asn Ala Leu Ser Phe Ser Leu Leu Val Gly Gly Gln Glu Leu Glu Gly
145                 150                 155                 160

GCG CAA GCC CTG GGC CCG GAG GTG CAG GAG GAG GAG GAG CCC CAG           528
Ala Gln Ala Leu Gly Pro Glu Val Gln Glu Glu Glu Glu Pro Gln
                165                 170                 175

GGG GAC GAG GAC GTG CTG TTC AGG GTG ACA GAG CGC TGG CGG CTG CCG       576
Gly Asp Glu Asp Val Leu Phe Arg Val Thr Glu Arg Trp Arg Leu Pro
                180                 185                 190

CCC CTG GGG ACC CCT GTC CCG CCC GCC CTC TAC TGC CAG GCC ACG ATG       624
Pro Leu Gly Thr Pro Val Pro Pro Ala Leu Tyr Cys Gln Ala Thr Met
            195                 200                 205

AGG CTG CCT GGC TTG GAG CTC AGC CAC CGC CAG GCC ATC CCC GTC CTG       672
Arg Leu Pro Gly Leu Glu Leu Ser His Arg Gln Ala Ile Pro Val Leu
        210                 215                 220
```

-continued

| | | |
|---|---|---|
| CAC AGC CCG ACC TCC CCG GAG CCT CCC GAC ACC ACC TCC CCG GAG CCT<br>His Ser Pro Thr Ser Pro Glu Pro Pro Asp Thr Thr Ser Pro Glu Pro<br>225                              230                            235                          240 | 720 |
| CCC AAC ACC ACC TCC CCG GAG TCT CCC GAC ACC ACC TCC CCG GAG TCT<br>Pro Asn Thr Thr Ser Pro Glu Ser Pro Asp Thr Thr Ser Pro Glu Ser<br>                          245                            250                            255 | 768 |
| CCC GAC ACC ACC TCC CAG GAG CCT CCC GAC ACC ACC TCC CAG GAG CCT<br>Pro Asp Thr Thr Ser Gln Glu Pro Pro Asp Thr Thr Ser Gln Glu Pro<br>                260                            265                            270 | 816 |
| CCC GAC ACC ACC TCC CAG GAG CCT CCC GAC ACC ACC TCC CCG GAG CCT<br>Pro Asp Thr Thr Ser Gln Glu Pro Pro Asp Thr Thr Ser Pro Glu Pro<br>275                              280                            285 | 864 |
| CCC GAC AAG ACC TCC CCG GAG CCC GCC CCC CAG CAG GGC TCC ACA CAC<br>Pro Asp Lys Thr Ser Pro Glu Pro Ala Pro Gln Gln Gly Ser Thr His<br>290                              295                            300 | 912 |
| ACC CCC AGG AGC CCA GGC TCC ACC AGG ACT CGC CGC CCT GAG ATC TCC<br>Thr Pro Arg Ser Pro Gly Ser Thr Arg Thr Arg Arg Pro Glu Ile Ser<br>305                              310                            315                          320 | 960 |
| CAG GCT GGG CCC ACG CAG GGA GAA GTG ATC CCA ACA GGC TCG TCC AAA<br>Gln Ala Gly Pro Thr Gln Gly Glu Val Ile Pro Thr Gly Ser Ser Lys<br>                          325                            330                            335 | 1008 |
| CCT GCG GGT GAC CAG CTG CCC GCG GCT CTG TGG ACC AGC AGT GCG GTG<br>Pro Ala Gly Asp Gln Leu Pro Ala Ala Leu Trp Thr Ser Ser Ala Val<br>                340                            345                            350 | 1056 |
| CTG GGA CTG CTG CTC CTG GCC TTG CCC ACG TAT CAC CTC TGG AAA CGC<br>Leu Gly Leu Leu Leu Leu Ala Leu Pro Thr Tyr His Leu Trp Lys Arg<br>                        355                            360                            365 | 1104 |
| TGC CGG CAC CTG GCT GAG GAC GAC ACC CAC CCA CCA GCT TCT CTG AGG<br>Cys Arg His Leu Ala Glu Asp Asp Thr His Pro Pro Ala Ser Leu Arg<br>370                              375                            380 | 1152 |
| CTT CTG CCC CAG GTG TCG GCC TGG GCT GGG TTA AGG GGG ACC GGC CAG<br>Leu Leu Pro Gln Val Ser Ala Trp Ala Gly Leu Arg Gly Thr Gly Gln<br>385                              390                            395                          400 | 1200 |
| GTC GGG ATC AGC CCC TCC TGAGTGGCCA GCCTTTCCCC CTGTGAAAGC<br>Val Gly Ile Ser Pro Ser<br>                405 | 1248 |
| AAAATAGCTT GGACCCCTTC AAGTTGAGAA CTGGTCAGGG CAAACCTGCC TCCCATTCTA | 1308 |
| CTCAAAGTCA TCCCTCTGCT CACAGAGATG GATGCATGTT CTGATTGCCT CTTTGGAGAA | 1368 |
| GCTCATCAGA AACTCAAAAG AAGGCCACTG TTTGTCTCAC CTACCCATGA CCTGAAGCCC | 1428 |
| CTCCCTGAGT GGTCCCCACC TTTCTGGACG GAACCACGTA CTTTTTACAT ACATTGATTC | 1488 |
| ATGTCTCACG TCTCCCTAAA AATGCGTAAG ACCAAGCTGT GCCCTGACCA CCCTGGGCCC | 1548 |
| CTGTCGTCAG GACCTCCTGA GGCTTTGGCA AATAAACCTC CTAAAATGAT AAAAAAAAAA | 1608 |
| AAAAAAAAAA AAAAAA | 1624 |

(2) INFORMATION FOR SEQ ID NO: 2:

(i) SEQUENCE CHARACTERISTICS:
        (A) LENGTH: 406 amino acids
        (B) TYPE: amino acid
        (D) TOPOLOGY: linear (ii) MOLECULE TYPE: protein (xi) SEQUENCE DESCRIPTION: SEQ ID NO: 2:

Met Asp Phe Gly Leu Ala Leu Leu Leu Ala Gly Leu Leu Gly Leu Leu
1                 5                    10                 15

Leu Gly Gln Ser Leu Gln Val Lys Pro Leu Gln Val Glu Pro Pro Glu

```
                20                  25                  30
Pro Val Val Ala Val Ala Leu Gly Ala Ser Arg Gln Leu Thr Cys Arg
             35                  40                  45
Leu Ala Cys Ala Asp Arg Gly Ala Ser Val Gln Trp Arg Gly Leu Asp
     50                  55                  60
Thr Ser Leu Gly Ala Val Gln Ser Asp Thr Gly Arg Ser Val Leu Thr
 65                  70                  75                  80
Val Arg Asn Ala Ser Leu Ser Ala Ala Gly Thr Arg Val Cys Val Gly
                 85                  90                  95
Ser Cys Gly Gly Arg Thr Phe Gln His Thr Val Gln Leu Leu Val Tyr
             100                 105                 110
Ala Phe Pro Asp Gln Leu Thr Val Ser Pro Ala Ala Leu Val Pro Gly
         115                 120                 125
Asp Pro Glu Val Ala Cys Thr Ala His Lys Val Thr Pro Val Asp Pro
     130                 135                 140
Asn Ala Leu Ser Phe Ser Leu Leu Val Gly Gln Glu Leu Glu Gly Gly
145                 150                 155                 160
Ala Gln Ala Leu Gly Pro Glu Val Gln Glu Glu Glu Glu Pro Gln
                 165                 170                 175
Gly Asp Glu Asp Val Leu Phe Arg Val Thr Glu Arg Trp Arg Leu Pro
             180                 185                 190
Pro Leu Gly Thr Pro Val Pro Pro Ala Leu Tyr Cys Gln Ala Thr Met
         195                 200                 205
Arg Leu Pro Gly Leu Glu Leu Ser His Arg Gln Ala Ile Pro Val Leu
     210                 215                 220
His Ser Pro Thr Ser Pro Glu Pro Pro Asp Thr Thr Ser Pro Glu Pro
225                 230                 235                 240
Pro Asn Thr Thr Ser Pro Glu Ser Pro Asp Thr Thr Ser Pro Glu Ser
                 245                 250                 255
Pro Asp Thr Thr Ser Gln Glu Pro Pro Asp Thr Thr Ser Gln Glu Pro
             260                 265                 270
Pro Asp Thr Thr Ser Gln Glu Pro Pro Asp Thr Thr Ser Pro Glu Pro
         275                 280                 285
Pro Asp Lys Thr Ser Pro Glu Pro Ala Pro Gln Gln Gly Ser Thr His
     290                 295                 300
Thr Pro Arg Ser Pro Gly Ser Thr Arg Thr Arg Arg Pro Glu Ile Ser
305                 310                 315                 320
Gln Ala Gly Pro Thr Gln Gly Glu Val Ile Pro Thr Gly Ser Ser Lys
                 325                 330                 335
Pro Ala Gly Asp Gln Leu Pro Ala Ala Leu Trp Thr Ser Ser Ala Val
             340                 345                 350
Leu Gly Leu Leu Leu Leu Ala Leu Pro Thr Tyr His Leu Trp Lys Arg
         355                 360                 365
Cys Arg His Leu Ala Glu Asp Asp Thr His Pro Pro Ala Ser Leu Arg
     370                 375                 380
Leu Leu Pro Gln Val Ser Ala Trp Ala Gly Leu Arg Gly Thr Gly Gln
385                 390                 395                 400
Val Gly Ile Ser Pro Ser
                 405
```

(2) INFORMATION FOR SEQ ID NO: 3:

(i) SEQUENCE CHARACTERISTICS:
        (A) LENGTH: 1539 base pairs (B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..1146

(xi) SEQUENCE DESCRIPTION: SEQ ID NO: 3:

```
ATG GAT TTC GGA CTG GCC CTC CTG CTG GCG GGG CTT CTG GGG CTC CTC        48
Met Asp Phe Gly Leu Ala Leu Leu Leu Ala Gly Leu Leu Gly Leu Leu
 1               5                  10                  15

CTC GGC CAG TCC CTC CAG GTG AAG CCC CTG CAG GTG GAG CCC CCG GAG        96
Leu Gly Gln Ser Leu Gln Val Lys Pro Leu Gln Val Glu Pro Pro Glu
                 20                  25                  30

CCG GTG GTG GCC GTG GCC TTG GGC GCC TCG CGC CAG CTC ACC TGC CGC       144
Pro Val Val Ala Val Ala Leu Gly Ala Ser Arg Gln Leu Thr Cys Arg
             35                  40                  45

CTG GCC TGC GCG GAC CGC GGG GCC TCG GTG CAG TGG CGG GGC CTG GAC       192
Leu Ala Cys Ala Asp Arg Gly Ala Ser Val Gln Trp Arg Gly Leu Asp
         50                  55                  60

ACC AGC CTG GGC GCG GTG CAG TCG GAC ACG GGC CGC AGC GTC CTC ACC       240
Thr Ser Leu Gly Ala Val Gln Ser Asp Thr Gly Arg Ser Val Leu Thr
 65                  70                  75                  80

GTG CGC AAC GCC TCG CTG TCG GCG GCC GGG ACC CGC GTG TGC GTG GGC       288
Val Arg Asn Ala Ser Leu Ser Ala Ala Gly Thr Arg Val Cys Val Gly
                 85                  90                  95

TCC TGC GGG GGC CGC ACC TTC CAG CAC ACC GTG CAG CTC CTT GTG TAC       336
Ser Cys Gly Gly Arg Thr Phe Gln His Thr Val Gln Leu Leu Val Tyr
             100                 105                 110

GCC TTC CCG GAC CAG CTG ACC GTC TCC CCA GCA GCC CTG GTG CCT GGT       384
Ala Phe Pro Asp Gln Leu Thr Val Ser Pro Ala Ala Leu Val Pro Gly
         115                 120                 125

GAC CCG GAG GTG GCC TGT ACG GCC CAC AAA GTC ACG CCC GTG GAC CCC       432
Asp Pro Glu Val Ala Cys Thr Ala His Lys Val Thr Pro Val Asp Pro
130                 135                 140

AAC GCG CTC TCC TTC TCC CTG CTC GTC GGG GGC CAG GAA CTG GAG GGG       480
Asn Ala Leu Ser Phe Ser Leu Leu Val Gly Gly Gln Glu Leu Glu Gly
145                 150                 155                 160

GCG CAA GCC CTG GGC CCG GAG GTG CAG GAG GAG GAG GAG GAG CCC CAG       528
Ala Gln Ala Leu Gly Pro Glu Val Gln Glu Glu Glu Glu Glu Pro Gln
                 165                 170                 175

GGG GAC GAG GAC GTG CTG TTC AGG GTG ACA GAG CGC TGG CGG CTG CCG       576
Gly Asp Glu Asp Val Leu Phe Arg Val Thr Glu Arg Trp Arg Leu Pro
             180                 185                 190

CCC CTG GGG ACC CCT GTC CCG CCC GCC CTC TAC TGC CAG GCC ACG ATG       624
Pro Leu Gly Thr Pro Val Pro Pro Ala Leu Tyr Cys Gln Ala Thr Met
         195                 200                 205

AGG CTG CCT GGC TTG GAG CTC AGC CAC CGC CAG GCC ATC CCC GTC CTG       672
Arg Leu Pro Gly Leu Glu Leu Ser His Arg Gln Ala Ile Pro Val Leu
     210                 215                 220

CAC AGC CCG ACC TCC CCG GAG CCT CCC GAC ACC ACC TCC CCG GAG TCT       720
His Ser Pro Thr Ser Pro Glu Pro Pro Asp Thr Thr Ser Pro Glu Ser
225                 230                 235                 240

CCC GAC ACC ACC TCC CCG GAG TCT CCC GAC ACC ACC TCC CAG GAG CCT       768
Pro Asp Thr Thr Ser Pro Glu Ser Pro Asp Thr Thr Ser Gln Glu Pro
                 245                 250                 255

CCC GAC ACC ACC TCC CCG GAG CCT CCC GAC AAG ACC TCC CCG GAG CCC       816
Pro Asp Thr Thr Ser Pro Glu Pro Pro Asp Lys Thr Ser Pro Glu Pro
             260                 265                 270
```

```
GCC CCC CAG CAG GGC TCC ACA CAC ACC CCC AGG AGC CCA GGC TCC ACC      864
Ala Pro Gln Gln Gly Ser Thr His Thr Pro Arg Ser Pro Gly Ser Thr
        275                 280                 285

AGG ACT CGC CGC CCT GAG ATC TCC CAG GCT GGG CCC ACG CAG GGA GAA      912
Arg Thr Arg Arg Pro Glu Ile Ser Gln Ala Gly Pro Thr Gln Gly Glu
        290                 295                 300

GTG ATC CCA ACA GGC TCG TCC AAA CCT GCG GGT GAC CAG CTG CCC GCG      960
Val Ile Pro Thr Gly Ser Ser Lys Pro Ala Gly Asp Gln Leu Pro Ala
305                 310                 315                 320

GCT CTG TGG ACC AGC AGT GCG GTG CTG GGA CTG CTC CTG GCC TTG         1008
Ala Leu Trp Thr Ser Ser Ala Val Leu Gly Leu Leu Leu Ala Leu
                325                 330                 335

CCC ACC TAT CAC CTC TGG AAA CGC TGC CGG CAC CTG GCT GAG GAC GAC     1056
Pro Thr Tyr His Leu Trp Lys Arg Cys Arg His Leu Ala Glu Asp Asp
            340                 345                 350

ACC CAC CCA CCA GCT TCT CTG AGG CTT CTG CCC CAG GTG TCG GCC TGG     1104
Thr His Pro Pro Ala Ser Leu Arg Leu Leu Pro Gln Val Ser Ala Trp
            355                 360                 365

GCT GGG TTA AGG GGG ACC GGC CAG GTC GGG ATC AGC CCC TCC             1146
Ala Gly Leu Arg Gly Thr Gly Gln Val Gly Ile Ser Pro Ser
        370                 375                 380

TGAGTGGCCA GCCTTTCCCC CTGTGAAAGC AAAATAGCTT GGACCCCTTC AAGTTGAGAA   1206

CTGGTCAGGG CAAACCTGCC TCCCATTCTA CTCAAAGTCA TCCCTCTGTT CACAGAGATG   1266

GATGCATGTT CTGATTGCCT CTTTGGAGAA GCTCATCAGA AACTCAAAAG AAGGCCACTG   1326

TTTGTCTCAC CTACCCATGA CCTGAAGCCC CTCCCTGAGT GGTCCCCACC TTTCTGGACG   1386

GAACCACGTA CTTTTTACAT ACATTGATTC ATGTCTCACG TCTCCCTAAA AATGCGTAAG   1446

ACCAAGCTGT GCCCTGACCA CCCTGGGCCC CTGTCGTCAG GACCTCCTGA GGCTTTGGCA   1506

AATAAACCTC CTAAAATGAA AAAAAAAAA AAA                                 1539

(2) INFORMATION FOR SEQ ID NO: 4:

(i) SEQUENCE CHARACTERISTICS:
        (A) LENGTH: 382 amino acids
        (B) TYPE: amino acid
        (D) TOPOLOGY: linear (ii) MOLECULE TYPE: protein (xi) SEQUENCE DESCRIPTION: SEQ ID NO: 4:

Met Asp Phe Gly Leu Ala Leu Leu Ala Gly Leu Leu Gly Leu Leu
 1               5                  10                  15

Leu Gly Gln Ser Leu Gln Val Lys Pro Leu Gln Val Glu Pro Pro Glu
                20                  25                  30

Pro Val Val Ala Val Ala Leu Gly Ala Ser Arg Gln Leu Thr Cys Arg
            35                  40                  45

Leu Ala Cys Ala Asp Arg Gly Ala Ser Val Gln Trp Arg Gly Leu Asp
        50                  55                  60

Thr Ser Leu Gly Ala Val Gln Ser Asp Thr Gly Arg Ser Val Leu Thr
65                  70                  75                  80

Val Arg Asn Ala Ser Leu Ser Ala Ala Gly Thr Arg Val Cys Val Gly
                85                  90                  95

Ser Cys Gly Gly Arg Thr Phe Gln His Thr Val Gln Leu Leu Val Tyr
                100                 105                 110

Ala Phe Pro Asp Gln Leu Thr Val Ser Pro Ala Ala Leu Val Pro Gly
            115                 120                 125
```

```
Asp Pro Glu Val Ala Cys Thr Ala His Lys Val Thr Pro Val Asp Pro
130                 135                 140

Asn Ala Leu Ser Phe Ser Leu Leu Val Gly Gly Gln Glu Leu Glu Gly
145                 150                 155                 160

Ala Gln Ala Leu Gly Pro Glu Val Gln Glu Glu Glu Glu Glu Pro Gln
                165                 170                 175

Gly Asp Glu Asp Val Leu Phe Arg Val Thr Glu Arg Trp Arg Leu Pro
            180                 185                 190

Pro Leu Gly Thr Pro Val Pro Pro Ala Leu Tyr Cys Gln Ala Thr Met
        195                 200                 205

Arg Leu Pro Gly Leu Glu Leu Ser His Arg Gln Ala Ile Pro Val Leu
210                 215                 220

His Ser Pro Thr Ser Pro Glu Pro Pro Asp Thr Thr Ser Pro Glu Ser
225                 230                 235                 240

Pro Asp Thr Thr Ser Pro Glu Ser Pro Asp Thr Thr Ser Gln Glu Pro
                245                 250                 255

Pro Asp Thr Thr Ser Pro Glu Pro Pro Asp Lys Thr Ser Pro Glu Pro
            260                 265                 270

Ala Pro Gln Gln Gly Ser Thr His Thr Pro Arg Ser Pro Gly Ser Thr
        275                 280                 285

Arg Thr Arg Arg Pro Glu Ile Ser Gln Ala Gly Pro Thr Gln Gly Glu
290                 295                 300

Val Ile Pro Thr Gly Ser Ser Lys Pro Ala Gly Asp Gln Leu Pro Ala
305                 310                 315                 320

Ala Leu Trp Thr Ser Ser Ala Val Leu Gly Leu Leu Leu Leu Ala Leu
                325                 330                 335

Pro Thr Tyr His Leu Trp Lys Arg Cys Arg His Leu Ala Glu Asp Asp
            340                 345                 350

Thr His Pro Pro Ala Ser Leu Arg Leu Leu Pro Gln Val Ser Ala Trp
        355                 360                 365

Ala Gly Leu Arg Gly Thr Gly Gln Val Gly Ile Ser Pro Ser
370                 375                 380

(2) INFORMATION FOR SEQ ID NO: 5:

(i) SEQUENCE CHARACTERISTICS:
        (A) LENGTH: 1721 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 4..1038

(xi) SEQUENCE DESCRIPTION: SEQ ID NO: 5:

AGC ATG GAT CGG GGC CTG GCC CTC CTG CTG GCG GGG CTT CTG GGG CTC         48
    Met Asp Arg Gly Leu Ala Leu Leu Leu Ala Gly Leu Leu Gly Leu
    1               5                   10                  15

CTC CAG CCG GGC TGC GGC CAG TCC CTC CAG GTG AAG CCC CTG CAG GTG         96
Leu Gln Pro Gly Cys Gly Gln Ser Leu Gln Val Lys Pro Leu Gln Val
                20                  25                  30

GAG CCC CCG GAG CCG GTG GTG GCC GTG GCC CTG GGC GCC TCT CGC CAG        144
Glu Pro Pro Glu Pro Val Val Ala Val Ala Leu Gly Ala Ser Arg Gln
            35                  40                  45

CTC ACC TGC CGC CTG GAC TGC GCG GAC CGC GGG GCC ACG GTG CAG TGG        192
Leu Thr Cys Arg Leu Asp Cys Ala Asp Arg Gly Ala Thr Val Gln Trp
```

-continued

```
                50                      55                      60
CGG GGC CTG GAC ACC AGC CTG GGC GCG GTG CAG TCG GAC GCG GGC CGC       240
Arg Gly Leu Asp Thr Ser Leu Gly Ala Val Gln Ser Asp Ala Gly Arg
         65                      70                      75

AGC GTC CTC ACC GTG CGC AAC GCC TCG CTG TCG GCG GCC GGG ACC CGT       288
Ser Val Leu Thr Val Arg Asn Ala Ser Leu Ser Ala Ala Gly Thr Arg
 80                      85                      90                      95

GTG TGC GTG GGC TCC TGC GGG GGC CGC ACC TTC CAG CAC ACC GTG CGG       336
Val Cys Val Gly Ser Cys Gly Gly Arg Thr Phe Gln His Thr Val Arg
                    100                     105                     110

CTC CTT GTG TAC GCC TTC CCG GAC CAG CTG ACC ATC TCC CCG GCA GCC       384
Leu Leu Val Tyr Ala Phe Pro Asp Gln Leu Thr Ile Ser Pro Ala Ala
                115                     120                     125

CTG GTG CCT GGT GAC CCG GAG GTG GCC TGT ACG GCC CAC AAA GTC ACG       432
Leu Val Pro Gly Asp Pro Glu Val Ala Cys Thr Ala His Lys Val Thr
            130                     135                     140

CCT GTG GAC CCC AAT GCG CTC TCC TTC TCC CTG CTC CTG GGG GAC CAG       480
Pro Val Asp Pro Asn Ala Leu Ser Phe Ser Leu Leu Leu Gly Asp Gln
145                     150                     155

GAA CTG GAG GGG GCC CAG GCT CTG GGC CCG GAG GTG GAG GAG GAG GAG       528
Glu Leu Glu Gly Ala Gln Ala Leu Gly Pro Glu Val Glu Glu Glu Glu
160                     165                     170                     175

GAG GAG CCC CAG GAG GAG GAG GAC GTG CTG TTC AGG GTG ACA GAG CGC       576
Glu Glu Pro Gln Glu Glu Glu Asp Val Leu Phe Arg Val Thr Glu Arg
                    180                     185                     190

TGG CGG CTG CCG ACC CTG GCA ACC CCT GTC CTG CCC GCG CTC TAC TGC       624
Trp Arg Leu Pro Thr Leu Ala Thr Pro Val Leu Pro Ala Leu Tyr Cys
                195                     200                     205

CAG GCC ACG ATG AGG CTG CCT GGC TTG GAG CTC AGC CAC CGC CAG GCC       672
Gln Ala Thr Met Arg Leu Pro Gly Leu Glu Leu Ser His Arg Gln Ala
            210                     215                     220

ATC CCG GTC CTG CAC GGC CCG ACC TCC CGG GAG CCC CCC GAC ACG ACC       720
Ile Pro Val Leu His Gly Pro Thr Ser Arg Glu Pro Pro Asp Thr Thr
225                     230                     235

TCC CCG GAA CCC CGG GCC GCG ACC TCC CCG GAG ACC ACC CCC CAG CAG       768
Ser Pro Glu Pro Arg Ala Ala Thr Ser Pro Glu Thr Thr Pro Gln Gln
240                     245                     250                     255

GGC TCC ACA CAC AGC CCC AGG AGC CCG GGC TCT ACC AGG ACT TGC CGC       816
Gly Ser Thr His Ser Pro Arg Ser Pro Gly Ser Thr Arg Thr Cys Arg
                    260                     265                     270

CCT GAG ATC TCC CAG GCT GGG CCC ACG CAG GGA GAA GTG ATC CCA ACA       864
Pro Glu Ile Ser Gln Ala Gly Pro Thr Gln Gly Glu Val Ile Pro Thr
                275                     280                     285

GGC TCG TCC AAA CCT ACG GGT GAC CAG CTG CCC GCG GCT CTG TGG ACC       912
Gly Ser Ser Lys Pro Thr Gly Asp Gln Leu Pro Ala Ala Leu Trp Thr
            290                     295                     300

AGC AGT GCG GTG CTG GGA CTG CTC CTC CTG GCT TTG CCC ACC TAC CAC       960
Ser Ser Ala Val Leu Gly Leu Leu Leu Leu Ala Leu Pro Thr Tyr His
305                     310                     315

CTC TGG AAA CGT TGC CGG CAC CTG GCT GAG GAC GGC GCC CAC CCA CCA      1008
Leu Trp Lys Arg Cys Arg His Leu Ala Glu Asp Gly Ala His Pro Pro
320                     325                     330                     335

GCT TCT CTG AGT AGC CAG CCC TTC CCC CTG TGAAGGGAAA ATAGGTTGGA        1058
Ala Ser Leu Ser Ser Gln Pro Phe Pro Leu
                    340                     345

CCCCTTCAAG CTGAGAACTG GTCGGGGCAA ACCTGCCTCC CATTCTATTC AAAGTCATCG    1118

CTCTGGTCAC AGAGAGGGAC GCACATTCTG ATTGCCTCCT TTGGAAAGGC TCATCAGAAA    1178

CTCAAAAGAA GGTGATCGTT TGTCCCGCCT ACCCGTGACC TGGAAGCCCC CGCCCCGCTC    1238
```

-continued

```
GAGTGACCCC TGACTTTCTG GACGGAACCA ACGTACTTCT TACATATATT GATTCATGTG      1298

TCATATCTCC CTAAAATGCG TAAAACCAGC TGTGCCCCGA CCACCTTGGG CCCCTGCCAT      1358

CAGGACCTCC TGAGGCTTTG GCAAATAAAC CTCCTAAAAG GATAGAAACT GAAACTTGTG      1418

GCCGGGCGCG GTGGCTCAAG CCTGTAATCC CAGCACTTTG GGAGGCCGAG GTGGGTGGAT      1478

CACGAGGTCA GGAGATCGAG ACCATCCTGG CTAACCCGTG AAACCCCGTC TCTACTAAAA      1538

AAATACAAAA ATTAGCCGGG AGCGGTGGCG GGCGCCTGTA GTCCCAGCTA CTCGGGAGGC      1598

TGAGGCAGGA GAATGGCGTG AACCCGGGAG GCGGAGCTTG CAGTGAGCTG AGATCCGGCC      1658

ACTGCACTCC AGCCTGGGGG ACAGAGCGAG ACTCCGTCTC AAAAAAAAAA AAAAAAAAA      1718

AAA                                                                    1721
```

(2) INFORMATION FOR SEQ ID NO: 6:

(i) SEQUENCE CHARACTERISTICS:
  (A) LENGTH: 345 amino acids
  (B) TYPE: amino acid
  (D) TOPOLOGY: linear (ii) MOLECULE TYPE: protein (xi) SEQUENCE DESCRIPTION: SEQ ID NO: 6:

```
Met Asp Arg Gly Leu Ala Leu Leu Ala Gly Leu Leu Gly Leu Leu
 1               5                  10                  15

Gln Pro Gly Cys Gly Gln Ser Leu Gln Val Lys Pro Leu Gln Val Glu
                20                  25                  30

Pro Pro Glu Pro Val Val Ala Val Ala Leu Gly Ala Ser Arg Gln Leu
            35                  40                  45

Thr Cys Arg Leu Asp Cys Ala Asp Arg Gly Ala Thr Val Gln Trp Arg
        50                  55                  60

Gly Leu Asp Thr Ser Leu Gly Ala Val Gln Ser Asp Ala Gly Arg Ser
 65                 70                  75                  80

Val Leu Thr Val Arg Asn Ala Ser Leu Ser Ala Ala Gly Thr Arg Val
                85                  90                  95

Cys Val Gly Ser Cys Gly Gly Arg Thr Phe Gln His Thr Val Arg Leu
                100                 105                 110

Leu Val Tyr Ala Phe Pro Asp Gln Leu Thr Ile Ser Pro Ala Ala Leu
            115                 120                 125

Val Pro Gly Asp Pro Glu Val Ala Cys Thr Ala His Lys Val Thr Pro
        130                 135                 140

Val Asp Pro Asn Ala Leu Ser Phe Ser Leu Leu Leu Gly Asp Gln Glu
145                 150                 155                 160

Leu Glu Gly Ala Gln Ala Leu Gly Pro Glu Val Glu Glu Glu Glu
                165                 170                 175

Glu Pro Gln Glu Glu Asp Val Leu Phe Arg Val Thr Glu Arg Trp
            180                 185                 190

Arg Leu Pro Thr Leu Ala Thr Pro Val Leu Pro Ala Leu Tyr Cys Gln
        195                 200                 205

Ala Thr Met Arg Leu Pro Gly Leu Glu Leu Ser His Arg Gln Ala Ile
        210                 215                 220

Pro Val Leu His Gly Pro Thr Ser Arg Glu Pro Pro Asp Thr Thr Ser
225                 230                 235                 240

Pro Glu Pro Arg Ala Ala Thr Ser Pro Glu Thr Thr Pro Gln Gln Gly
                245                 250                 255
```

```
Ser Thr His Ser Pro Arg Ser Pro Gly Ser Thr Arg Thr Cys Arg Pro
            260                 265                 270

Glu Ile Ser Gln Ala Gly Pro Thr Gln Gly Glu Val Ile Pro Thr Gly
        275                 280                 285

Ser Ser Lys Pro Thr Gly Asp Gln Leu Pro Ala Ala Leu Trp Thr Ser
    290                 295                 300

Ser Ala Val Leu Gly Leu Leu Leu Ala Leu Pro Thr Tyr His Leu
305                 310                 315                 320

Trp Lys Arg Cys Arg His Leu Ala Glu Asp Gly Ala His Pro Pro Ala
                325                 330                 335

Ser Leu Ser Ser Gln Pro Phe Pro Leu
            340                 345

(2) INFORMATION FOR SEQ ID NO: 7:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (xi) SEQUENCE DESCRIPTION: SEQ ID NO: 7:

CTCTACTGCC AGGCCACG                                                    18

(2) INFORMATION FOR SEQ ID NO: 8:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (xi) SEQUENCE DESCRIPTION: SEQ ID NO: 8:

AGCCTGGGAG ATCTCAGGG                                                   19

(2) INFORMATION FOR SEQ ID NO: 9:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO: 9:

GCCACGATGA GGCTGCCTGG                                                  20

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: unknown (xi) SEQUENCE DESCRIPTION: SEQ ID NO: 10:

GTGGAGCCTG GGCTCCTGGG                                                  20

(2) INFORMATION FOR SEQ ID NO: 11:

(i) SEQUENCE CHARACTERISTICS:
        (A) LENGTH: 32 base pairs
        (B) TYPE: nucleic acid
        (C) STRANDEDNESS: single
        (D) TOPOLOGY: linear
```

```
        (xi) SEQUENCE DESCRIPTION: SEQ ID NO: 11:

GGAAGCTTCC ACCATGGATT TCGGACTGGC CC                                    32

(2) INFORMATION FOR SEQ ID NO: 12:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO: 12:

CCGACTAGTG TCGGGCTGTG CAGGAC                                           26

(2) INFORMATION FOR SEQ ID NO: 13:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO: 13:

GGACTAGTGG TTTGGACGAG CCTGTTG                                          27

(2) INFORMATION FOR SEQ ID NO: 14:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (xi) SEQUENCE DESCRIPTION: SEQ ID NO: 14:

Gly Leu Asp Thr Ser Leu
1               5

(2) INFORMATION FOR SEQ ID NO: 15:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ix) FEATURE:
            (A) NAME/KEY: Region
            (B) LOCATION: 2
            (D) OTHER INFORMATION: /product= "OTHER"
                /label= variable
                /note= "Xaa = Ile or Leu"

(ix) FEATURE:
            (A) NAME/KEY: Region
            (B) LOCATION: 3
            (D) OTHER INFORMATION: /product= "OTHER"
                /label= variable
                /note= "Xaa = Asp or Glu"

(ix) FEATURE:
            (A) NAME/KEY: Region
            (B) LOCATION: 4
            (D) OTHER INFORMATION: /product= "OTHER"
                /label= variable
                /note= "Xaa = Thr or Ser"

(ix) FEATURE:
            (A) NAME/KEY: Region
            (B) LOCATION: 5
            (D) OTHER INFORMATION: /product= "OTHER"
                /label= variable
```

```
       /note= "Xaa = Pro or Ser"

(xi) SEQUENCE DESCRIPTION: SEQ ID NO: 15:

Gly Xaa Xaa Xaa Xaa Leu
1               5

(2) INFORMATION FOR SEQ ID NO: 16:

(i) SEQUENCE CHARACTERISTICS:
         (A) LENGTH: 6 amino acids
         (B) TYPE: amino acid
         (C) STRANDEDNESS: <Unknown>
         (D) TOPOLOGY: linear (xi) SEQUENCE DESCRIPTION: SEQ ID NO: 16:

Gln Ile Asp Ser Pro Leu
1               5

(2) INFORMATION FOR SEQ ID NO: 17:

(i) SEQUENCE CHARACTERISTICS:
         (A) LENGTH: 5 amino acids
         (B) TYPE: amino acid
         (C) STRANDEDNESS: <Unknown>
         (D) TOPOLOGY: linear (xi) SEQUENCE DESCRIPTION: SEQ ID NO: 17:

Leu Asp Thr Ser Leu
1               5
```